United States Patent [19]

Di Perna et al.

[11] Patent Number: 5,480,294
[45] Date of Patent: Jan. 2, 1996

[54] PERISTALTIC PUMP MODULE HAVING JAWS FOR GRIPPING A PERISTALTIC PUMP TUBE CASSETT

[75] Inventors: Paul M. Di Perna, Long Grove; Richard L. West, Lake Villa, both of Ill.

[73] Assignee: Baxter International Inc., Deerfield, Ill.

[21] Appl. No.: 172,654

[22] Filed: Dec. 22, 1993

[51] Int. Cl.$^6$ .................................................. F04B 43/08
[52] U.S. Cl. .................................. 417/477.2; 604/153
[58] Field of Search .................................. 417/474, 475, 417/476, 477 R, 477 A, 477 F, 477 G, 477 E, 477.1, 477, 2, 477.7, 477.8, 477.6; 604/153

[56] References Cited

U.S. PATENT DOCUMENTS

| | | | |
|---|---|---|---|
| 3,565,286 | 2/1971 | Latham, Jr. | 222/4 |
| 3,709,222 | 1/1973 | DeVries | 128/213 |
| 3,963,023 | 6/1976 | Hankinson | 417/477 |
| 4,070,725 | 1/1978 | Austin et al. | 417/477 |
| 4,205,948 | 6/1980 | Jones | 417/477 |
| 4,211,519 | 7/1980 | Hogan | 417/477 A |
| 4,218,197 | 8/1980 | Meyer et al. | 417/477 |
| 4,472,116 | 9/1984 | Wenstrup | 417/477 |
| 4,526,515 | 7/1985 | DeVries | 417/475 |
| 4,537,561 | 8/1985 | Xanthopoulos | 417/477 A |
| 4,585,436 | 4/1986 | Davis et al. | 604/29 |
| 4,599,055 | 7/1986 | Dykstra | 417/477 A |
| 4,673,334 | 6/1987 | Allington et al. | 417/477 A |
| 4,674,962 | 6/1987 | Gardineer | 417/477 |
| 4,681,568 | 7/1987 | Troutner | 604/250 |
| 4,692,138 | 9/1987 | Troutner et al. | 604/4 |
| 4,705,464 | 11/1987 | Arimond | 417/477 |
| 4,735,558 | 4/1988 | Kienholz et al. | 417/477 |
| 4,824,339 | 4/1989 | Bainbridge | 417/477 A |
| 4,861,242 | 8/1989 | Finsterwald | 417/477 A |
| 4,909,713 | 3/1990 | Finsterwald et al. | 417/477 |
| 5,044,902 | 9/1991 | Malbec | 417/477 |
| 5,125,891 | 6/1992 | Hossain et al. | 417/477 |
| 5,267,956 | 12/1993 | Beuchat | 604/30 |
| 5,273,517 | 12/1993 | Barone et al. | 494/37 |
| 5,311,908 | 5/1994 | Barone et al. | 137/881 |

FOREIGN PATENT DOCUMENTS

| 9322560 | 11/1993 | WIPO | 417/477 A |
|---|---|---|---|

*Primary Examiner*—Richard A. Bertsch
*Assistant Examiner*—Peter G. Korytnyk
*Attorney, Agent, or Firm*—Bradford R. L. Price; Joseph B. Barrett; Daniel D. Ryan

[57] ABSTRACT

A peristaltic pumping apparatus includes a peristaltic pump rotor and pump race. A pump tube cassette includes a body for supporting a flexible tubing loop in an erect, outwardly bowed position for placement within the pump race and for removal from the pump race. A surface juxtaposed the peristaltic pump rotor and race carries a gripping jaw assembly. The gripping jaw assembly opens to receive the pump tube cassette body as the body is moved toward the pump rotor to place the tubing loop within the pump race. The gripping jaw assembly closes to secure the pump tube holder body on the surface in an orientation in which the tubing loop lies within the pump race for engagement with the peristaltic pump rotor.

18 Claims, 47 Drawing Sheets

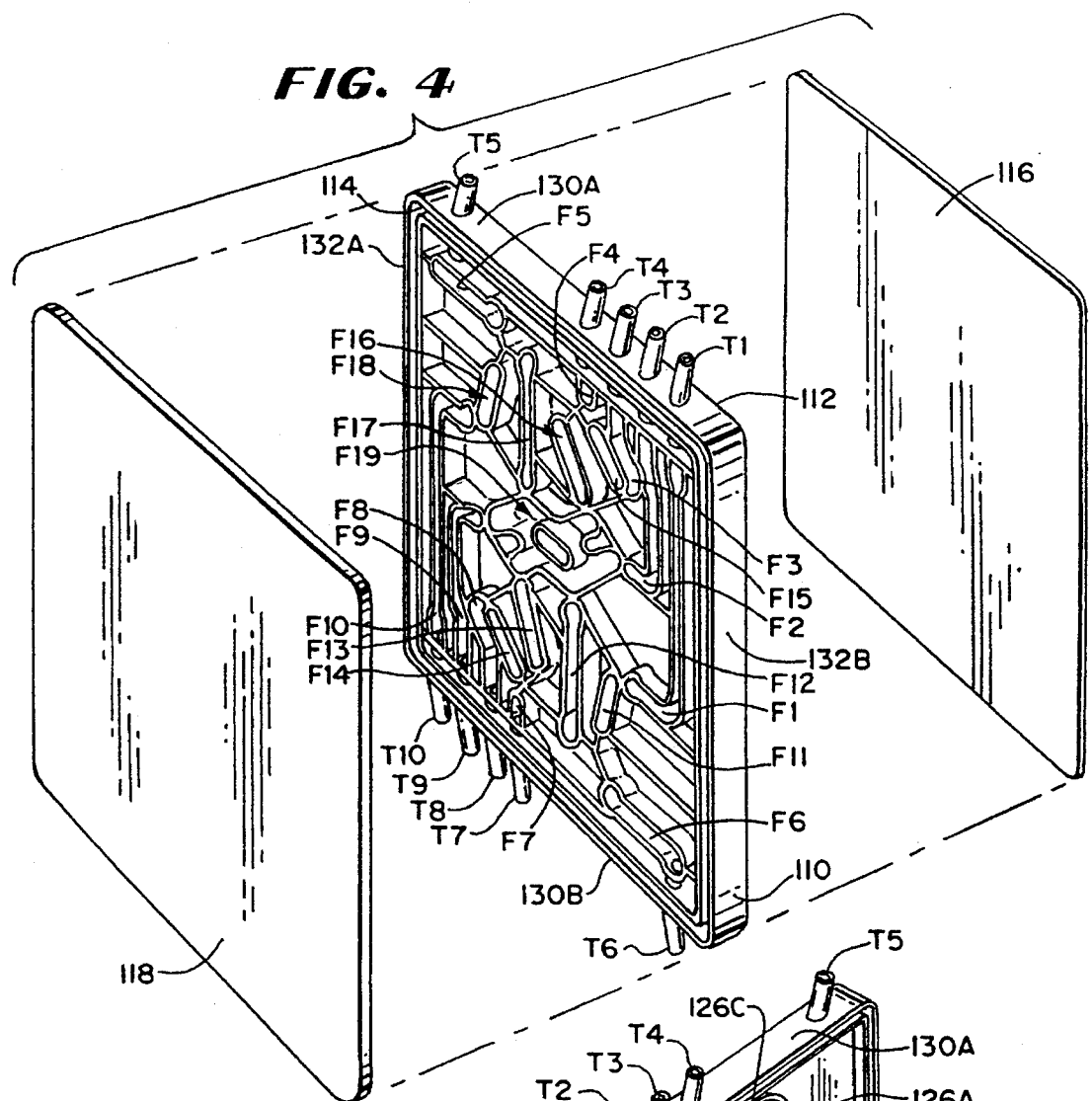
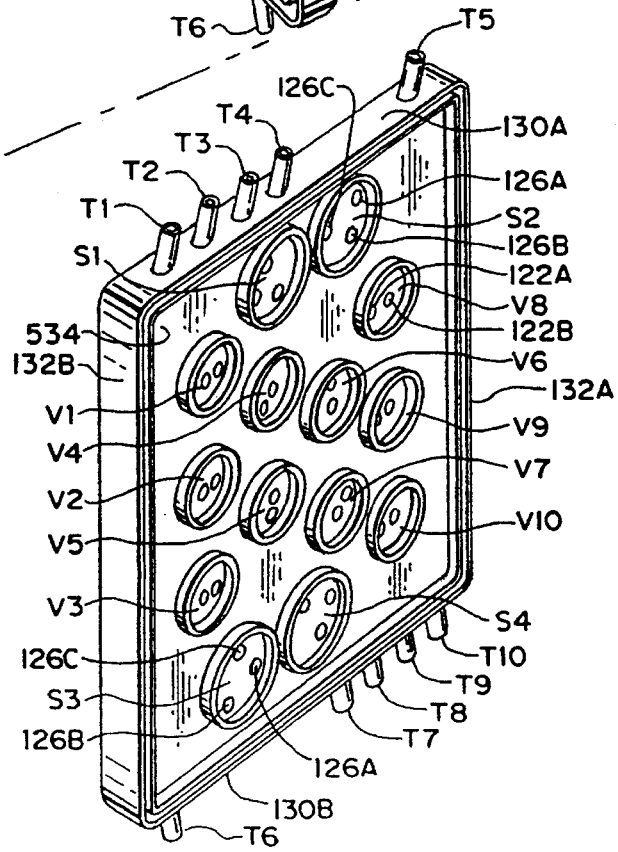

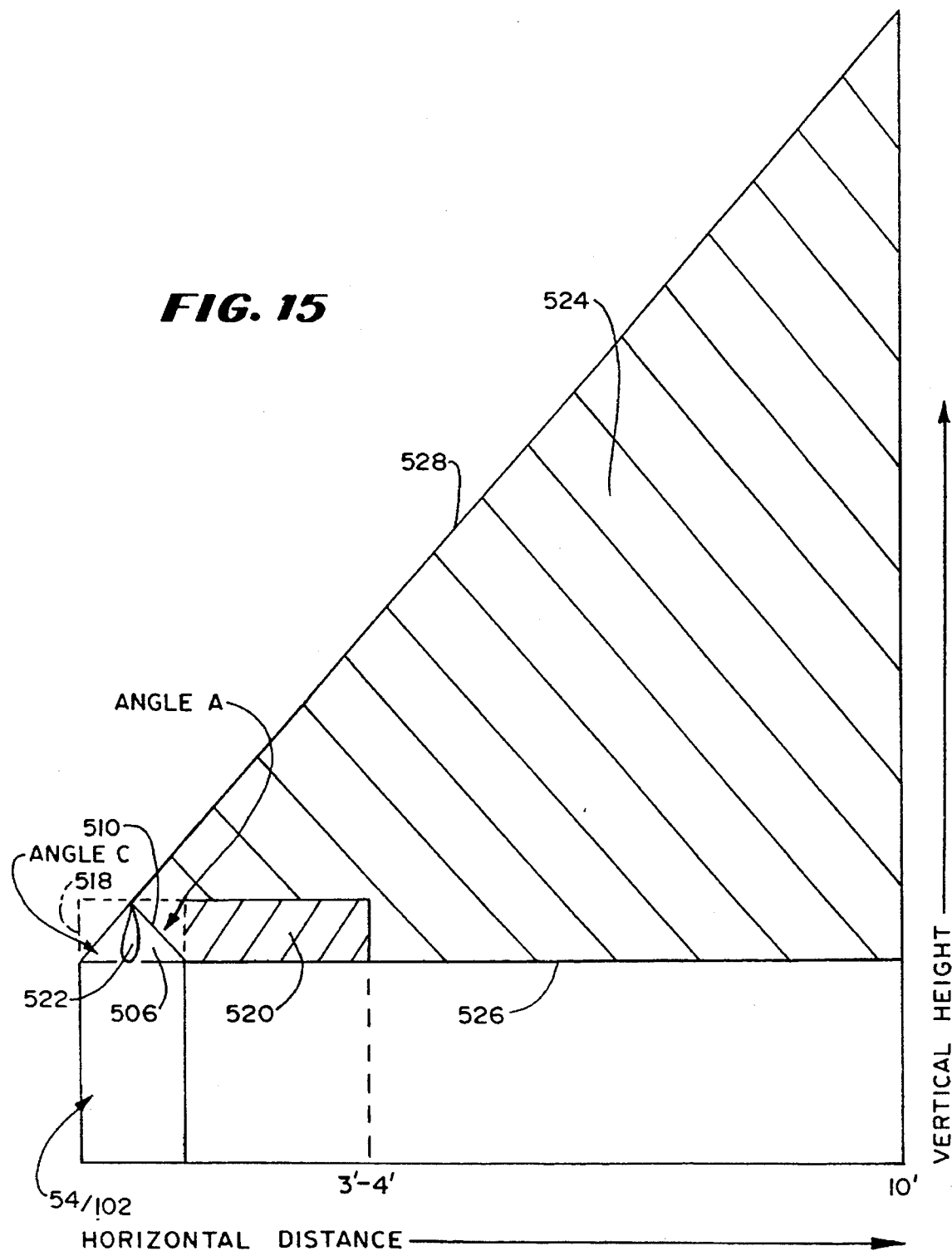

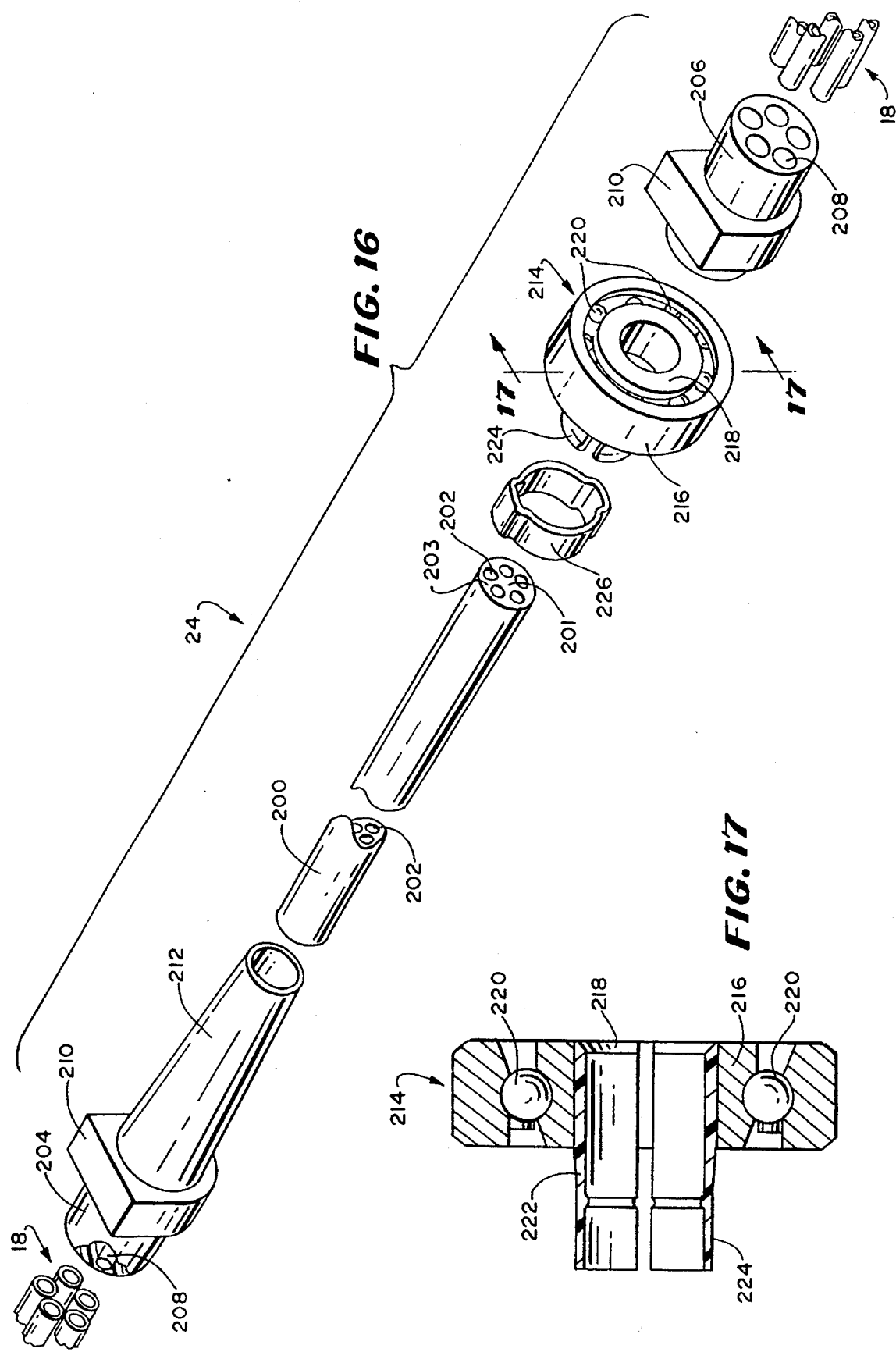

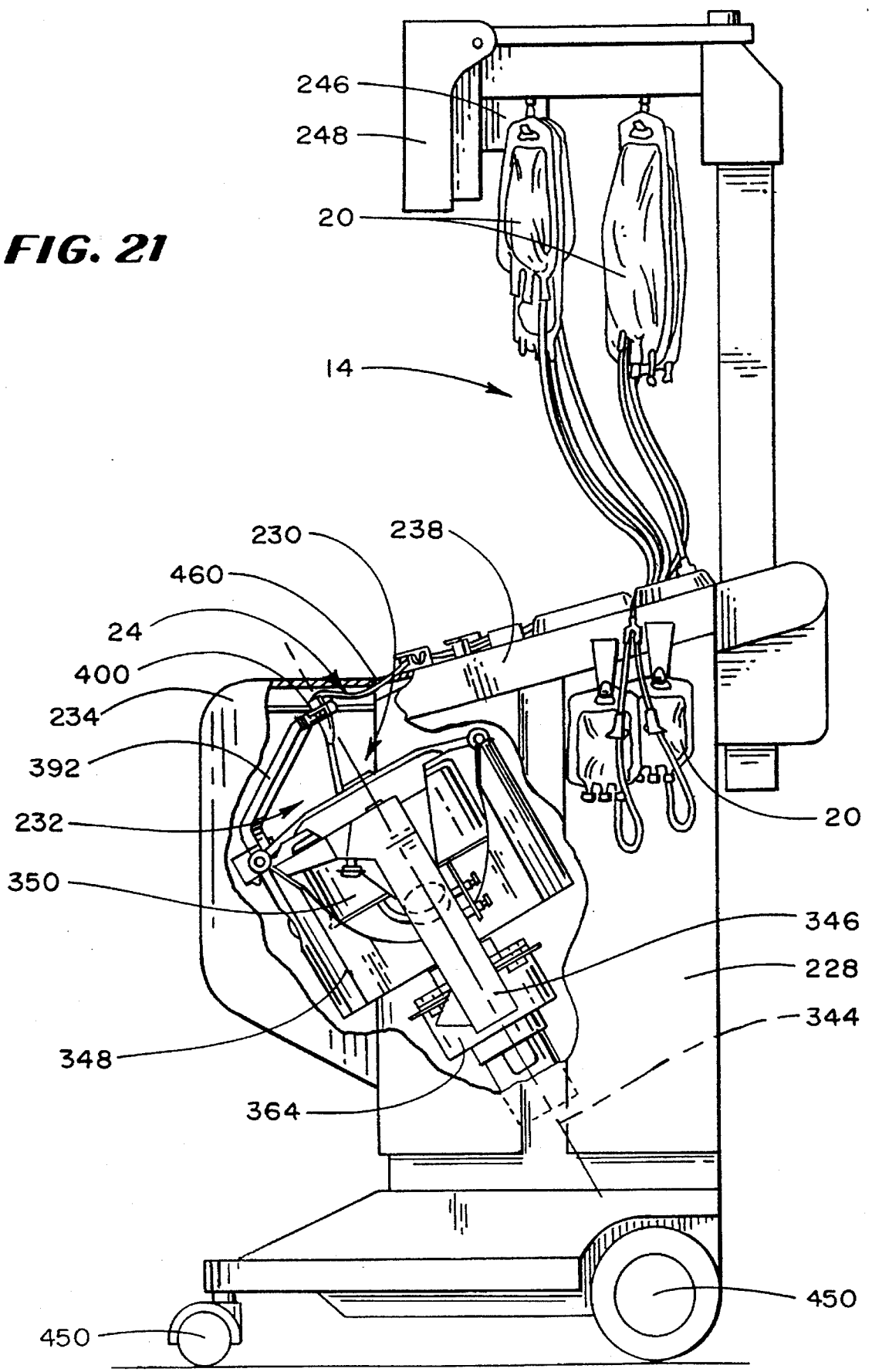

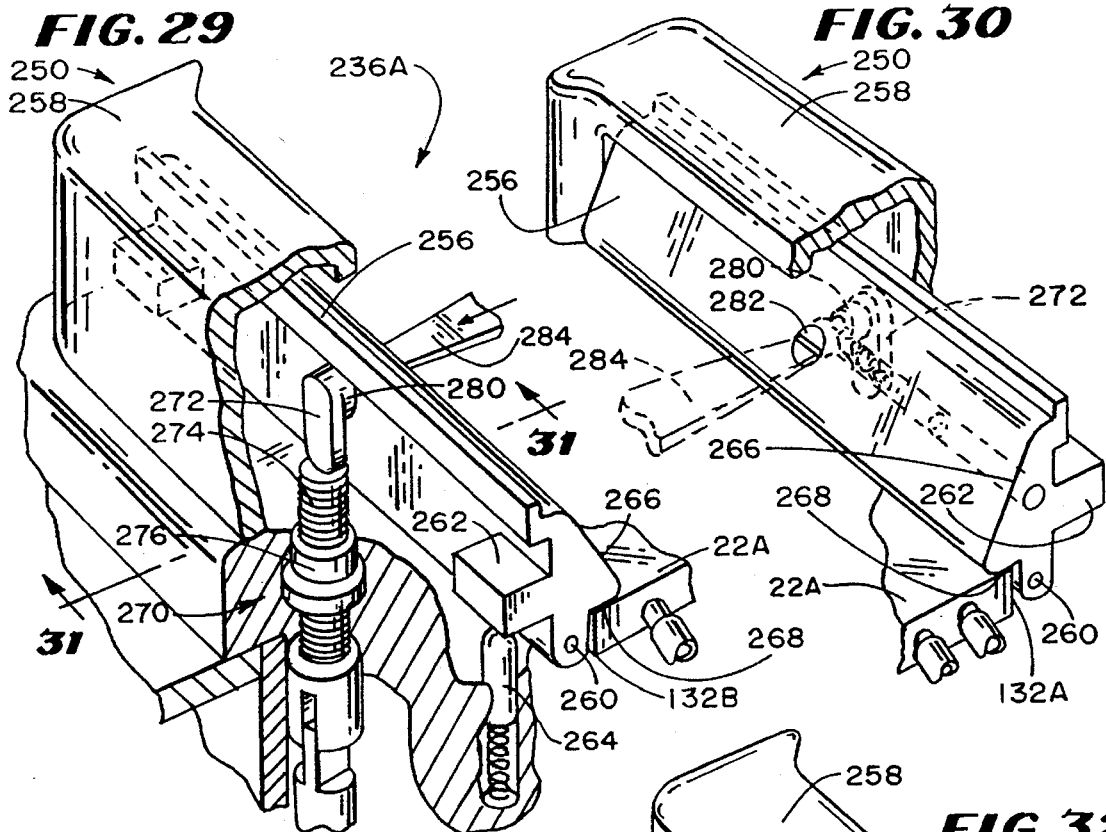
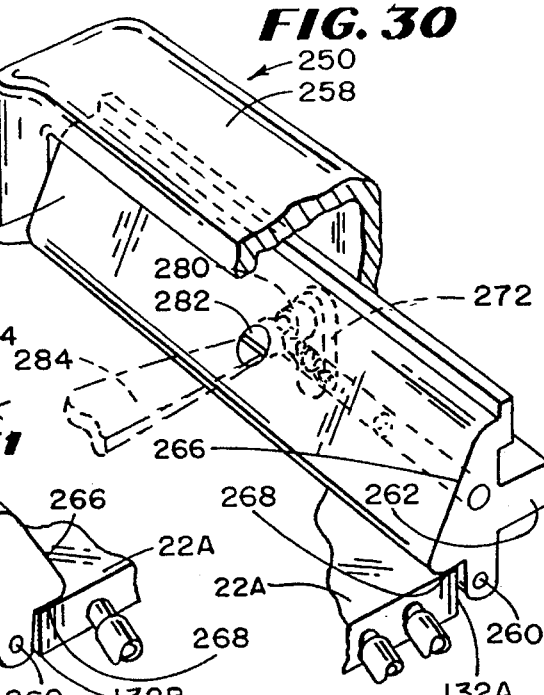
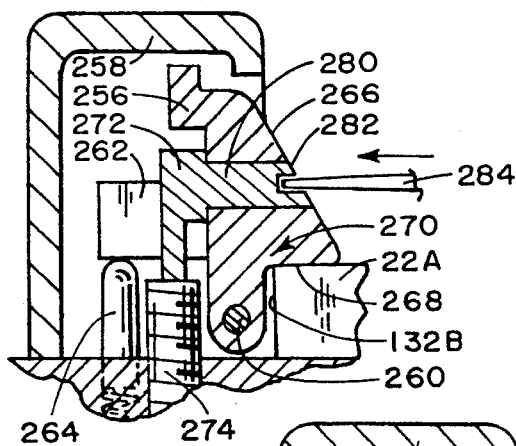
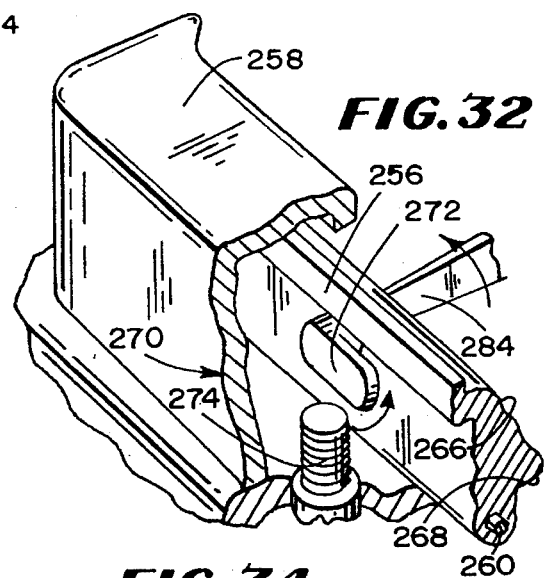
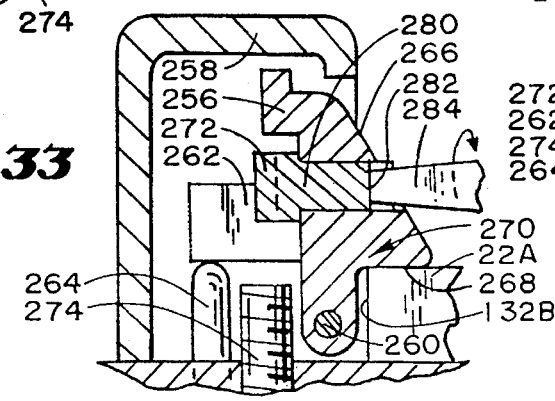
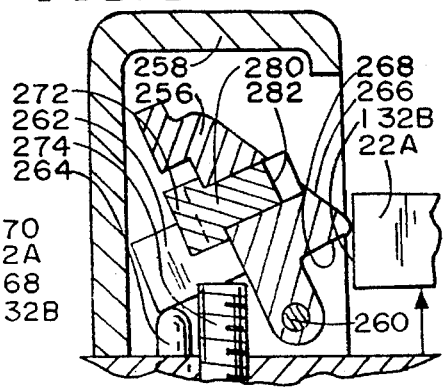

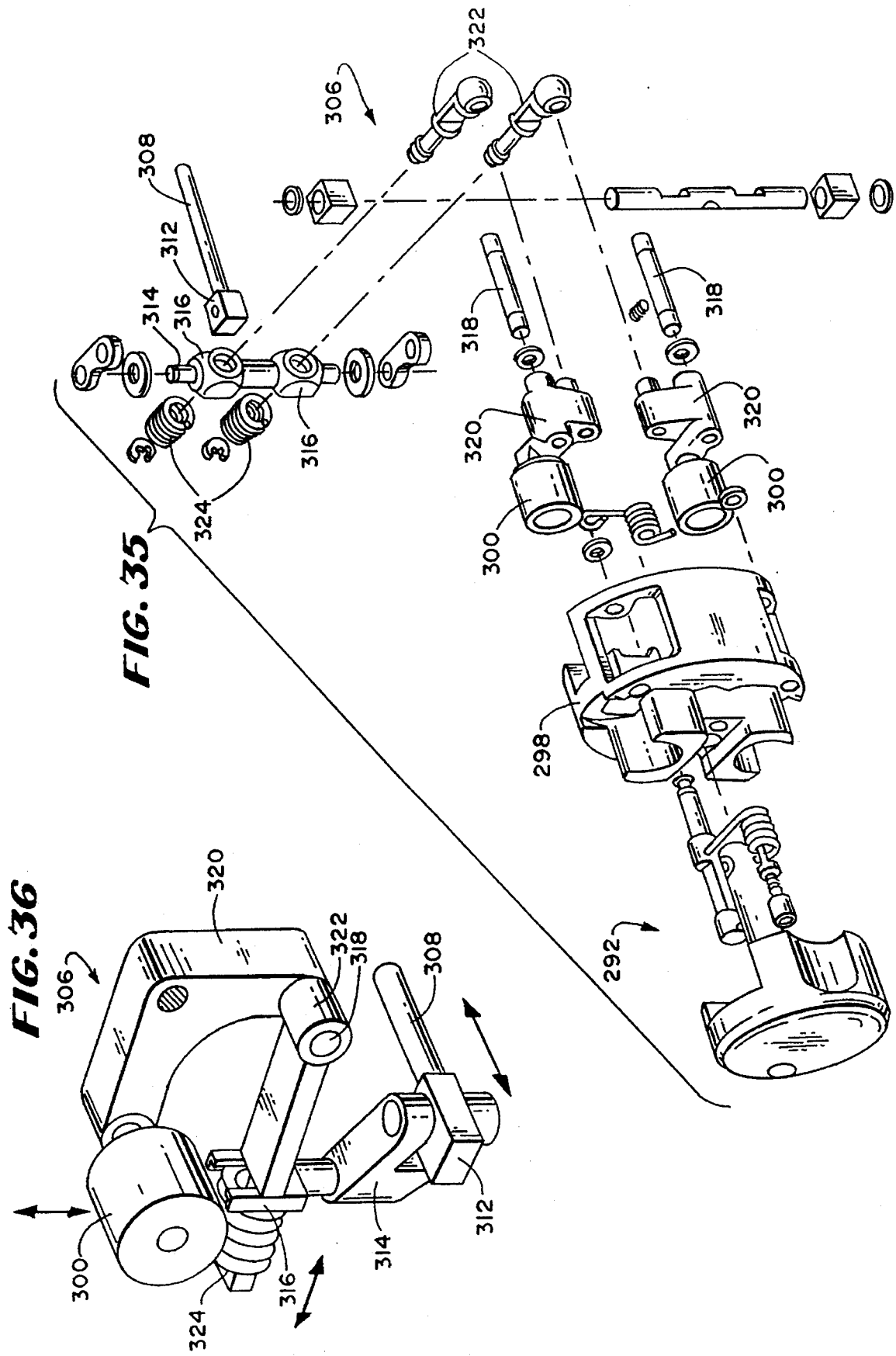

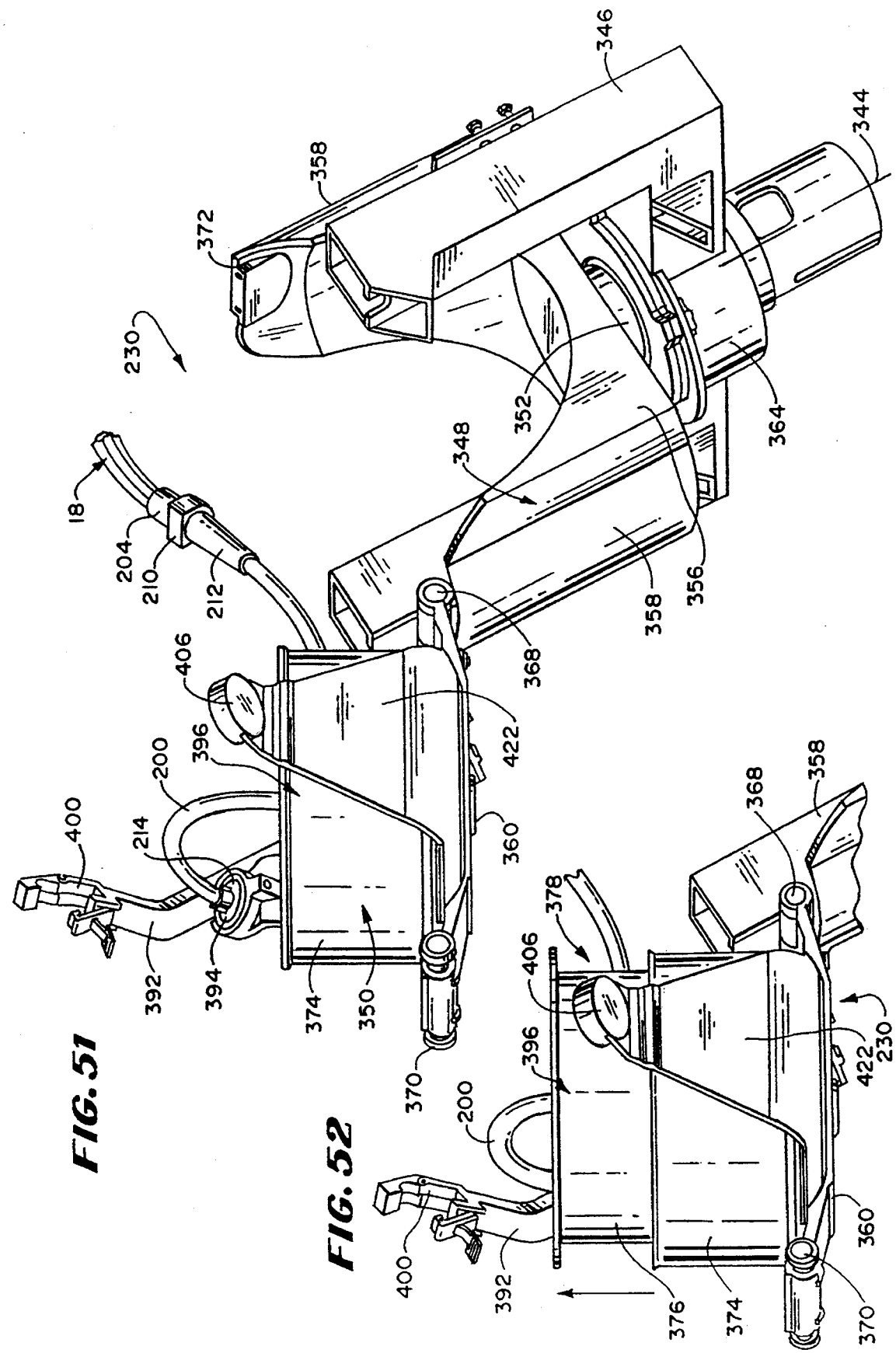

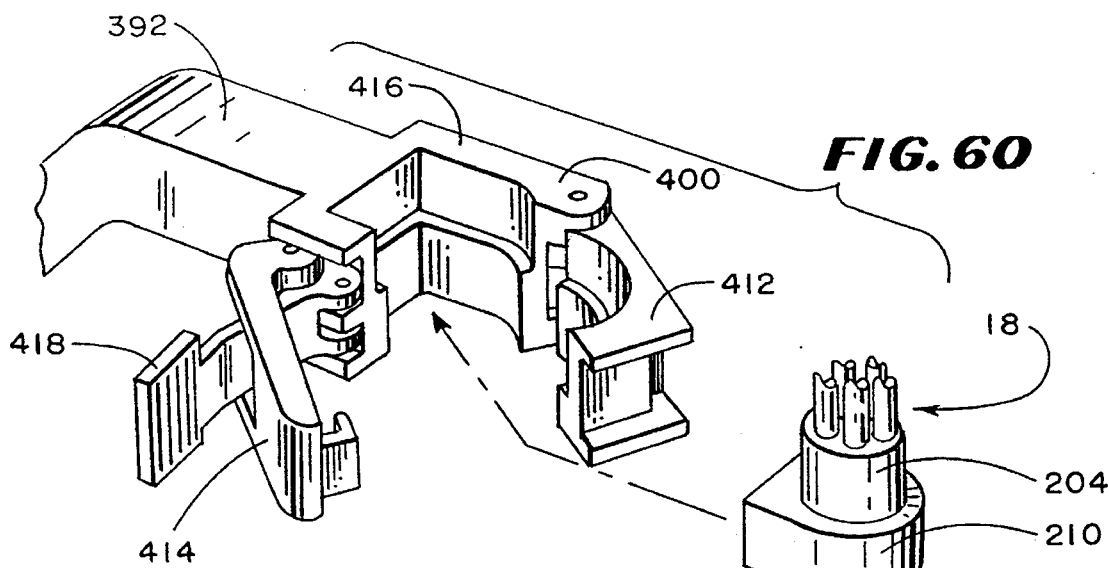
FIG. 60
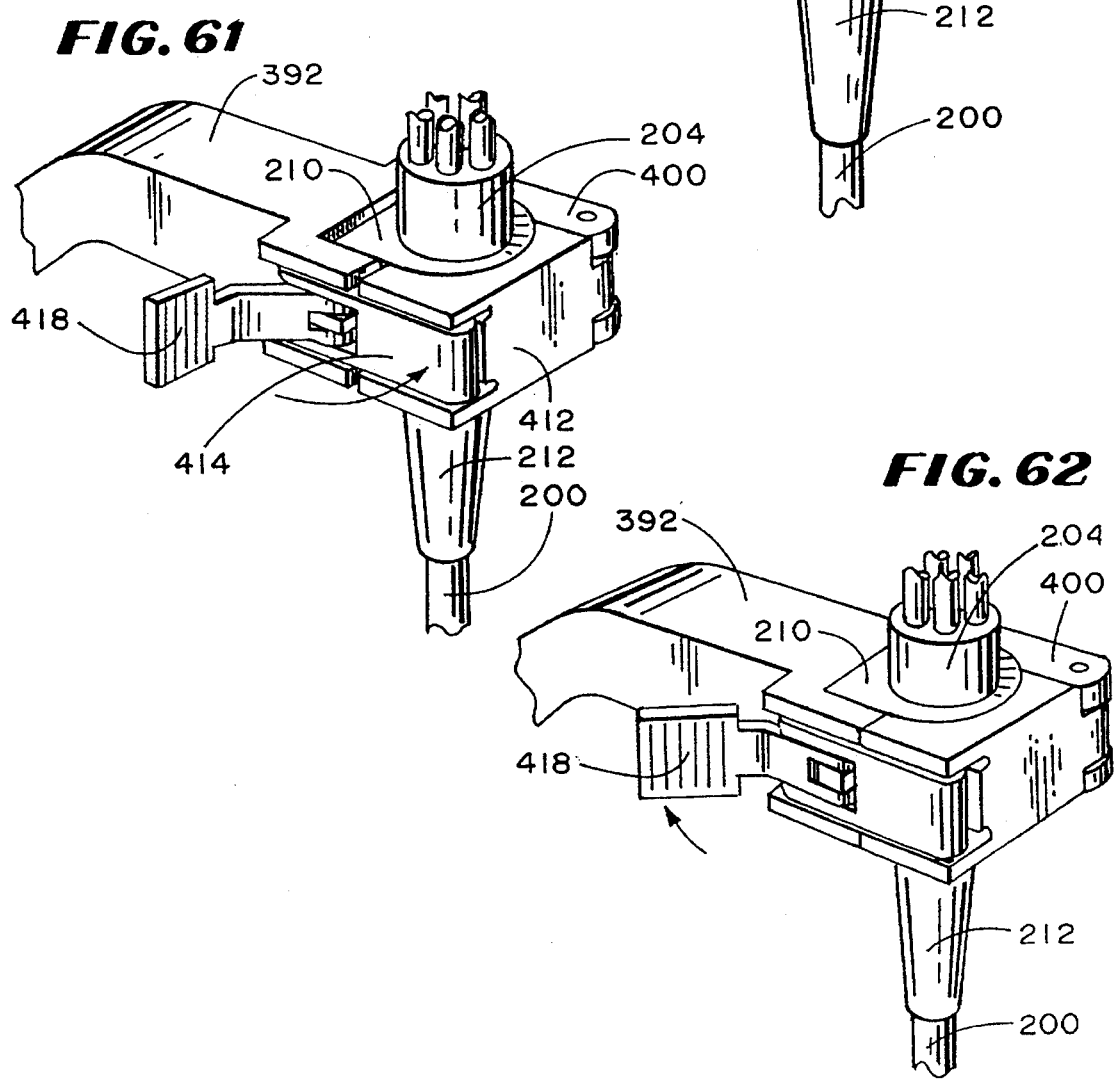
FIG. 61
FIG. 62

PERISTALTIC PUMP MODULE HAVING JAWS FOR GRIPPING A PERISTALTIC PUMP TUBE CASSETT

FIELD OF THE INVENTION

The invention relates to blood processing systems and apparatus.

BACKGROUND OF THE INVENTION

Today people routinely separate whole blood by centrifugation into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Conventional centrifuges often do not permit easy access to the areas where the disposable systems reside during use. As a result, loading and unloading operations can be time consuming and tedious.

Disposable systems are often preformed into desired shapes to simplify the loading and unloading process. However, this approach is often counterproductive, as it increases the cost of the disposables.

SUMMARY OF THE INVENTION

The invention makes possible improved liquid processing systems that provide easy access to external and internal components for loading and unloading disposable processing components. The invention achieves this objective without complicating or increasing the cost of the disposable components. The invention allows relatively inexpensive and straightforward disposable components to be used.

The invention provides a gripping mechanism for a peristaltic pump tube holder that facilitates loading and unloading of the pump tube within a peristaltic pump race.

The invention provides a peristaltic pumping apparatus. The apparatus includes a peristaltic pumping element including a pump rotor and pump race. A pump tube holder includes a body for supporting a flexible tubing loop in an erect, outwardly bowed position for placement within the pump race and for removal from the pump race by moving the body, respectively, toward and away from the pumping element.

The apparatus further includes a surface juxtaposed the peristaltic pumping element. The surface carries a gripping jaw assembly. The gripping jaw assembly opens to receive the pump tube holder body as the body is moved toward the pumping element to place the tubing loop within the pump race. The gripping jaw assembly closes to secure the pump tube holder body on the surface in an orientation in which the tubing loop lies within the pump race for engagement with the peristaltic pump rotor.

In a preferred embodiment, the gripping jaw assembly opens to release the pump tube holder body as the body is moved away from the pumping element to remove the tubing loop from the pump race.

In a preferred embodiment, the gripping jaw assembly includes a mechanism for releasably locking the gripping jaw assembly when closed.

The features and advantages of the invention will become apparent from the following description, the drawings, and the claims.

BRIEF DESCRIPTION OF THE DRAWINGS

FIG. 4 is an exploded perspective view of a fluid control cassette that the fluid processing assembly shown in FIG. 2 incorporates, looking at the back side of the cassette body;

FIG. 5 is a perspective view of the front side of the cassette body shown in FIG. 4;

FIG. 15 is a diagrammatic chart showing the enhanced field of view that the drip chamber shown in FIG. 13 provides;

FIG. 16 is an exploded perspective view of the umbilicus associated with the fluid processing assembly shown in FIG. 2;

FIG. 17 is a side section view of the thrust bearing member carried by the umbilicus, taken generally along line 17—17 in FIG. 16;

FIG. 21 A is a side elevation view like FIG. 21, but showing the angled relationship of the various components;

FIGS. 29 to 31 are enlarged views, with portions broken away and in section, of the locking mechanism for one of the gripping elements shown in FIG. 24;

FIGS. 32 to 34 are enlarged views, with portions broken away and in section, showing the manually release of the locking mechanism shown in FIGS. 29 to 31, in the event of a power or mechanical failure;

FIG. 35 is an exploded perspective view of the rotor assembly and its associated roller location mechanism that the pump module shown in FIG. 26 incorporates;

FIG. 36 is an assembled perspective view of the roller location mechanism shown in FIG. 35;

FIG. 51 is an enlarged perspective view of the centrifuge shown in FIG. 59, with the associated chamber assembly being shown in its loading position (as FIG. 50 also shows);

FIG. 52 is an enlarged perspective view of the chamber assembly shown in FIG. 51, with the spool upraised from the bowl to receive a disposable processing chamber;

FIGS. 60 to 62 show the upper umbilicus mount in association with the upper umbilicus support member;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
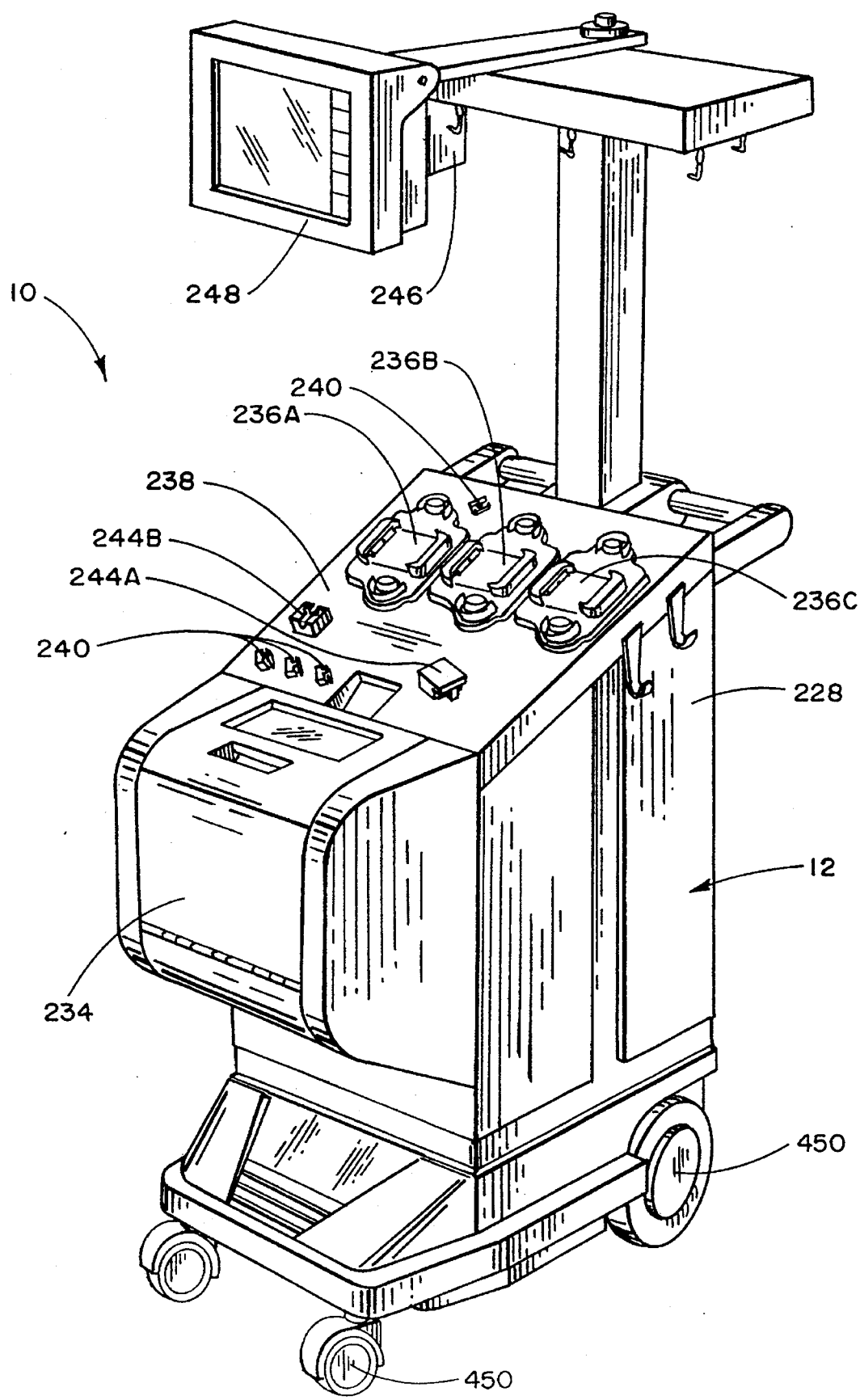
FIG. 1 is a perspective view of a centrifugal assembly that embodies the features of the invention.
Figure 2:
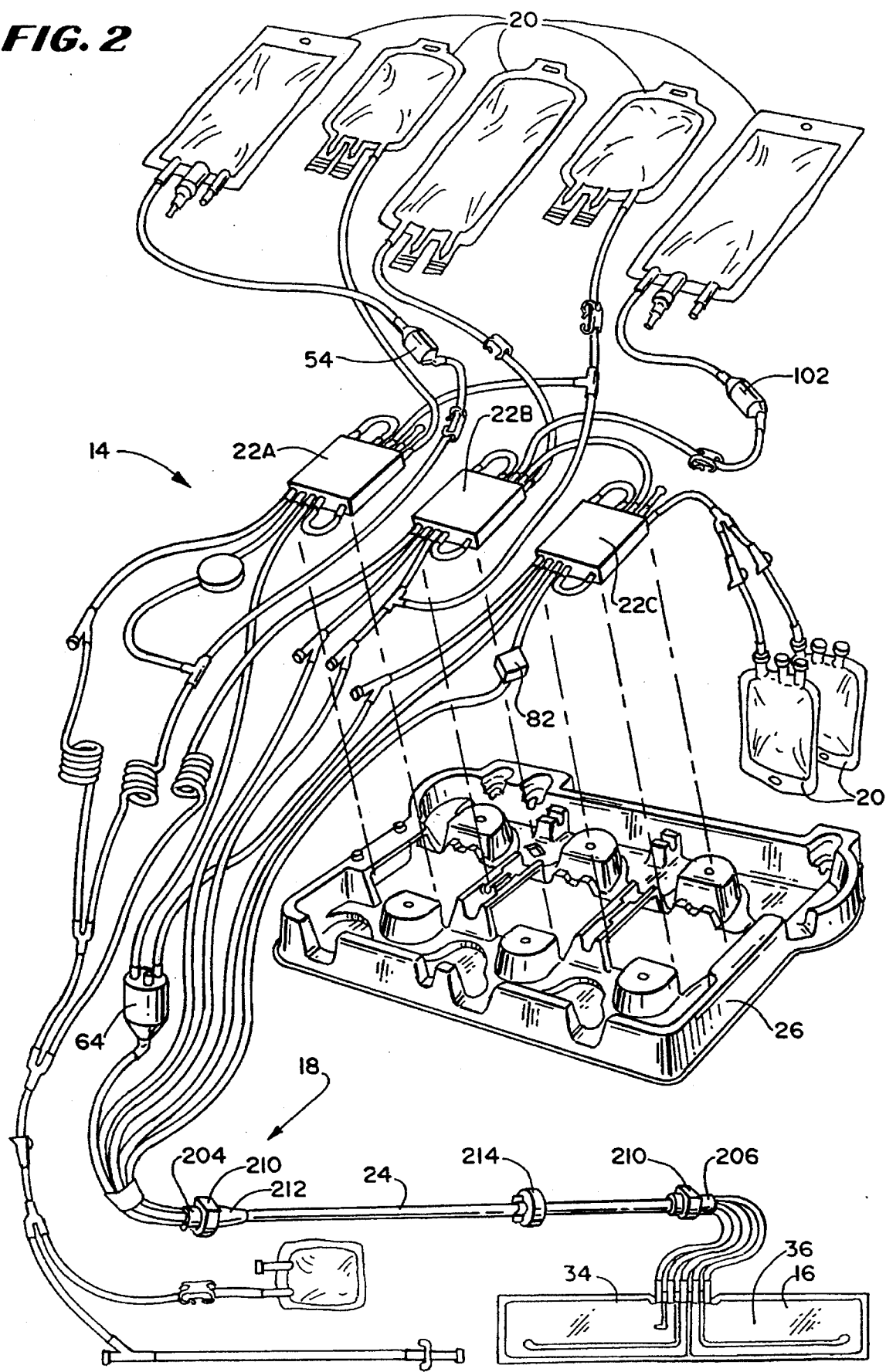
FIG. 2 is an exploded perspective view of a disposable fluid processing assembly usable in association with the centrifuge assembly shown in FIG. 1.
Figure 3:
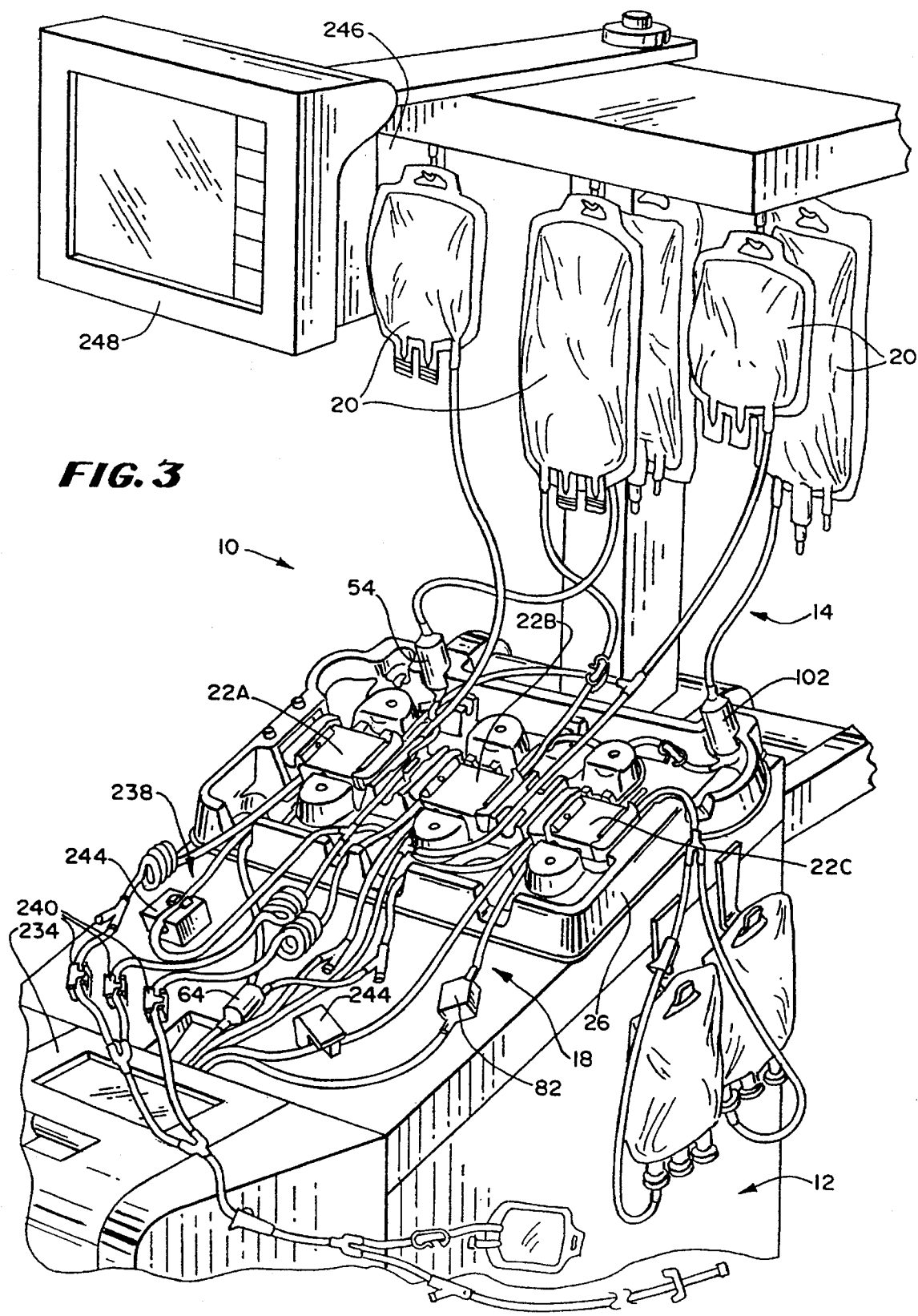
FIG. 3 is a perspective view of a centrifugal processing system that the centrifuge assembly shown in FIG. 1 and the fluid processing assembly shown in FIG. 2 comprise when associated for use.

FIGS. 1 to 3 show a centrifugal processing system 10 that embodies the features of the invention. The system 10 can be used for processing various fluids. The system 10 is particularly well suited for processing whole blood and other suspensions of biological cellular materials. Accordingly, the illustrated embodiment shows the system 10 used for this purpose.

The system 10 includes a centrifuge assembly 12 (see FIG. 1) and a fluid processing assembly 14 (see FIG. 2) used in association with the centrifuge assembly (see FIG. 3).

The centrifuge assembly 12 is intended to be a durable equipment item capable of long term, maintenance free use. The fluid processing assembly 14 is intended to be a single use, disposable item loaded on the centrifuge assembly 12 at time of use (as FIG. 2 shows).

As will be described in greater detail later, the operator removes the fluid processing assembly 14 from the centrifuge assembly 12 upon the completing the procedure and discards it.

I. THE FLUID PROCESSING ASSEMBLY

FIG. 2 shows an exploded view of the disposable processing assembly 14 that is usable in association with the centrifuge assembly.

The assembly 14 includes a processing chamber 16. In use, the centrifuge assembly 12 rotates the processing chamber 16 to centrifugally separate blood components. The construction of the processing chamber 16 can vary. A preferred construction will be described later.

The processing assembly 14 includes an array of flexible tubing that forms a fluid circuit 18. The fluid circuit 18 conveys liquids to and from the processing chamber 16.

The fluid circuit 18 includes a number of containers 20. In use, the containers 20 fit on hangers on the centrifuge assembly 12 (see FIG. 2) to dispense and receive liquids during processing.

The fluid circuit 18 includes one or more in line cassettes 22. FIG. 2 shows three cassettes, designated 22A; 22B; and 22C.

The cassettes 22A/B/C/ serve in association with pump and valve stations on the centrifuge assembly 12 to direct liquid flow among the multiple liquid sources and destinations during a blood processing procedure. The cassettes 22A/B/C centralize the valving and pumping functions to carry out the selected procedure. Further details of these functions will be provided later.

A portion of the fluid circuit 18 leading between the cassettes 22 and the processing chamber 16 is bundled together to form an umbilicus 24. The umbilicus 24 links the rotating parts of the processing assembly 14 (principally the processing chamber 16) with the nonrotating, stationary part of the processing assembly 14 (principally the cassettes 22 and containers 20). The umbilicus 24 links the rotating and stationary parts of the processing assembly 14 without using rotating seals. Further details of a preferred construction for the umbilicus 24 will be provided later.

In the illustrated and preferred embodiment, the fluid circuit 18 preconnects the processing chamber 16, the containers 20, and the cassettes 22. The assembly 14 thereby forms an integral, sterile unit.

In the illustrated and preferred embodiment, the entire processing assembly 14 is packaged for use within an organizer tray 26. The tray 26 holds the processing chamber 16, the containers 20, the cassettes 22, and fluid circuit 18 in an orderly, compact package before use. During use (see FIG. 3), the organizer tray 26 mounts on the centrifuge assembly 12. After processing, the tray 26 receives the processing assembly 14 for disposal.

Further details of the organizer tray 26 and the set up and removal of the processing assembly 14 will be described in greater detail later.

(i) The Fluid Processing Cassette

Each cassette 22A/B/C shares the same construction. FIGS. 4 to 9 show the details of the preferred construction.

As FIGS. 4 and 5 best show, the cassette 22 includes an injection molded body 110 that is compartmentalized by an interior wall 534 to present a front side 112 (see FIG. 5) and a back side 114 (see FIG. 4). For the purposes of description, the front side 112 is the side of the cassette 22 that, in use, faces toward the centrifuge assembly 12.

A flexible diaphragm 116 overlies the front side 112 of the cassette 22. A generally rigid back panel 118 overlies the back side 114 of the cassette.

The cassette 22, interior wall 534, and back panel 118 are preferably made of a rigid medical grade plastic material. The diaphragm 116 is preferably made of a flexible sheet of medical grade plastic. The diaphragm 116 and back panel 118 are sealed about their peripheries to the peripheral edges of the front and back sides 112/114 of the cassette 22.

As FIGS. 4 and 5 also best show, the front and back sides 112/114 of the cassette 22 contain preformed cavities.

On the front side 112 of the cassette 22 (see FIG. 5), the cavities form an array of valve stations $V_N$ and an array of pressure sensing stations $S_N$.

On the back side 114 of the cassette 22 (see FIG. 4), the cavities form an array of channels or paths $F_N$ for conveying liquids.

The valve stations $V_N$ communicate with the liquid paths $F_N$ to interconnect them in a predetermined manner. The sensing stations $S_N$ also communicate with the liquid paths $F_N$ to sense pressures in selected regions.

The number and arrangement of the liquid paths $F_N$, the valve stations $V_N$, and the sensing stations $S_N$ can vary. In the illustrated embodiment, the cassette 22 provides nineteen liquid paths F1 to F19, ten valve stations V1 to V10, and four sensing stations S1 to S4.

The valve and sensing stations V1/V10 and S1/S4 resemble shallow wells open on the front cassette side 112 (see FIG. 5). As FIGS. 7 and 8 best show, upstanding edges 120 rise from the interior wall 534 and peripherally surround the stations V1/V10 and S1/S4.

Figure 8:
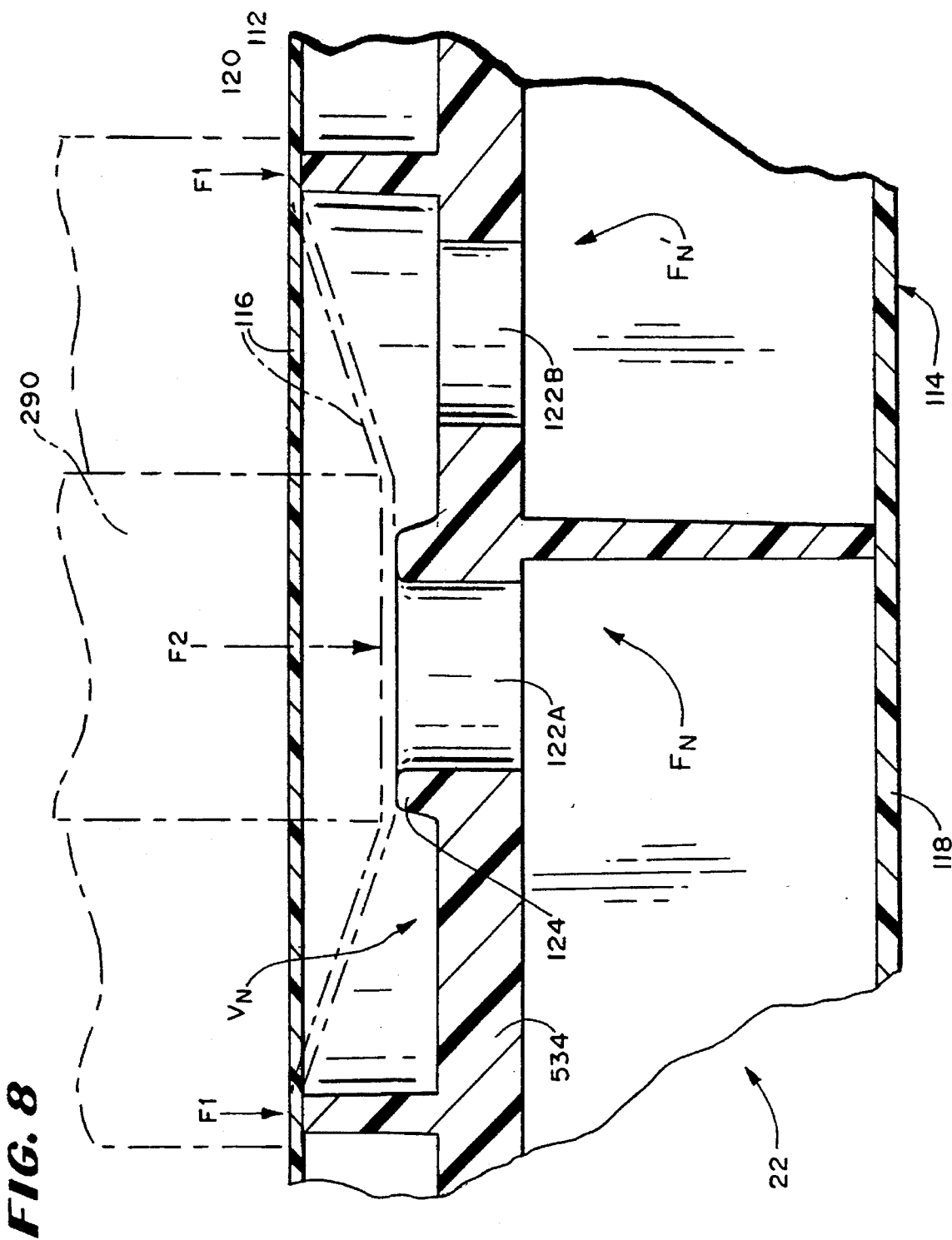
FIG. 8 is an enlarged side section view of a representative valve station located within the cassette body shown in FIG. 4.

The valve stations V1/V10 are closed by the interior wall 534 on the back side 114 of the cassette 22, except that each valve station $V_N$ includes a pair of through holes or ports 122A and 122B in the interior wall 534 (see FIGS. 5 and 8). The ports 122A/B each open into selected different liquid paths $F_N$ and $F_N$, (see FIG. 8) on the back side 114 of the cassette 22. One of the ports 122A is surrounded by a seating ring 124, while the other is not (see FIG. 8).

The sensing stations S1/S4 are likewise closed by the interior wall 534 on the back side 114 of the cassette 22, except that each sensing station $V_N$ includes three through holes or ports 126A/B/C in the interior wall 534 (see FIG. 5). The ports 126A/B/C open into selected liquid paths $F_N$ on the back side 114 of the cassette 24. These ports 126 A/B/C channel liquid flow among the selected liquid paths $F_N$ through the associated sensing station.

Figure 7:
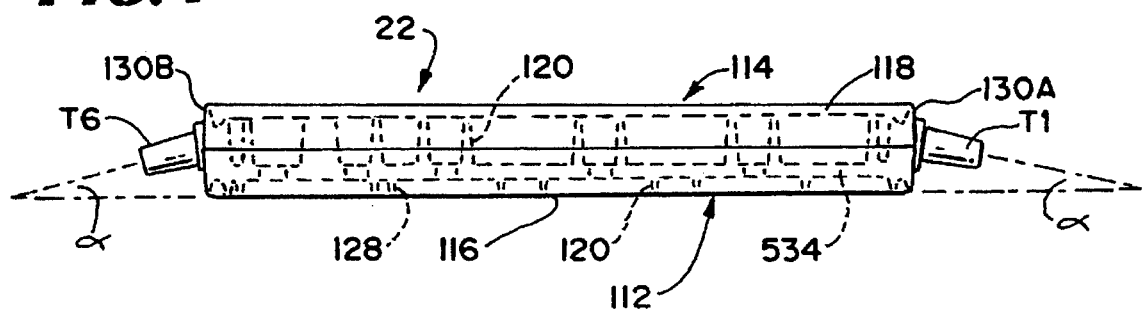
FIG. 7 is a side view of the cassette body, taken generally along line 7—7 in FIG. 6.

As FIGS. 7 and 8 best show, the flexible diaphragm 116 overlying the front side 112 of the cassette 22 is sealed by ultrasonic welding to the upstanding peripheral edges 120 of the valve and sensing stations V1/V10 and S1/S4. This isolates the valve stations V1/V10 and sensing stations S1/S4 from each other and the rest of the system.

Alternatively, the flexible diaphragm 116 can be seated against the upstanding edges 120 by an external positive force applied by the centrifuge assembly 12 against the diaphragm 116 (as shown by the F1-arrows in FIG. 8). The positive force F1, like the ultrasonic weld, peripherally seals the valve and sensing stations V1/V10 and S1/S10.

As shown in phantom lines in FIG. 8, the localized application of additional positive force upon the intermediate region of the diaphragm 116 overlying a valve station V1/V10 (as shown by the F2-arrow in FIG. 7) serves to flex the diaphragm 116 into the valve station. The diaphragm 116 seats against the ring 124 (as shown by phantom lines in FIG. 8) to seal the associated valve port 122A. This closes the valve station to liquid flow.

Upon removal of the force F2, fluid pressure within the valve station and/or the plastic memory of the diaphragm 116 itself unseats the diaphragm 116 from the valve ring 124, opening the valve station to liquid flow.

Preferably, the diameter and depth of the valve stations are selected so that the flexing required to seat the diaphragm 116 does not exceed the elastic limits of the diaphragm material. In this way, the plastic memory of the plastic material alone is sufficient to unseat the diaphragm 116 in the absence of the force F2.

As will be described in greater detail later, in use, the centrifuge assembly 12 selectively applies localized positive force F2 to the diaphragm 116 for closing the valve ports 122A.

As FIGS. 7 and 8 best show, upstanding edges 128 rise from the interior wall 534 and peripherally surround the channels F1/F19, which are open on the back side 114 of the cassette 22.

Figure 6:
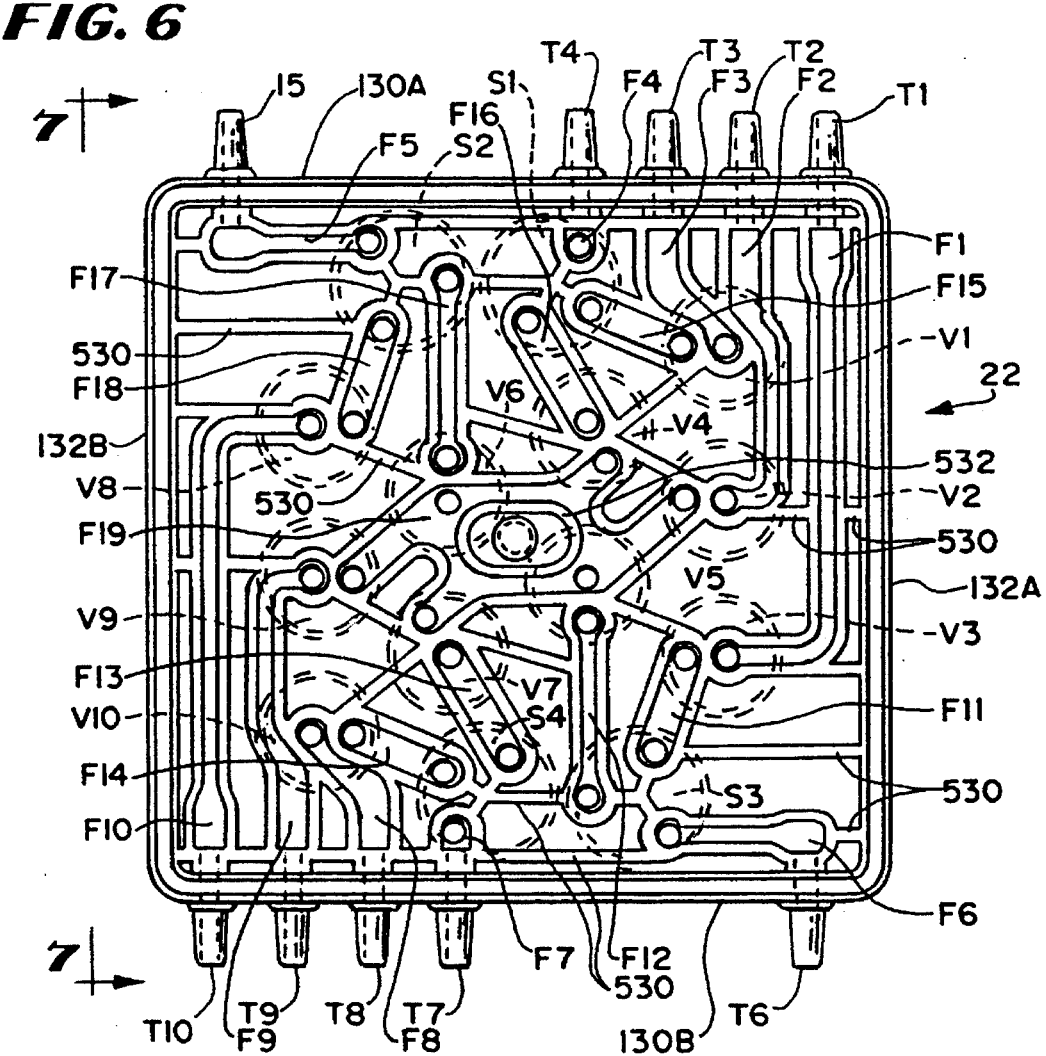
FIG. 6 is a plan view of the fluid circuits and interconnecting valve and sensing stations that the cassette body shown in FIG. 4 carries, looking at the back side of the cassette body.

The liquid paths F1/F19 are closed by the interior wall 534 on the front side 112 of the cassette 22, except for the ports 122A/B of the valve stations V1/V10 and the ports 126A/B/C of the sensing stations S1/S4 (see FIG. 6).

The rigid panel 118 overlying the back side 114 of the cassette 22 is sealed by ultrasonic welding to the upstanding peripheral edges 128, sealing the liquid paths F1/F19 from each other and the rest of the system 10.

As FIG. 6 best shows, ten premolded tube connectors T1 to T10 extend out along opposite side edges 130A/B of the cassette 22. The tube connectors are arranged five on one side edge 130A (T1 to T5) and five on the other side edge 130B (T6 to T10). The other side edges 132A/B of the cassette 22 are free of tube connectors. This ordered orientation of the tube connectors T1/T10 along only two side edges 130A/B of the cassette 22 provides a centralized, compact unit for mounted on the centrifuge assembly 12 (as FIG. 3 shows).

As FIG. 6 shows, along one side edge 130A, the first through fifth tube connectors T1 to T5 communicate with interior liquid paths F1 to F5, respectively. Along the other side edge 130B, the sixth through tenth tube connectors T6 to T10 communicate with interior liquid paths F6 to F10, respectively. These liquid paths F1 to F10 constitute the primary liquid paths of the cassette 22, through which liquid enters or exits the cassette 22.

The remaining interior liquid paths F11 to F19 of the cassette 22 constitute branch paths that link the primary liquid paths F1 to F10 to each other through the valve stations V1 to V10 and sensing stations S1/4.

More particularly, valve station V3 controls liquid flow between primary liquid path F1 and branch fluid path F11. Valve station V2 controls liquid flow between primary liquid path F2 and branch path F19. Valve station V1 controls liquid flow between primary liquid path F3 and branch path F15. Sensing station S1 links primary flow path F4 with branch paths F15 and F16. Sensing station S2 links primary flow path F5 with branch paths F17 and F18.

Similarly, valve station V10 controls liquid flow between primary liquid path F8 and branch fluid path F14. Valve station V9 controls liquid flow between primary liquid path F9 and branch path F19. Valve station V8 controls liquid flow between primary liquid path F10 and branch path F18. Sensing station S3 links primary flow path F6 with branch paths F11 and F12. Sensing station S4 links primary flow path F7 with branch paths F13 and F14.

The branch paths F16, F12, F17, and F13 communicate with branch path F19 through valve stations V4, V5, V6, and V7, respectively.

In this arrangement, branch path F19 serves as a central hub for conveying liquid between the primary fluid paths F1 to F5 on one side 130A of the cassette 22 and the primary fluid paths F6 to F10 on the other side 130B of the cassette 22. The branch paths F16 and F17 feed the central hub F19 from the side 130A of the cassette 22, while the branch paths F12 and F13 feed the central hub F19 from the other side 130B of the cassette 22.

In the illustrated and preferred embodiment (see FIGS. 6 and 9), an upstanding, generally elliptical ridge 532 occupies the midportion of the central hub F19. The ridge 532 helps to channel fluid within the hub F19 to the respective branch paths communicating with it. The ridge 532 also reduces the overall fluid volume of the hub F19 to facilitate liquid conveyance within it.

Also in the illustrated and preferred embodiment, (see FIGS. 6 and 9), an array of internal stiffening elements 530 extend between upstanding edges 128 that form the fluid paths. The internal stiffening elements 530 provide internal rigidity to the cassette structure. This rigidity resists bending or deflection under load. The geometry of the valve stations, sensing stations, and fluid paths thereby remain essentially constant, and are not subject to deformation or alteration during use. The spaced intrastructure of spaced elements 530 stiffen the cassette body without adding significant weight or significantly increasing the amount of plastic material used.

The use of the generally rigid panel 118 overlying the back side 114 of the cassette 22 lends further rigidity to the cassette structure. As will be shown later, the rigid panel 118 also provides a location for securely gripping the cassette 22 during use.

Figure 9:
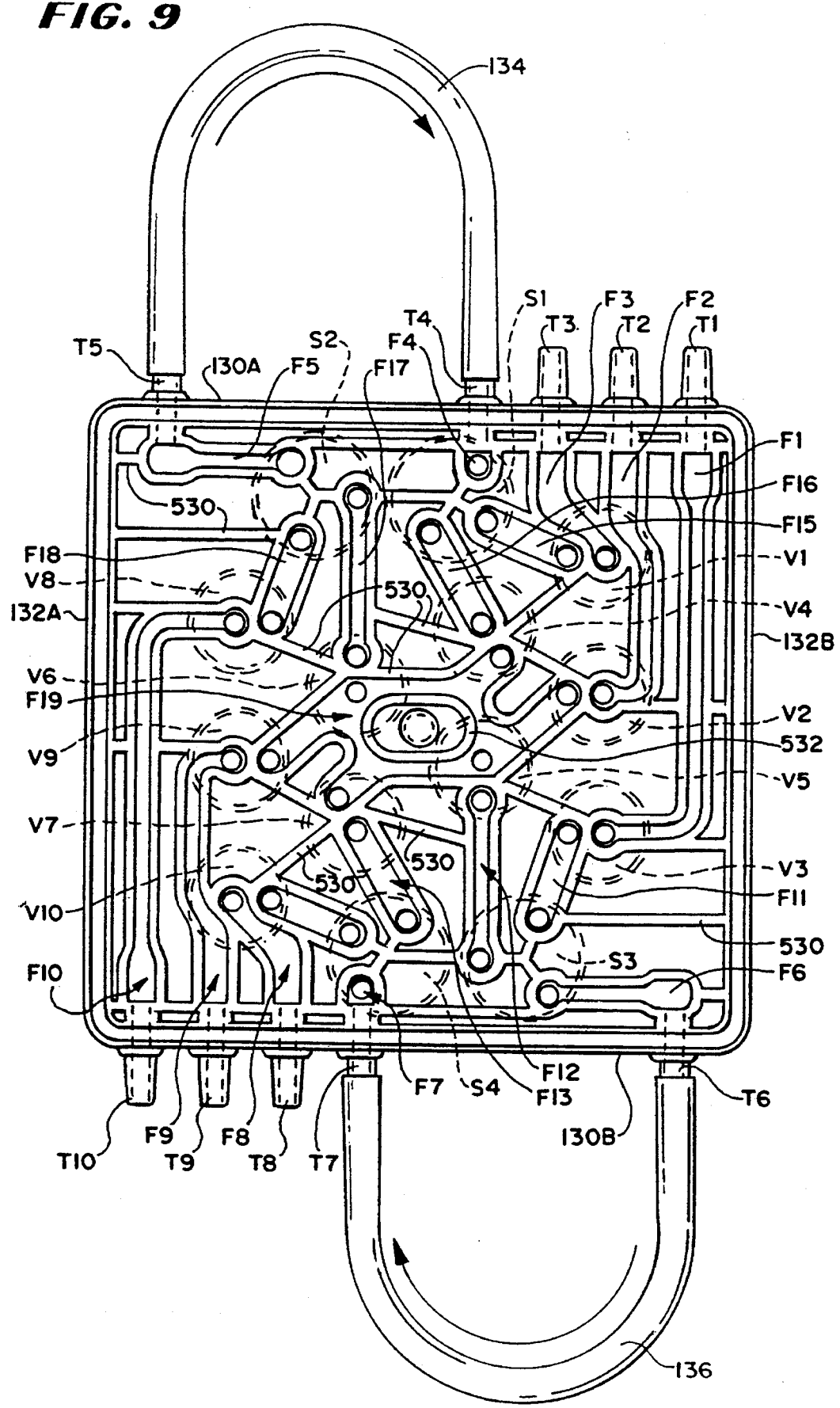
FIG. 9 is a plan view, taken on the back side of the cassette body, of the cassette shown in FIG. 4, with the tubing loops attached and ready for use.

As FIG. 9 shows, external tubing loop 134 connects tube connector T4 with tube connector T5 on the side edge 130A. Likewise, external tubing loop 136 connections tube connector T7 with tube connector T6 on the other side edge 130B. In use, the tube loops 134 and 136 engage peristaltic pump rotors on the centrifuge assembly 12 to convey liquid into the cassette 22 and from the cassette 22.

As FIG. 7 shows, the tube connectors T1/T2 and T9/T10 extend from their respective side edges 130A/B in a sloping direction toward the front side 112 of the cassette 22. In the illustrated and preferred embodiment, the angle $\alpha$ that the sloped tube connector T1/T2 and T9/T10 make with the plane of the front side 112 of the cassette 22 is about 10 degrees. The angled relationship of the tube connectors T1/T2 and T9/T10 facilitates loading the associated tubing loops 134 and 136 on the peristaltic pump rotors. Further details of these aspects of the system 10 will be described later.

The remaining tube connectors T3 to T8 on the cassette 22 are connected with the flexible tubing of the fluid circuit 18.

(ii) The Organizer Tray

Figure 10:
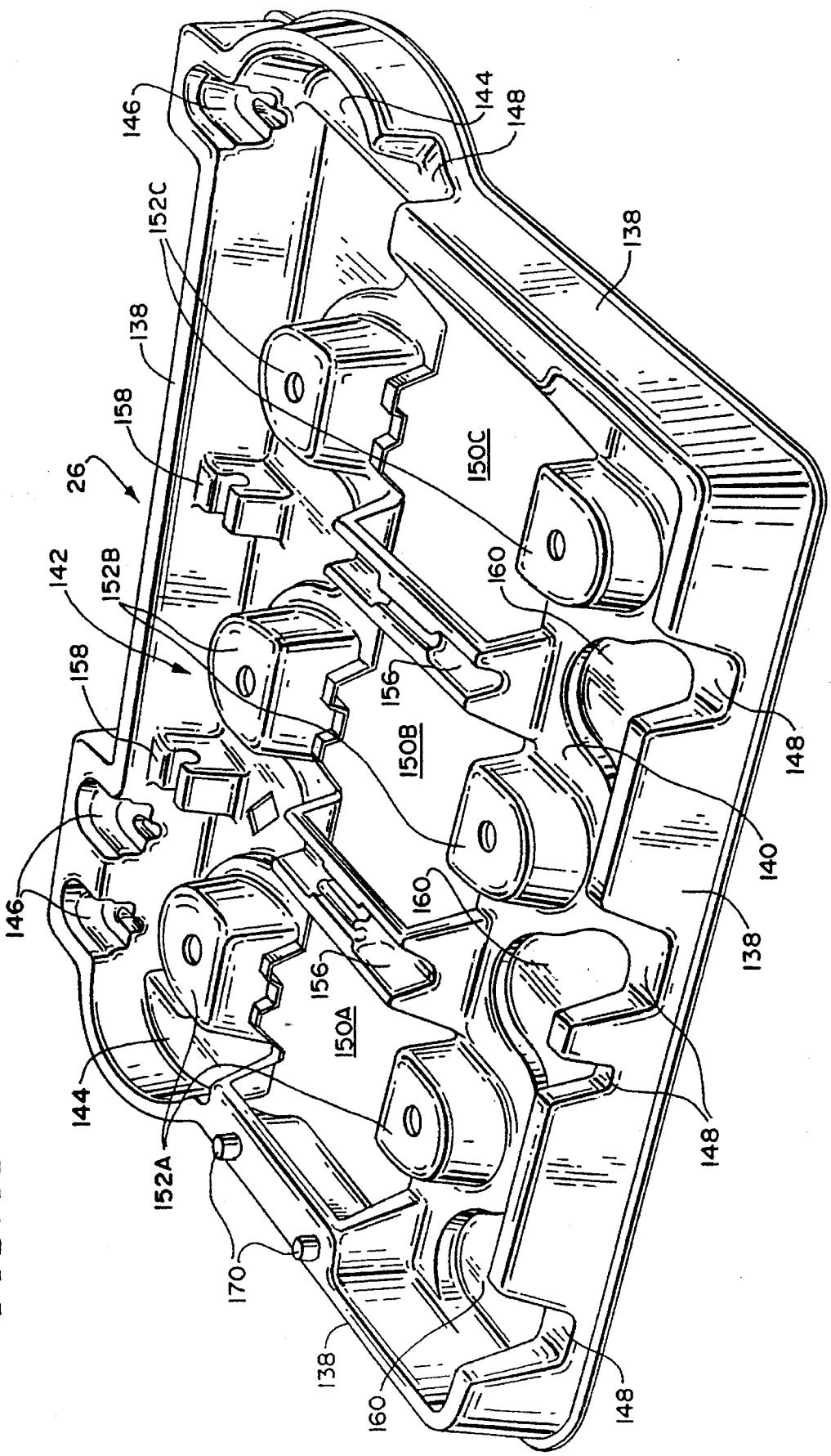
FIG. 10 is a perspective view of the organizer tray that the fluid processing assembly shown in FIG. 2 incorporates.
Figure 11:
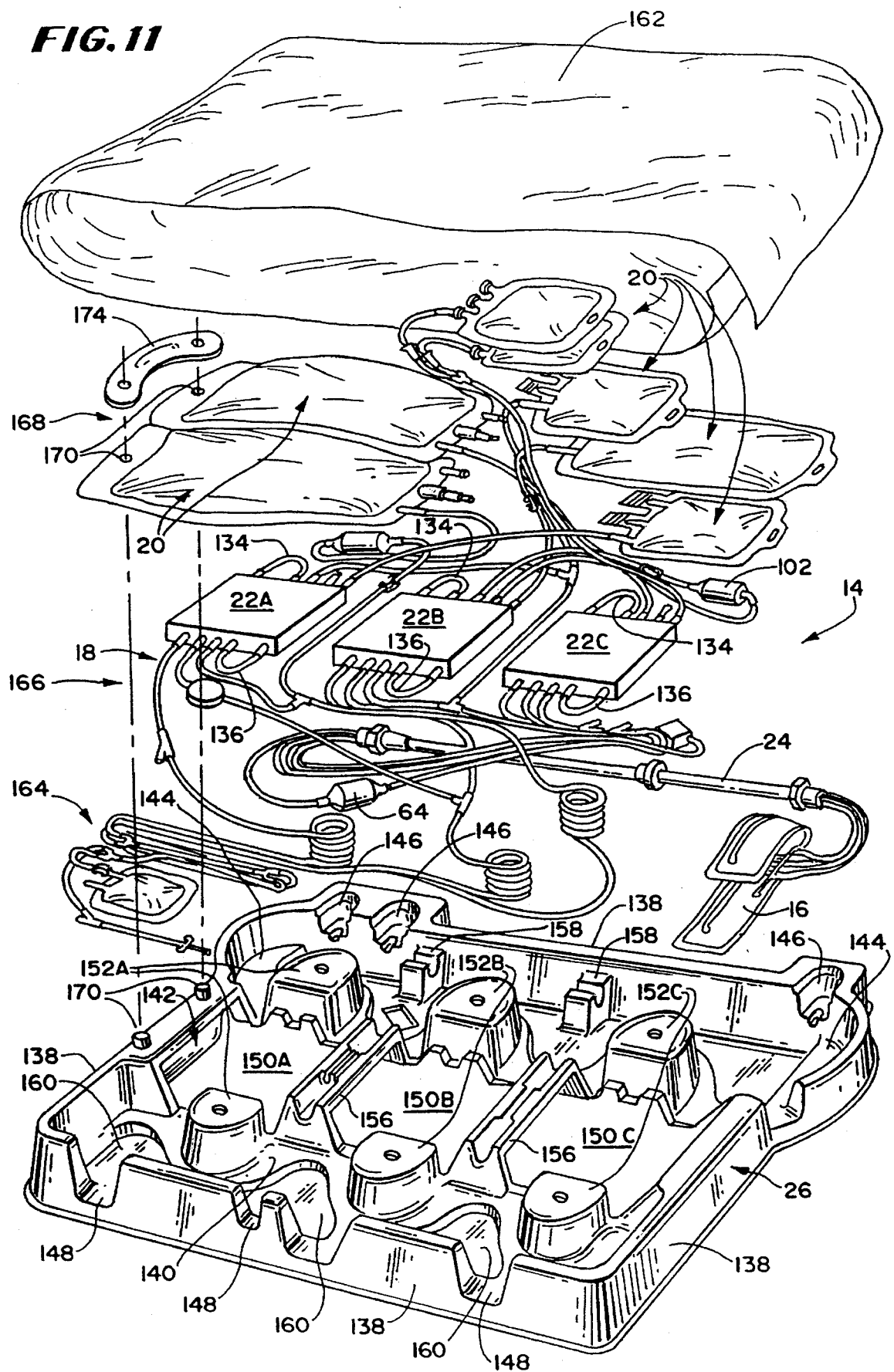
FIG. 11 is an exploded view of the packaging of a representative fluid circuit within the tray shown in FIG. 10.
Figure 12:
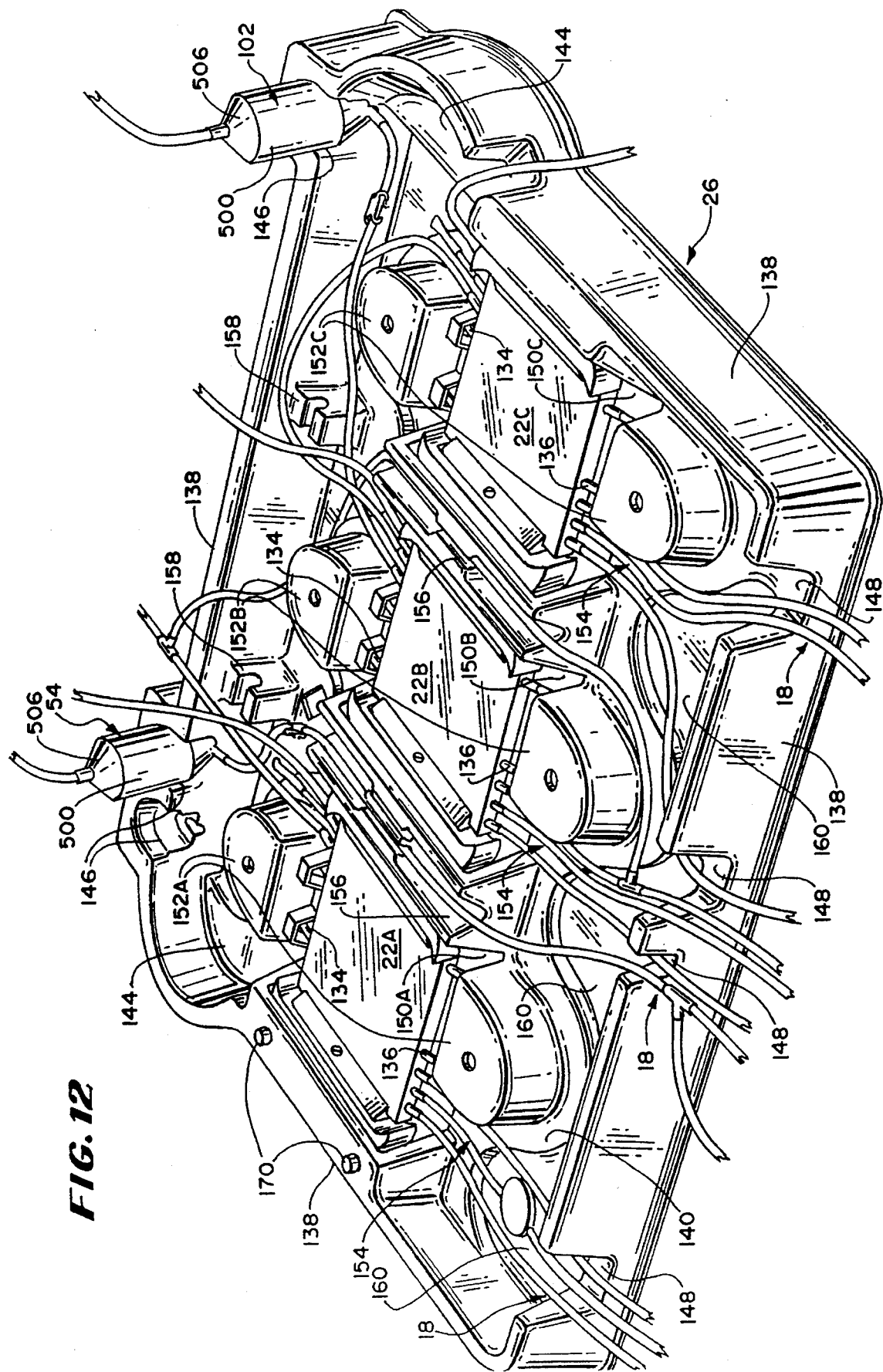
FIG. 12 is a perspective view of the fluid circuit and tray shown in FIG. 11, when unpacked and ready for use.

FIGS. 10 to 12 show the organizer tray 26, in which the fluid circuit 18 is packaged before use.

In the illustrated and preferred embodiment, the tray 26 is made of vacuum formed plastic material. A variety of materials can be used for this purpose; for example, amorphous polyethylene terephthalate (APET), high impact polystyrene (HIPS), polyethylene terephthalate with a glycol modifier (PETG), recycled center layer coextrusions, or paperboard.

The tray 26 includes four side panels 138 and a bottom panel 140 that together form an open interior area 142. The fluid circuit 18 is packed in layers within the open interior area 142 (see FIG. 11).

In the illustrated and preferred embodiment, the side panels 138 include outwardly bowed recesses 144 to accommodate the orderly arrangement of components in the tray 26. The side panels 138 also preferably include preformed brackets or pockets 146 to hold gravity-fed components, like the drip chambers 54 and 102, in a upright, gravity flow position during use (see FIG. 12).

The side panels 138 further include open regions 148 through which portions of the fluid circuit 18 leading to and from the cassettes 22A/B/C pass when the tray is mounted on the centrifuge assembly 12 (see FIG. 12). The bottom panel 140 also preferably includes preformed upstanding brackets 158, which hold the umbilicus 24 in the tray 26 before use.

The bottom panel 140 includes cut-out regions 150 A/B/C (see FIGS. 10 and 11). The cassettes 22 A/B/C fit within these regions 150 A/B/C when packed in the tray 26 (see FIG. 12).

Pairs of upstanding chambers 152 A/B/C are formed at opposite ends of the cut-out regions 150 A/B/C. The tubing loops 134 and 136 attached to each cassette 22 A/B/C extend into the chambers 152 A/B/C, as FIG. 12 shows. As will be described in greater detail later, pump rotors on the centrifuge assembly 12 nest within the chambers 152 A/B/C and engage the tubing loops 134 and 136 during use (as FIG. 2 generally shows).

As FIG. 12 also shows, the tubing loops 134 and 136 inside the chambers 152 A/B/C extend below the top surface of the bottom panel 140. Other tubing lengths 154 attached to the cassettes 22 A/B/C pass over the top surface of the bottom panel 140. The opposed wedging of the tubing loops 134/136 and the tubing lengths 154 above and below the bottom panel 140 suspend the cassettes 22 A/B/C within the regions 150 A/B/C.

Upstanding hollow ridges 156 separate the cutout regions 150 A/B/C. The regions 156 are recessed at their top to accommodate passage of portions of the fluid circuit (as FIG. 12 shows). As will be described in greater detail later, cassette gripping elements on the centrifuge assembly 12 nest within the hollow ridges 156 during use.

Other regions 160 of the bottom panel 140 are cut away to fit over other operative elements carried by the centrifuge assembly 12 (see FIG. 1), like shut-off clamps 240, hemolysis sensor 244A, and air detector 244B.

An outer shrink wrap 162 (see FIG. 11) encloses the tray 26 and the fluid circuit 18 packaged within it.

In the illustrated and preferred embodiment (as FIG. 11 shows), the fluid circuit 18 is packed within the tray 26 in three ordered layers 164, 166, and 168.

The fluid containers 20 occupy within the tray 26 a top layer 168, where they are presented for easy removal by the operator for hanging on the centrifuge assembly 12 (using hanging loops 170 formed in each container 20).

The centrifuge chamber 16, the umbilicus 24, and associated lengths of tubing occupy the next, or middle, layer 166 within the tray 26, where they are presented for removal from the tray 26 and mounting on the centrifuge assembly 12 after the fluid containers 20.

The cassettes 22 A/B/C occupy the next, or bottommost layer 164 in the tray 26, where they present themselves for operative contact with the centrifuge assembly 12.

As FIG. 11 also shows, hanging loops 170 in two of the larger fluid holding containers 22 fit over premolded pins 172 on a tray side panel 138. A bracket 174 makes an interference snap fit over the pins 172 to secure the two containers 22 to the side panel 138. The weight of the fluid holding containers secured to the bracket 174 holds the remainder of the fluid circuit 18 in place within the tray 26 before use.

The tray 26 serves as an organized assembly fixture for the manufacturing plant. It also aids the user in organizing and understanding the relationship of the components for the procedure that is to be run. It gives an organized, purposeful appearance to what otherwise would appear to be a conglomeration of tubing and components.

As will be described in greater detail later, the layering of the fluid circuit 18 within the tray 26 simplifies set up of the processing assembly 14 on the centrifuge assembly 12 at time of use. The tray 26 reduces tubing kinks by allowing for controlled tubing paths, both before and after set up.

During storage, the tray chambers 152 A/B/C serve to cover the tubing loops 134 and 136, at least partially shielding them from contact. During use, the tray chambers 152 A/B/C serve not only as covers for the tubing loops 134 and 136, but for the peristaltic pump rotors themselves. This aspect of the tray 26 will also be described in greater detail later.

It should be appreciated that the tray 26 can be used in association with other types of blood separation elements, and not just the centrifugal processing element shown. For example, the tray 26 can be used in association with a conventional stationary membrane separation element, or with a rotating membrane element like that shown in Fischel U.S. Pat. No. 5,034,135, or with other styles of centrifugal separation elements, like that shown in Schoendorfer U.S. Pat. Nos. 4,776,964 and 4,944,883.

(iii) The Drip Chambers

Figure 13:
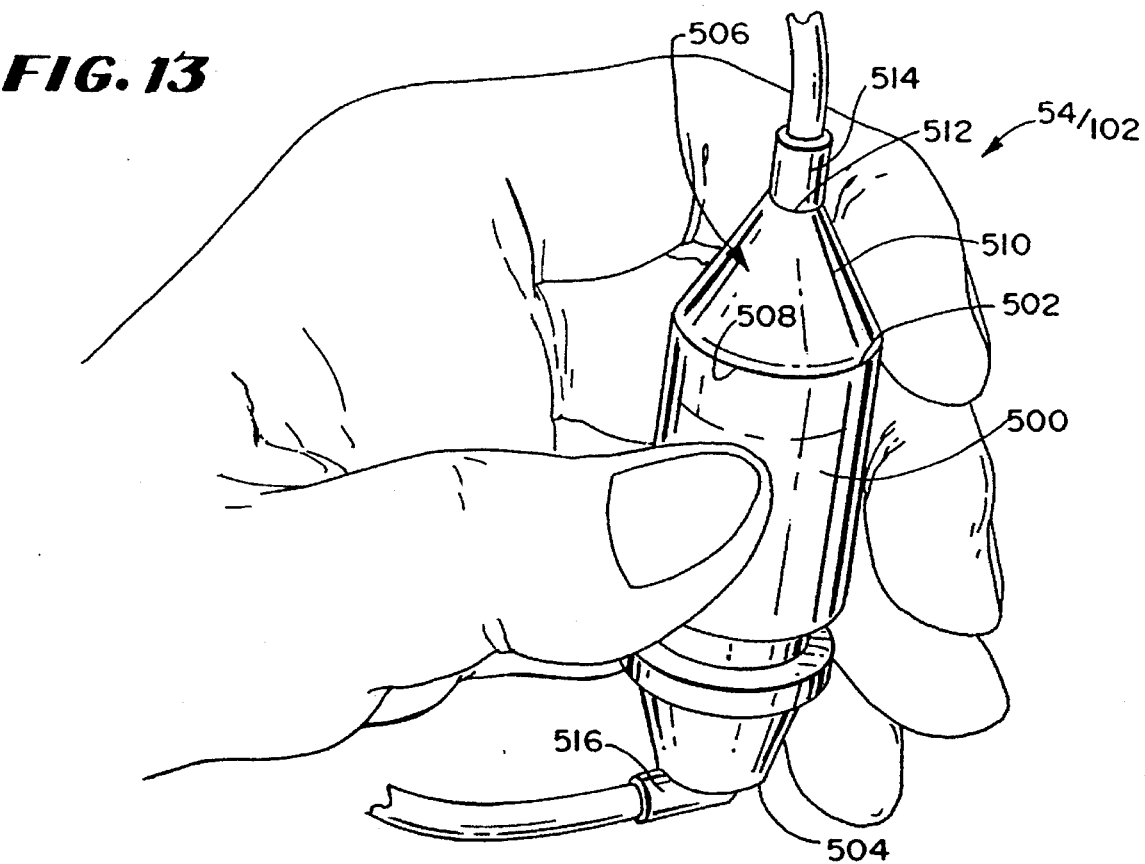
FIG. 13 is an enlarged perspective view of the drip chamber associated with the fluid circuit, held in the hand of the user.

In the illustrated and preferred embodiment (see FIGS. 12 to 14), the drip chambers 54 and 102 associated with the processing assembly 14 are made in their entirety from a non-rigid or "soft", transparent medical grade polyvinyl chloride material. The soft plastic material allows the chambers 54 and 102 to be manually squeezed or "pumped" for air purging and priming (as FIGS. 13 and 14 show).

In the illustrated and preferred embodiment, the soft plastic chambers 54 and 102 are purposely sized small enough to be conveniently handled, yet large enough to provide effective air purging and priming by manual squeezing, even when the drip chambers 54 and 102 are spaced away from an associated solution containers 20 for manufacturing, packaging, and other reasons.

Figure 14:
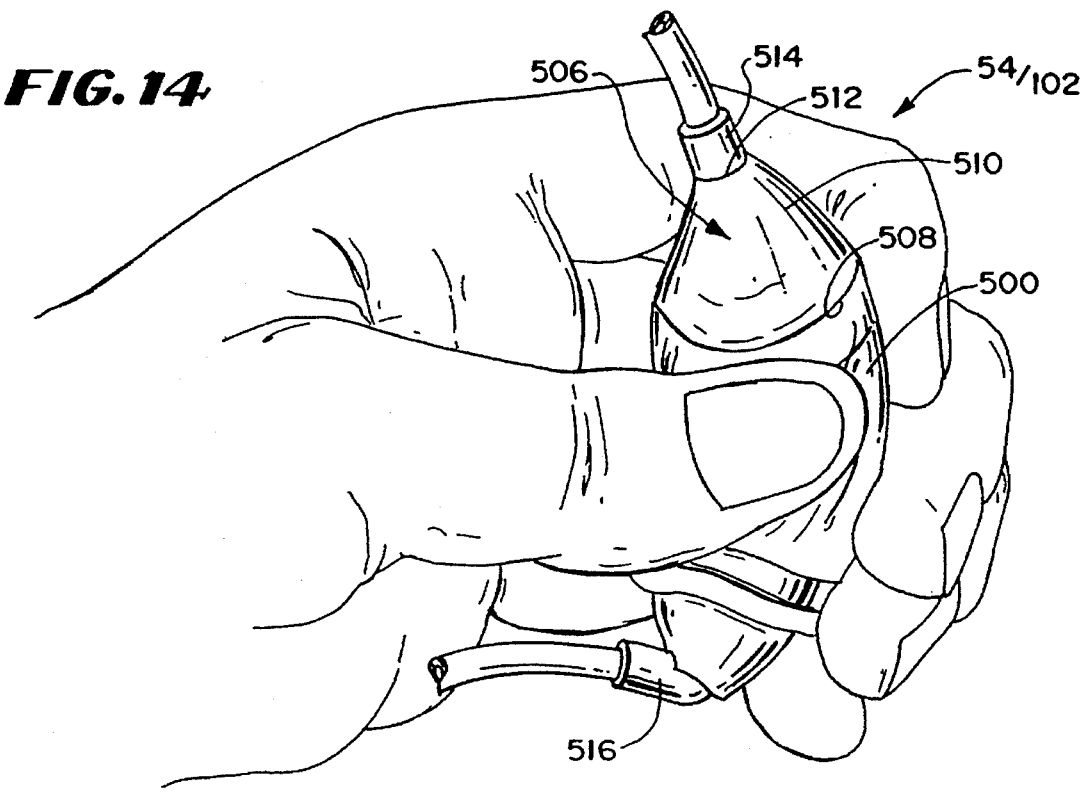
FIG. 14 is an enlarged perspective view of the drip chamber shown in FIG. 13 being squeezed by the user for air purging and priming.

More particularly, in the illustrated and preferred embodiment, the chambers 54 and 102 are sized small enough to be readily gripped in the user's hand (see FIG. 13) and collapsed by a single, vigorous squeeze for air purging and priming (see FIG. 14).

At the same time, the interior volume of each chamber 54 and 102 is sufficiently large, relative to the volume per unit length of the associated tubing, that the volume of the chamber exceeds the interior volume of tubing extending between it and the associated solution container 20. In other words, the chamber volume accommodates placement of the chamber 54 and 102 a reasonable distance away from the associated container 20, without losing the manual priming and air purging capability.

In the preferred embodiment, the processing assembly 14 uses conventional tubing, typically having an internal diameter of about 0.126 inch. In this embodiment, each chamber 54 and 102 preferably measures about 2.5 to 4.5 inches in overall height and about 1.0 to 1.5 inches in diameter. This provides chambers each sized for convenient handling (as FIGS. 13 and 14 show), yet each having a relatively large total internal volume of between about 2.0 cubic inches and about 7.0 cubic inches. In the illustrated embodiment, the interior volume is about 2.0 cubic inches, and the chambers 54 and 102 are located about 18 inches away from their respective solution containers 20.

During manufacturing, the solution containers 20 can be steam sterilized, while the drip chambers 54 and 102 can be separately gamma or EtO sterilized. The containers 20 and chambers 54 and 102 can be packaged away from each other in separate layers within the tray 26, as described above.

During use, despite separation, a single vigorous squeeze purges air from the chambers 54 and 102 and tubing and into the associated solution container 20, thereby priming the chambers 54 and 102 for use.

After priming, the chambers 54 and 102 are conveniently supported within the tray brackets 146 in clear, unimpeded view of the user, with the solution containers 20 suspended above them (as FIG. 3 shows).

In the illustrated and preferred embodiment, the chambers 54 and 102 each includes a main body 500 having an top 502 and a bottom 504. The chambers 54 and 102 also each includes a cap 506 that provides an enhanced field of view of the droplets entering the chambers 54 and 102.

More particularly, the cap 506 has a base 508 and a side wall 510 that converges inward from the base 508 to intersect as a vertex 512 above the main body 500 of each chamber 54 and 102. An inlet port 514 extends from the vertex 512. An outlet port 516 extends from the bottom 504 of the main body 500.

In the illustrated and preferred embodiment (see FIG. 13), the side wall 510 is symmetric with respect to the center of the vertex 512, from which the inlet port 514 extends. The cap 506 thereby takes the structural shape of an inverted cone.

When held in a vertical, gravity feed position for use (as FIG. 12 shows), the tapered side walls of the cap 506 provide an enlarged field of vision for viewing liquid droplets entering the cap 506 from outside the cap 506. The cap 506 allows the user to see liquid droplets dripping into the chambers 54/102 from a normal standing height above the drip chambers 54/102, without having to stoop down, and from a greater distance than conventional drip chambers.

As FIG. 15 shows, the cylindrical wall of a conventional drip chamber 518 (shown in phantom lines in FIG. 15) provide a relatively narrow field of vision 520 that lies generally within a rectangle that extends slightly above and below the plane of the droplet 522. When the conventional drip chamber 518 is suspended the usual distance of about 4 feet above the ground during use, an average person (5 to 6 feet tall) is must stoop down to see the droplet 522 within the field of vision 520. Even then, using a conventional cylindrical drip chamber 518, the droplet 522 can be usually viewed within the field of vision 520 from a distance about only about 3 to 4 feet away.

As FIG. 15 also shows, the angled side wall 510 of the cap 506 significantly expands the field of vision. The expanded field of vision 524 lies within an area bounded by a right triangle whose base 526 extends generally horizontally in the plane of the droplet 522, and whose hypotenuse 528 extends upward from the base at an Angle C, where Angle C= 90°−A, where Angle A represents the degree of taper of the side wall 510. In the illustrated and preferred embodiment, the Angle A is from about 20° to about 40°. The enhanced field of vision 524 that the cap 506 provides significantly extends the horizontal distance at which the droplet 522 can be viewed (as FIG. 15 indicates). The enhanced field of vision 524 also adds significant vertical height above the plane of the droplet 522 from which the droplet 522 can be viewed (as FIG. 15 also indicates).

Using the drip chamber 54/102 of the preferred dimensions described above, with the cap 506 made from conventional soft, transparent medical grade plastic, with a taper Angle A of about 30° and a perpendicular height between the base 508 and the vertex 512 of about 0.81 inch, the droplet 522 can be viewed from a distance of at least 10 feet away under normal lighting conditions. The cap 506 also provides an added viewing height above the droplet of about 2 feet. Thus, with the drip chamber 54/102 suspended 4 feet above the ground, the average person (5 to 6 feet tall) can, under normal lighting conditions, view the droplet from a normal standing position from a distance of at least 10 feet away.

(iv) The Umbilicus

FIGS. 16 and 17 best show the details of the construction of the umbilicus 24.

The umbilicus 24 consolidates the multiple fluid paths leading to and from the blood separation chamber. It provides a continuous, sterile environment for fluids to pass. In construction, the umbilicus 24 is flexible enough to function in the relatively small, compact operating space the centrifuge assembly 12 provides. Still, the umbilicus 24 is durable enough to withstand the significant flexing and torsional stresses imposed by the small, compact spinning environment, where rotation rates up to about 4000 revolutions per minute (RPM) can be encountered.

In the illustrated and preferred embodiment (see FIG. 16), the umbilicus 24 includes a coextruded main body 200 containing five lumens 202. It should be appreciated that the main body 200 could have more or fewer coextruded lumens 202, depending upon the needs of the particular separation process.

In the illustrated and preferred embodiment, the main body 200 is made from HYTREL® 4056 Plastic Material (DuPont). Before extrusion, the material is preferably dried by heat, so that its moisture content is less than about 0.03%. This material withstands high speed flexing over an extended temperature range of between 0° centigrade to 41° centigrade, and higher.

In the illustrated and preferred embodiment (see FIG. 18), the profile design of the extrusion maximizes the cross sectional areas of the lumens 202 while minimizing the outer diameter of the main body 200.

Figure 18:
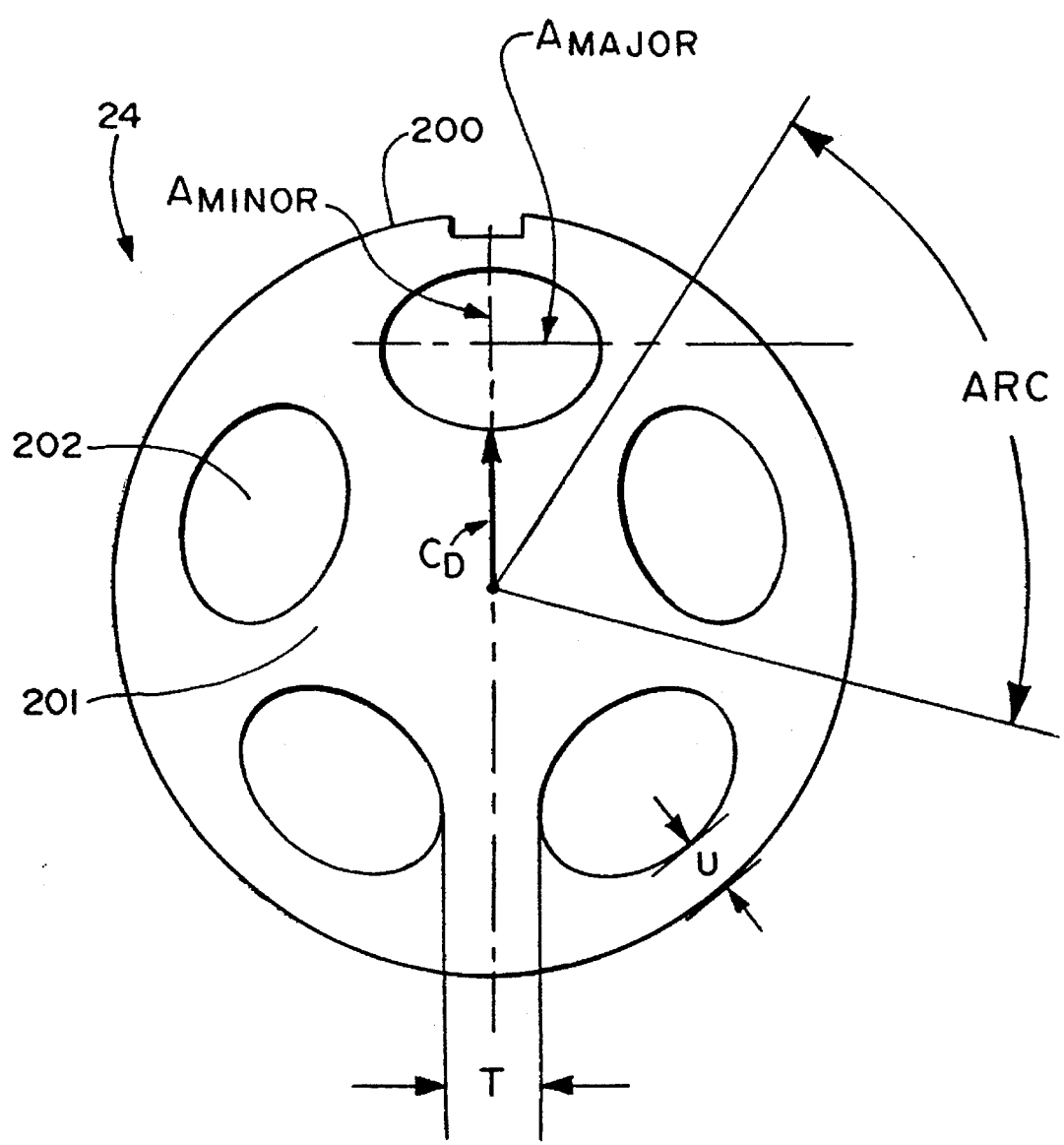
FIG. 18 is an enlarged cross section view of the coextruded body of the umbilicus shown in FIG. 16.

As FIG. 18 shows, the design creates a cylindrical main body 200 having a cylindrical inner core 201 about which the lumens 202 extend in a circumferentially spaced array. The lumens 202 are elliptical in shape. The elliptical shape of the lumens 202 shown in FIG. 18 maximizes the cross sectional area of the lumens 202 for a desired flow rate capability. The elliptical shape of the lumens 202 provides this benefit without enlarging the outer diameter of the main body 200, and thereby increasing its centrifugal mass, as an array of circular lumens of comparable cross sectional area would.

In the illustrated and preferred embodiment, the main body 200 has an outer diameter of about 0.333 inch. The elliptical lumens 202 are circumferentially spaced along the periphery of the main body by an arc (designated ARC in FIG. 18) about 72°. Each lumen 202 measures about 0.108 inch along its major axis (designated $A_{Major}$ in FIG. 18) and about 0.65 along its minor axis (designated $A_{Minor}$ in FIG. 18).

The inner core 201 of the main body 200 forms a circle having a diameter (designated $C_D$ in FIG. 18) of about 0.155 inch. This provides a wall thickness (designated T in FIG. 18) between lumens of about 0.055 inch. It is believed that, below 0.020 inch, the integrity of the coextrusion becomes problematic and becomes subject to twisting and failure.

The space between the outer edge of each lumen 202 and the outer surface of the main body 200 (designated U in FIG. 18) is about 0.23 inch. It is believed that, below 0.15 inch, the integrity of the coextrusion again becomes problematic and subject to failure when twisted.

The minimized outer diameter of the profile reduces the centrifugal forces generated when the umbilicus 24 is spun to reduce the overall stresses encountered. The elliptical configuration of the lumens 202 maximizes fluid flow capacity. The circumferential placement of the lumens 202 within the main body 200 maximizes the physical strength and stress resistance of the overall umbilicus structure. As FIG. 16 best shows, an upper support block 204 and a lower support block 206 are secured, respectively, to opposite ends of the umbilicus body 200.

Each support block 204 and 206 is preferably made of a Hytrel® 8122 Plastic Material (DuPont). The blocks 204 and 206 injection over-molded around the main umbilicus body 200 and include formed lumens 208 which communicate with the lumens 202 of the umbilicus body 200. The heat of the injection over-molding process physically bonds the two Hytrel® Plastic materials together. The support blocks thereby prove a secure, leak proof, integral fluid connection for each fluid path through the umbilicus 24.

The Hytrel® 8122 Plastic Material of the blocks 204 and 206 has a lesser modulus and is therefore softer and more flexible than the Hytrel® 4056 Material of the main body 200. The Hytrel® Plastic also can be solvent bonded to medical grade polyvinyl chloride tubing. The tubing of the fluid circuit 18 can thereby be secured by solvent bonding within the lumens 208 of the support blocks 204 and 206.

Each support block 204 and 206 preferably includes an integral, molded flange 210. Each flange 210 has is own predetermined shape, which can be the same or different for the two flanges. In the illustrated embodiment, each flange 210 is generally D-shaped.

The upper support block further includes a tapered sleeve 212. In use, the sleeve 212 acts as a strain relief element for the umbilicus 24. The lower support block 206 is free if a strain relief element. As will be shown later, the sole strain relief sleeve 212 distributes stresses so that localized stresses are minimized.

In the illustrated and preferred embodiment, a solvent (such as methylene chloride or methyl ethyl ketone) is also applied to the opposite ends of the Hytrel® 4056 Plastic Material of the umbilicus body 200 before the Hytrel® 8122 Plastic Material is over-molded to form the support blocks 204 and 206 and associated flanges 210 and strain relief sleeve 212. It has been observed that the application of solvent before over-molding increases the surface energy of the connection site, significantly increasing the strength of the connection between the block members 204 and 206 and the umbilicus body 200.

Instead of using a solvent, other methodologies can be used to strengthen the connection between the block members 204 and 206 (and associated flanges 210 and sleeve 212) and the umbilicus body 200. For example, the connection can be strengthened by etching the exterior of the main body 200 to increase the surface energy of the connection site. The etching can be accomplished by corona discharge or plasma discharge treatment.

Without increasing the surface energy of the connection site before over-molding, the block members 204/206 and associated flanges 210/sleeve 212 are observed to de-laminate and peel away from the umbilicus body 200 when exposed to the stresses imposed during centrifugation. Premature failure of the overall umbilicus structure results.

A thrust bearing member 214 is secured about the coextruded main body 200 at a predetermined distance from the lower support block 206.

The thrust bearing member 214 (see FIG. 17, also) comprises an outer annular body 216 and an inner annular body 218. Ball bearings 220 support the inner body 218 for rotation within the outer body 216. The inner body includes a center hub 222 through which the umbilicus main body 200 passes to mount the thrust bearing member 214 on the umbilicus main body 200.

The hub 222 includes a rear collar 224 that projects outward beyond the inner/outer body assemblage. A clip 226 fastens the collar 224 to the umbilicus body 200, thereby securing the thrust bearing member 214 to the umbilicus body 200. The collar 224 isolates the umbilicus body 200 from direct surface contact with the clip 226. The snug securing force can be applied by the clip 226 (via the collar 224) without significantly occluding or flattening the interior lumens 202 in the umbilicus body 200.

Alternatively, instead of an integral collar 224, a stop (not shown) can be attached by potting or over-molding about the umbilicus body 200 using a polyurethane compound. The stop can also be physically secured at a desired location on the umbilicus body 200. In this arrangement, the thrust bearing 214 itself is not attached at a fixed location on the body 200, but slides along the umbilicus body 200 and abuts against the stop during use.

The thrust bearing member 214 can be made from various materials. In the illustrated and preferred embodiment, the inner and outer bodies 216 and 218 are made from polyamide material like nylon-6,6. Other materials like polytetrafluoroethylene (PTFE) or acetal can also be used. The ball bearings 220 are made from hardened stainless steel.

(v) Processing Assemblies for Platelet Collection

Figure 19:
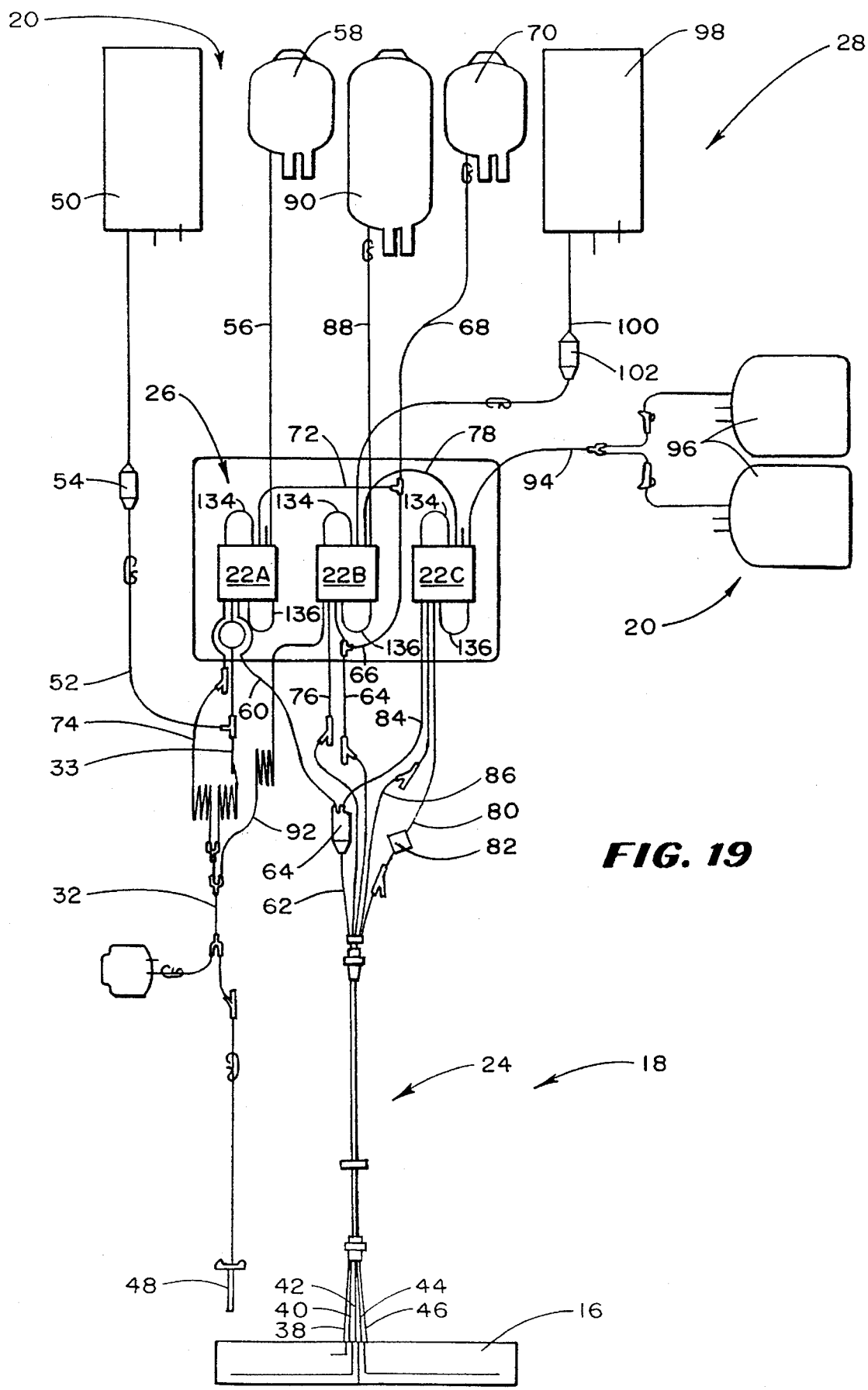
FIG. 19 is a diagrammatic view of a representative single needle fluid processing assembly usable in association with the centrifuge assembly shown in FIG. 1.
Figure 20:
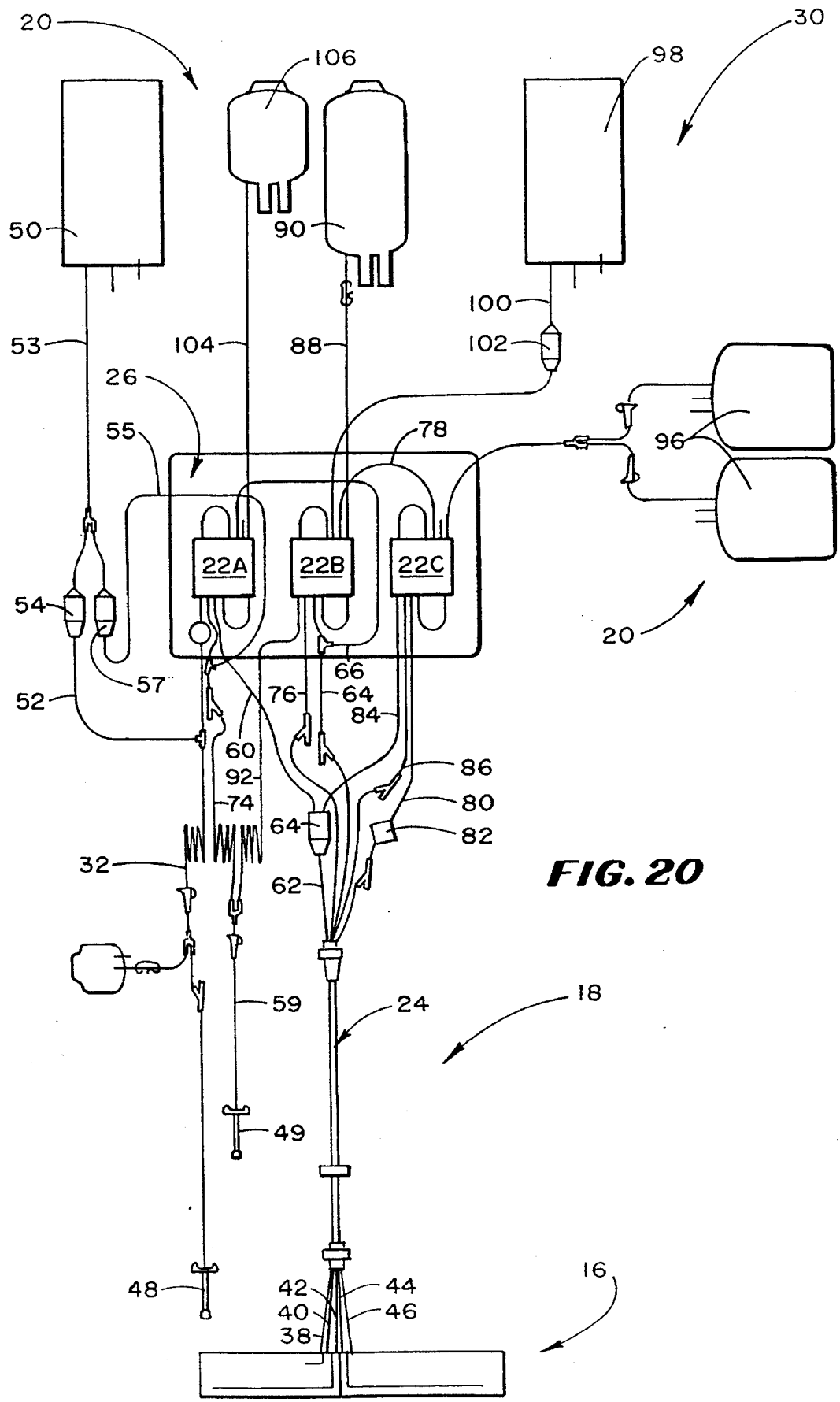
FIG. 20 is a diagrammatic view of a representative double needle fluid processing assembly usable in association with the centrifuge assembly shown in FIG. 1.

The processing assembly 14 as just described can be configured to accomplish diverse types of processing techniques. FIGS. 19 and 20 show representative disposable systems for accomplishing continuous platelet collection. FIG. 19 shows a single needle platelet collection system 28 (FIGS. 2; 3; and 11 also show the single needle system 28 in association with the tray 26 and centrifuge assembly 12). FIG. 20 shows a two needle platelet collection system 30.

Each system 28 and 30 includes the processing chamber 16 and containers 20 interconnected by the fluid circuit 18 carried by the organizer tray 26. The fluid circuit 18 for each system 28 and 30 includes the three centralized pumping and valving cassettes, identified as 22A; 22B; and 22C. The umbilicus 24 links the rotating and non-rotating components in each system 28 and 30.

Other elements common to both systems 28 and 30 are also assigned the same reference number in the descriptions that follow.

(A) The Processing Chamber

The processing chamber 16 can be variously constructed. For example, it can be constructed like the double bag processing chambers shown in Cullis et al. U.S. Pat. No. 4,146,172.

In the illustrated and preferred embodiment, the processing chamber 16 in each system 28 and 30 is formed as an elongated flexible tube made of a flexible, biocompatible plastic material such as plasticized medical grade polyvinyl chloride. The chamber 16 includes a first stage compartment 34 and a second stage compartment 36.

The first stage compartment 34 receives whole blood (WB). When subjected to centrifugal forces, the first stage compartment 34 separates the WB into red blood cells (RBC) and platelet rich plasma (PRP).

The second stage compartment 36 receives PRP from the first stage compartment 32. When subjected to centrifugal forces, the second stage compartment 36 separates the PRP into concentrated platelets (PC) and platelet-poor plasma (PPP).

Specific details of the construction of the processing chamber 16 are not essential to an understanding of the invention and can be found in copending U.S. patent application Ser. No. 07/965,074, filed Oct. 22, 1992 and entitled "Enhanced Yield Blood Processing Systems and Methods Establishing Vortex Flow Conditions," which is incorporated herein by reference.

In FIGS. 19 and 20, the fluid circuit 18 includes five tubing branches 38/40/42/44/46 that communicate directly with the processing chamber 16. Three tubing branches 38/40/42 serve the first stage compartment 34. Two tubing branches 44/46 serve the second stage compartment 36.

The tubing branch 40 carries WB into the first stage compartment 34 for processing. The tubing branch 38 carries separated PRP from the first stage compartment 34. The tubing branch third port 42 carries separated RBC from the first stage compartment 34.

The tubing branch 46 carries PRP separated in the first compartment 34 into the second compartment 36 for further processing. The tubing branch 44 carries separated PPP from the second stage compartment 36. The separated PC remains in the second stage compartment 36 for later resuspension and collection, as will be explained later.

(B) The Single Needle Fluid Circuit

In the illustrated and preferred configuration shown in FIG. 19, the cassettes 22A/B/C serve to segregate the flow paths of various categories of fluids and blood components from each other during processing.

The cassette 22A principally handles the flow of fluids containing red blood cells, either as WB or as RBC. The cassette 22B principally handles the flow of cellular-free fluids, either as PPP or anticoagulant. The cassette 22C principally handles the flow of fluids containing platelets, either as PRP or PC.

More particularly, the fluid circuit 18 for the single needle system 28 (see FIG. 19) includes a tubing branch 32 that carries a phlebotomy needle 48 for drawing WB from a donor. A tubing branch 33 joins the tubing branch 32 and leads to the cassette 22A. A tubing branch 100 carries an anticoagulant solution from a container 98 into the tubing branch cassette 22B (via a drip chamber 102). The anticoagulant flows from cassette 22B through tubing branch 92 for addition to the WB before processing. A tubing branch 56 leads from the cassette 22A to convey anti-coagulated WB to a reservoir container 58.

Another tubing branch 60 leads from the cassette 22A to convey anti-coagulated WB into the umbilicus 24 via a drip chamber 64 and tubing branch 62. The umbilicus 24 joins tubing branch 40, which carries the anti-coagulated WB into the first stage chamber 34 for separation into RBC and PRP.

The tubing branch 42 carries the separated RBC from the first stage chamber 34 through the umbilicus 24. The umbilicus 24 joins the tubing branches 64, 66, and 68, which lead to a reservoir container 70 for RBC.

A tubing branch 72 joins tubing branch 68 to carry RBC from the reservoir container 70 to the cassette 22A. The tubing branch 74 leads from the cassette 22A to carry RBC to the tubing branch 32, which leads to the phlebotomy needle 48.

The cassette 22A thereby directs the flow of anti-coagulated WB from the donor into the first stage compartment 34. The cassette 22A also directs the flow of separated RBC from the first stage compartment 34 back to the donor.

These flows are sequenced to proceed in two cycles. One cycle draws WB from the donor, while the other returns RBC to the donor.

In the draw cycle, the single needle system 28 collects through the cassette 22A a predetermined volume of anti-coagulated WB in the reservoir container 58 (through tubing branches 32/33/56), while conveying the rest of the anti-coagulated WB continuously to the first stage compartment 34 for separation (through tubing branches 32/33/60/62/40). During the draw cycle, the system 28 also continuously collects the separated RBC in the reservoir container 70 (through tubing branches 42/64/66/68).

In the return cycle, the system 28 continuously conveys through the cassette 22A anti-coagulated WB from the reservoir container 58 into the first stage compartment 34 for separation (through tubing branches 56/60/62/40). At the same time, the system 28 returns through the cassette 22A the RBC collected in the reservoir container 70 to the donor (through tubing branches 68/72/74/32) as well as those RBC being then separated in the first stage compartment 34 (via tubing branches 64 and 66, joining tubing branch 68).

This two cycle sequence through the cassette 22A assures that anti-coagulated WB is continuously conveyed to the first stage compartment for separation, either from the donor (during the draw cycle) or from the WB reservoir container 58 (during the return cycle).

The tubing branch 86 carries separated PRP from the first stage compartment 34 through the umbilicus 24 to the cassette 22C.

A portion of the PRP is conveyed from the cassette 22C through tubing branch 80. Tubing branch 80 leads to the umbilicus 24, which joins tubing branch 46, which takes the PRP into the second stage compartment 36 for further separation into PPP and PC.

In the illustrated and preferred embodiment, the tubing branch 80 carries an in line filter 82. The filter 82 removes leukocytes from the PRP before it enters the second stage compartment 36 for separation.

Another portion of the PRP is conveyed from the cassette 22C through tubing branch 84 to the drip chamber 64, where it mixes with the anticoagulated WB being conveyed into the first stage compartment 34. This recirculation of PRP improves the yield of platelets.

Further details of the in line filtration and recirculation of PRP are not essential to an understanding of the invention and are disclosed in patent application Ser. No. 08/097,454, filed Jul. 26, 1993, and entitled "Systems and Methods for Reducing the Number of Leukocytes in Cellular Products Like Platelets Harvested for Therapeutic Purposes."

The tubing branch 44 carries PPP from the second stage compartment 36 through the umbilicus 24 and to tubing branch 76, which leads to the cassette 22B. Tubing branch 88 carries the PPP from the cassette 22B to a reservoir container 90.

During processing, a portion of the PPP collected in the reservoir container 90 is returned to the donor with the RBC during the return cycle. This portion of PPP is conveyed from the reservoir container 90 through tubing branch 66 via the cassette 22B to tubing branch 72, which joins the tubing branch 33 via cassette 22A. At the same time, PPP then being separated in the second stage compartment 36 is returned to the donor through tubing branches 85 and 76 to the tubing branch 66 via the cassette 22B.

Another portion of the PPP collected in the reservoir container 90 is used to resuspend PC in the second stage compartment 36 after separation ends. This portion of PPP is conveyed from the reservoir container 90 through tubing branch 88 via the cassette 22B, back through tubing branch 76, the umbilicus 24, and tubing branch 44 into the second stage compartment 36. There, the PPP resuspends PC accumulated in the compartment 36. The tubing branch 46 conveys resuspended PC from the compartment 36, through the umbilicus 24 to tubing branch 86, which joins the cassette 22C. Tubing branch 94 conveys resuspended PC from the cassette 22C to collection containers 96.

Other portions of the PPP collected in the reservoir container 90 can also be used for additional processing purposes. For example, the PPP (which carries most of the anticoagulant added during processing) can serve as an anti-coagulated "keep open" fluid, to keep the phlebotomy needle 48 open during lulls in processing. The PPP can also be used as a "final flush" fluid, to purge the tubing branches after processing.

The PPP remaining in the reservoir container 90 after processing can be stored for therapeutic purposes.

Further details of the collection and use of PPP as a processing aid are not essential to an understanding of the invention and are disclosed in patent application Ser. No. 08/097,967, filed Jul. 26, 1993 and entitled "Systems and Methods for On Line Collection of Cellular Blood Components that Assure Donor Comfort" and Ser. No. 08/097,293, filed Jul. 26, 1993, and entitled "Systems and Methods for On Line Collecting and Resuspending Cellular Blood Products Like Platelet Concentrate."

Container 50 holds a saline priming solution, which is used to purge air from the system 28 before processing. Tubing branch 52 carries the saline from the container 50 (via the drip chamber 54) to cassette 22A. The saline is conveyed from the cassette 22A into the processing chamber 16 via tubing branches 60 and 62, and from there to the rest of the system 28 along the tubing branches already described.

(C) The Double Needle Fluid Circuit

In the illustrated and preferred configuration shown in FIG. 20, the cassettes 22A/B/C also serve to segregate the flow paths of various categories of fluids and blood components from each other during processing.

As in the FIG. 19 embodiment, the cassette 22A principally handles the flow of fluids containing red blood cells, either as WB or as RBC. The cassette 22B principally handles the flow of cellular-free fluids, either as PPP or anticoagulant. The cassette 22C principally handles the flow of fluids containing platelets, either as PRP or PC.

More particularly, the fluid circuit 18 for the single needle system 30 (see FIG. 20) includes a tubing branch 59 that carries a phlebotomy needle 49 for drawing WB from a donor. Tubing branches 100 carries an anticoagulant solution from a container 98 into the tubing branch 92 (via a drip chamber 102 and cassette 22B) for addition to the WB before processing.

The WB is drawn through needle 49 from the donor and conveyed to the cassette 22A through tubing 59 and 74. Another tubing branch 60 leads from the cassette 22A to convey anti-coagulated WB into the umbilicus 24 via a drip chamber 64 and tubing branch 62. The umbilicus 24 joins tubing branch 40, which carries the anti-coagulated WB into the first stage chamber 34 for separation into RBC and PRP.

The tubing branch 42 carries the separated RBC from the first stage chamber 34 through the umbilicus 24. The umbilicus 24 joins the tubing branches 64 and 66 to carry RBC to the cassette 22A. The tubing branch 32 leads from the cassette 22A to carry RBC to a second phlebotomy needle 48.

In FIG. 20, the cassette 22A thereby directs the flow of anti-coagulated WB from the donor from the first needle 49 into the first stage compartment 34. The cassette 22A also directs the flow of separated RBC from the first stage compartment 34 back to the donor through the second needle 48. Unlike the sequenced draw and return cycles in the single needle system 28, the incoming and outgoing flows through the two needles 49 and 48 occur simultaneously in the system 30. As in the single needle system 28, anti-coagulated WB is continuously conveyed to the first stage compartment for separation in the double needle system 30.

In the double needle system 30, the tubing branch 86 carries separated PRP from the first stage compartment 34 through the umbilicus 24 to the cassette 22C.

A portion of the PRP is likewise conveyed from the cassette 22C through tubing branch 80. Tubing branch 80 leads to the umbilicus 24, which joins tubing branch 46, which takes the PRP into the second stage compartment 36 for further separation into PPP and PC.

In the illustrated and preferred embodiment, the tubing branch 80 also carries an in line filter 82. The filter 82 removes leukocytes from the PRP before it enters the second stage compartment 36 for separation.

Another portion of the PRP is conveyed from the cassette 22C through tubing branch 84 to the drip chamber 64, where it mixes with the anticoagulated WB being conveyed into the first stage compartment 34.

The tubing branch 44 carries PPP from the second stage compartment 36 through the umbilicus 24 and to tubing branch 76, which leads to the cassette 22B. Tubing branch 88 carries the PPP from the cassette 22B to a reservoir container 90.

As in the single needle system 28, a portion of the PPP collected in the reservoir container 90 in the double needle system 30 is returned to the donor with the RBC during the return cycle. This portion of PPP is conveyed from the reservoir container 90 through tubing branch 88 via the cassette 22B to tubing branch 66, which leads to tubing branch 32 and the second needle 48 via cassette 22A.

As in the single needle system 28, another portion of the PPP collected in the reservoir container 90 is used in the double needle system 30 to resuspend PC in the second stage compartment 36 after separation ends, in the same manner already described. As already described, tubing branch 94 conveys resuspended PC from the cassette 22C to collection containers 96.

As in the single needle system 28, the PPP in the reservoir container 90 can serve as an anticoagulated "keep open" fluid or as a "final flush" fluid. The PPP remaining in the reservoir container 90 after processing can be stored for therapeutic purposes.

As in the single needle system 28, container 50 holds a saline priming solution, which is used to purge air from the system 28 before processing. In the two needle system 30, tubing branch 53 leads from the container 50 through drip chambers 54 and 57 into cassette 22A, and from there into the first stage compartment 34 for distribution throughout the rest of the system 30.

The system 30 includes a waste bag 106 connected to cassette 22A via tubing branch 104 to collect air during priming. The waste bag 106 is also used to purge air from the system 30 during use. In the single needle system 28, containers 58 and 70 serve to collect air during priming and processing.

The bag 106 (in system 30) and bags 58/70 (in system 28) also serve as buffers to collect excess fluid pressure from the processing chamber 16.

II. THE CENTRIFUGE ASSEMBLY

The centrifuge assembly 12 (see FIGS. 1 and 21) carries the operating elements essential for a diverse number of blood processing procedures under the direction of an onboard controller.

As FIGS. 1 and 21 show, the centrifuge assembly 12 is housed with a wheeled cabinet 228, which the user can easily move from place to place. It should be appreciated that, due to its compact form, the centrifuge assembly 12 also could be made and operated as a tabletop unit.

The centrifuge assembly 12 includes a centrifuge 230 (see FIGS. 21 and 22) mounted for rotation inside a compartment 232 of the cabinet 228. The compartment 232 has a fold-open door 234. The user folds the door 234 open (see FIG. 22) to gain access to the centrifuge 230 to load and unload the processing chamber 16 of the fluid circuit 18. As FIG. 21 shows, the user folds the door 234 close to enclose the centrifuge 230 inside the compartment 232 for use (as FIG. 1 also shows).

Figure 23:
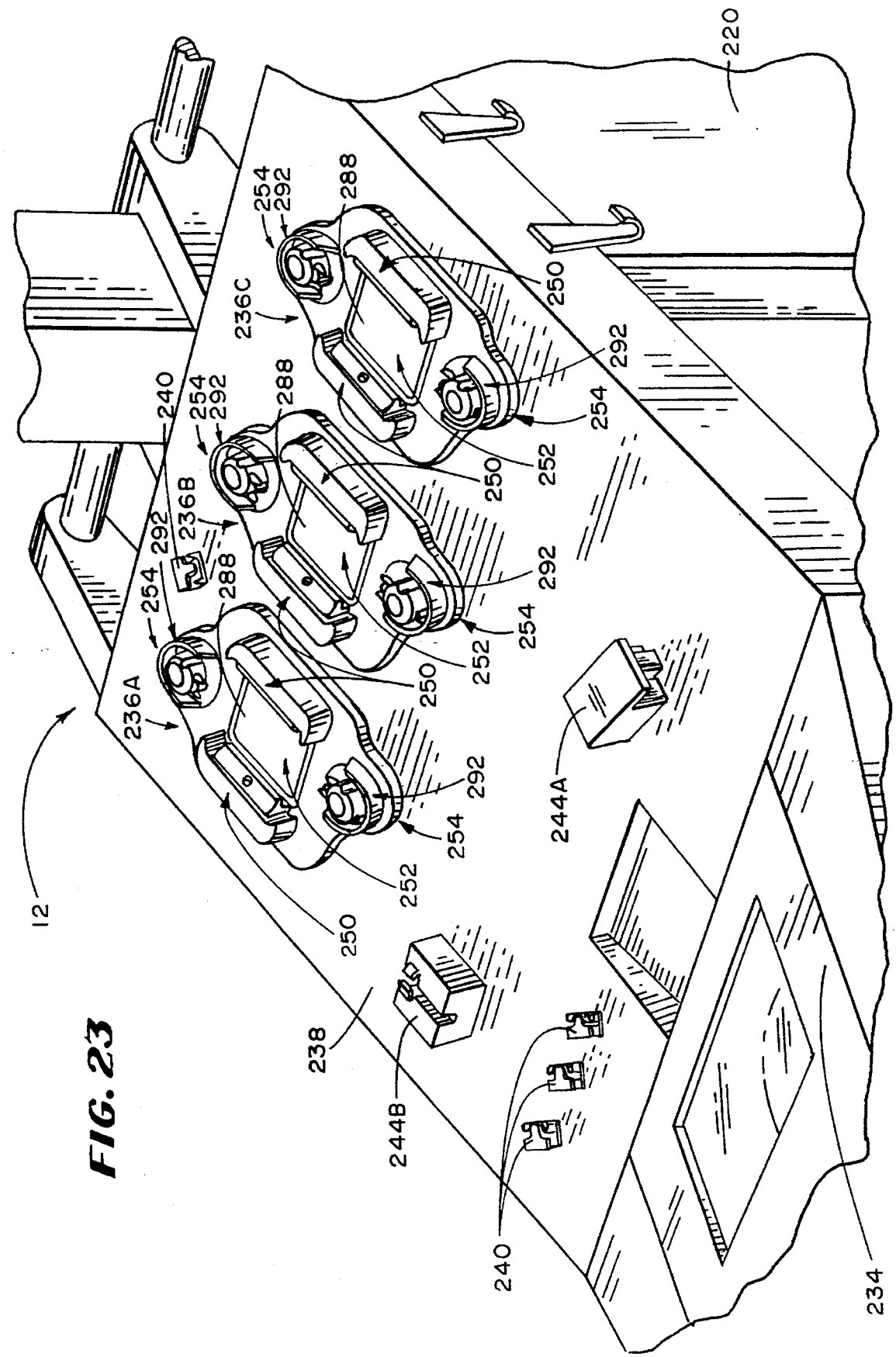
FIG. 23 is a perspective view of the cassette holding stations located on the sloped front panel of the centrifuge assembly, just above the associated centrifuge shown in FIGS. 21 and 22.

The centrifuge assembly 12 also includes three cassette control stations 236 A/B/C (see FIG. 23), one for each cassette 22 A/B/C. The cassette control stations 236 A/B/C are located side by side on a sloped outside panel 238 of the cabinet 228. The outside panel 238 also carries the shut-off clamps 240, hemolysis sensor 244A, and air detector 244B associated with the centrifuge assembly 12 (see FIG. 23).

The centrifuge assembly 12 includes a processing controller 246. The controller 246 governs the operation of the centrifuge assembly 12. The processing controller 246 preferably includes an integrated input/output terminal 248 (also seen on FIG. 1), which receives and display information relating to the processing procedure.

The following description provides further details of these and other components of the centrifuge assembly 12.

(i) The Cassette Control Stations

Figure 25:
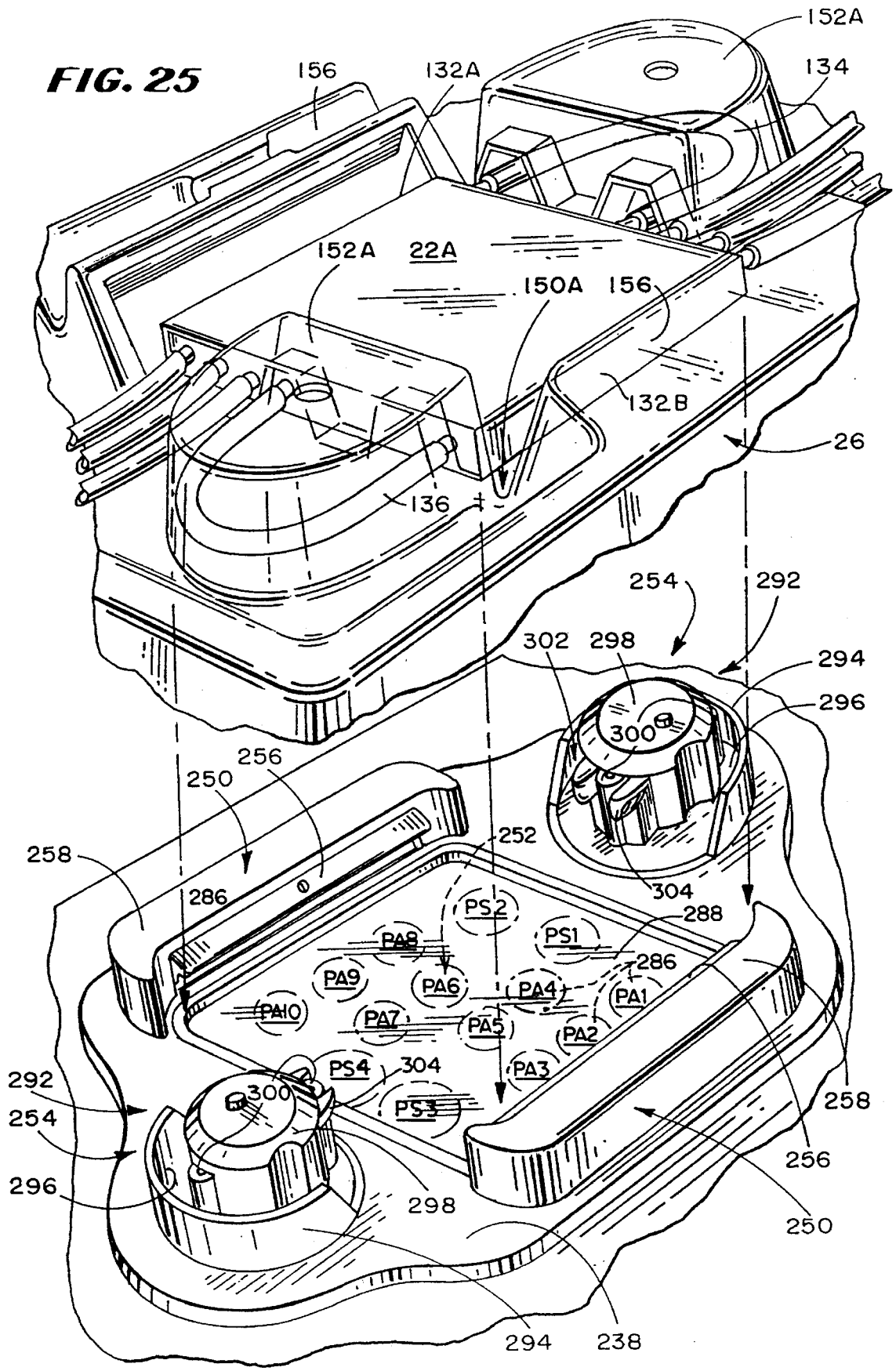
FIG. 25 is a perspective view of a cassette, carried within the tray, positioned for placement on the cassette holding station shown in FIG. 24.

In use, each control station 236A/B/C holds one cassettes 22A/B/C (see FIG. 25). The control station are all constructed alike, so the details of only one station 236A will be provided. In use, the station holds the cassette 22A.

The control station 236A (see FIGS. 24 and 25) includes a cassette holder 250. The holder 250 receives and grips the cassette 22A along two opposed sides 132A and B in the desired operating position on the control station 236A.

The holder 250 urges the diaphragm 116 on the front cassette side 112 into intimate contact with a valve module 252 on the control station 236 A. The valve module 252 acts in concert with the valve stations V1/V10 and sensing stations S1/S2/S3/S4 in the cassette 22A.

The control station also includes a peristaltic pump module 254. When the cassette 22A is gripped by the holder 250, the tubing loops 134 and 136 make operative engagement with the pump module 254.

The controller 246 governs the operation of holder 250 on each control station 236A/B/C to grip the cassettes 22A/B/C upon receipt of a preselected command signal. The controller 246 then proceeds to govern the operation of the valve module 252 and pump module 254 on each control station 236A/B/C to convey liquids through the cassettes 22A/B/C to achieve the processing objectives of the system 10.

(A) The Cassette Holders

Figure 26:
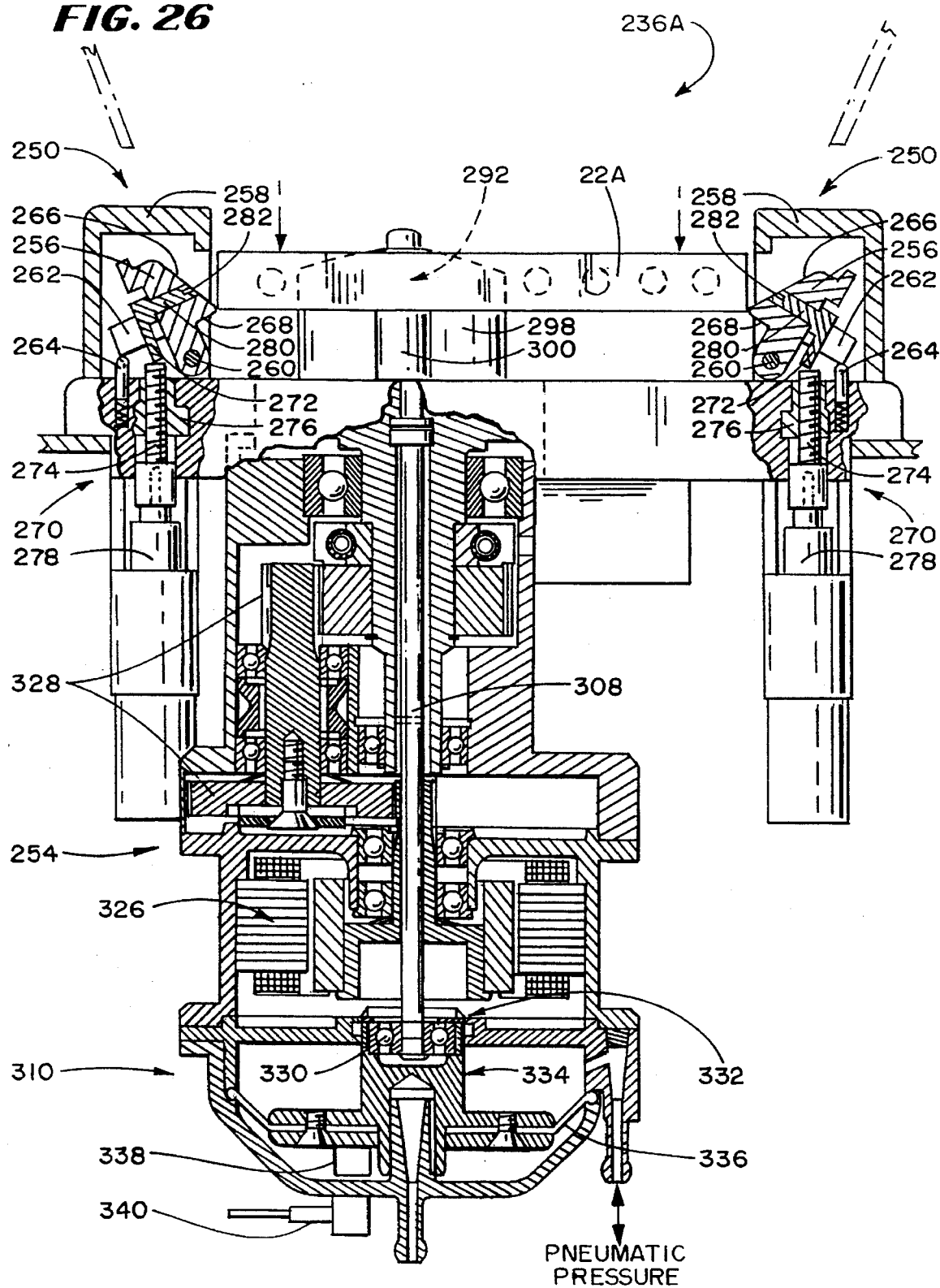
FIG. 26 is a side section view of the cassette as it is being lowered upon the cassette holding station shown in FIG. 25, and also showing in an elevated side section view the interior of an associated pump module.
Figure 27:
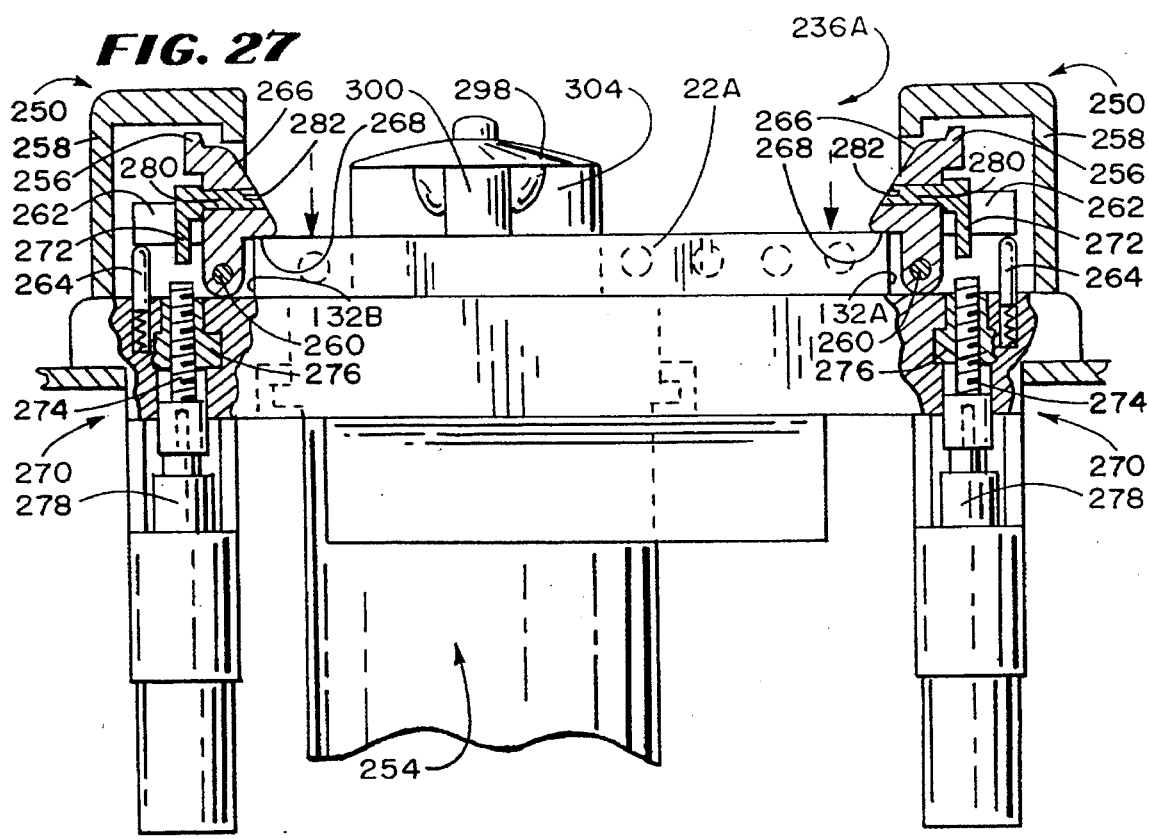
FIG. 27 is a side section view of the cassette lowered upon the cassette holding station shown in FIG. 25, with the associated gripping elements shown in an unlocked position.

FIGS. 26 and 27 show the details of construction of the cassette holder 250.

Figure 24:
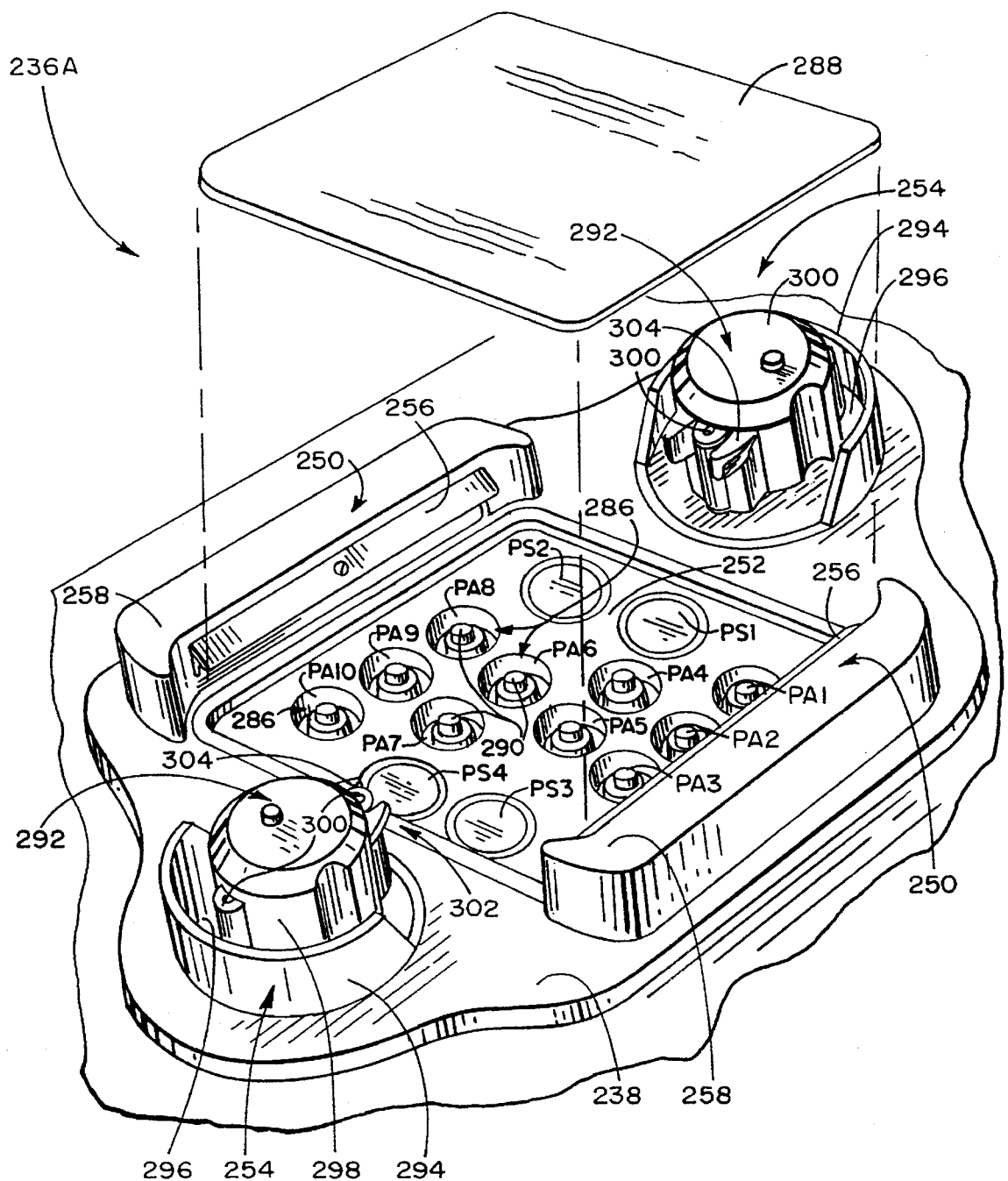
FIG. 24 is a perspective view of the pump and valve modules on one cassette holding station, with the splash guard lifted to show the associated valve assemblies and pressure sensors.

Each holder 250 includes a pair of diametrically spaced gripping elements 256 (which FIGS. 24 and 25 also show). The elements 256 are housed within covers 258 on the sloped front panel 238 of the cabinet 228.

Each gripping element 256 is carried on a shaft 260 for rocking movement. The element 256 rocks between a forward position, gripping the associated cassette 22A (see FIG. 27), and a rearward position, releasing the associated cassette 22A (see FIG. 26).

A biasing tab 262 projects from the rear of each gripping element 256. A spring loaded pin 264 pushes against the tab 262, urging the element 256 forward into its gripping position.

The front of each gripping element 256 projects beyond the cover 258. The front includes a sloped cam face 266 that leads to a recessed detente 268. When the cassette 22A is lowered upon the station 236 A (see FIG. 26), the side edges 132A/B of the cassette 22A contact the sloped cam face 266. Pressing against the back panel 118 of the cassette 22A slides the side edges 132A/B down the cam face 266. The sliding contact rocks the gripping elements 256 rearward against the biasing force of the spring loaded pin 264.

The gripping elements 256 open to receive the descending cassette 22A, until the cassette side edges 132A/B reach the recessed detente 268 (see FIG. 27). This relieves the rearward rocking force against the cam surface 266. The biasing force of the spring loaded pins 264 rock the gripping elements 256 forward, capturing the cassette side edges 132A/B within the recessed detentes 268. The biasing force of the spring loaded pins 264 releasably clamp the gripping elements 256 against the cassette side edges 132A/B.

The biasing force of the spring loaded pins 264 can be overcome by lifting upward upon the cassette 22A. The upward lifting moves the cassette side edges 132A/B against the detentes 268, rocking the gripping elements 256 rearward to open and release the cassette 22A (as FIG. 26 shows).

In the illustrated and preferred embodiment, each holder 250 includes a mechanism 270 (see FIGS. 28 to 30) that selectively prevents the removal of the cassette 22A. The mechanism 270 locks the gripping elements 256 into their forward clamp position.

Figure 28:
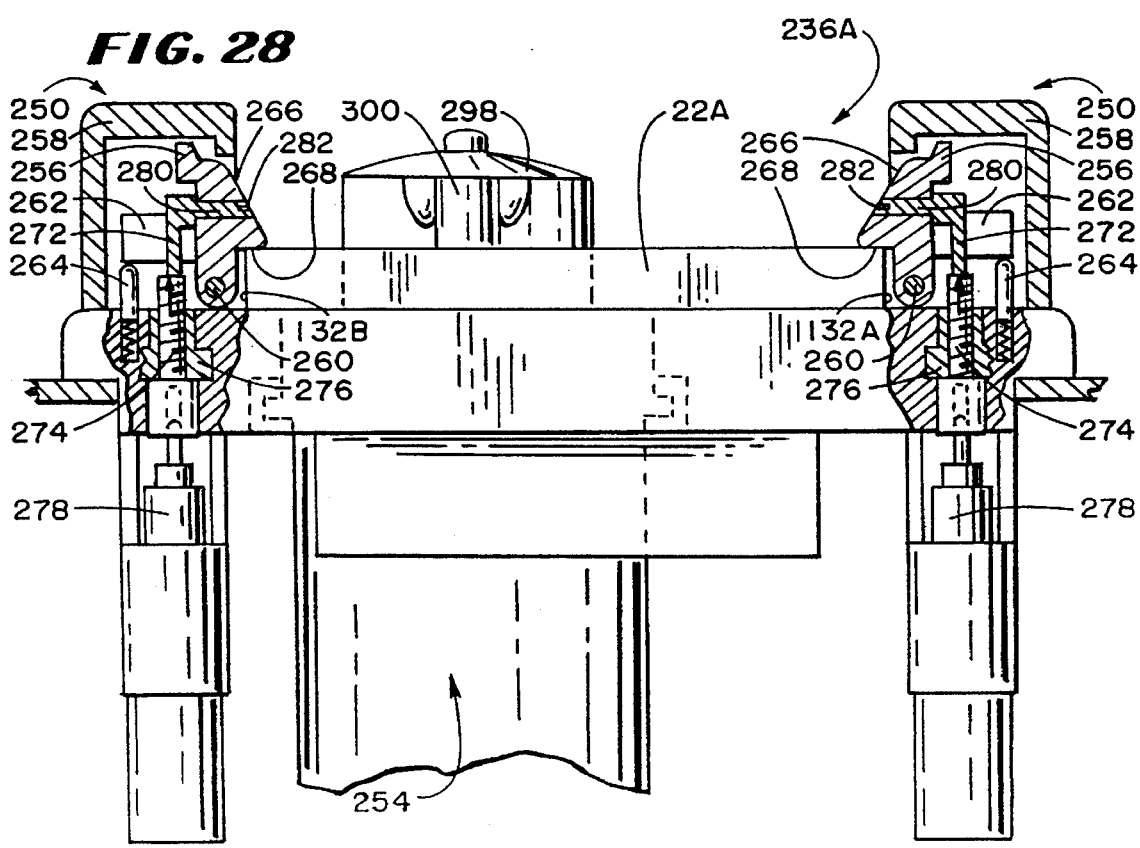
FIG. 28 is a side section view of the cassette lowered upon the cassette holding station shown in FIG. 25, with the associated gripping elements shown in a locked position.
Figure 37:
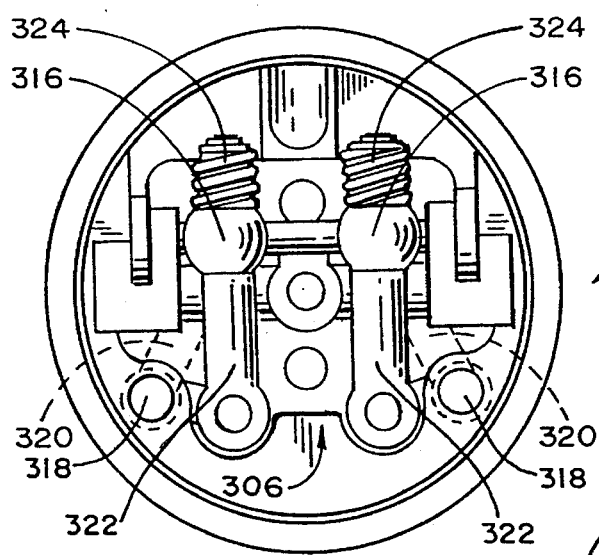
FIGS. 37 and 38 are top views of parts of the roller locating mechanism shown in FIGS. 35 and 36, with the rollers shown in their retracted positions.
Figure 38:
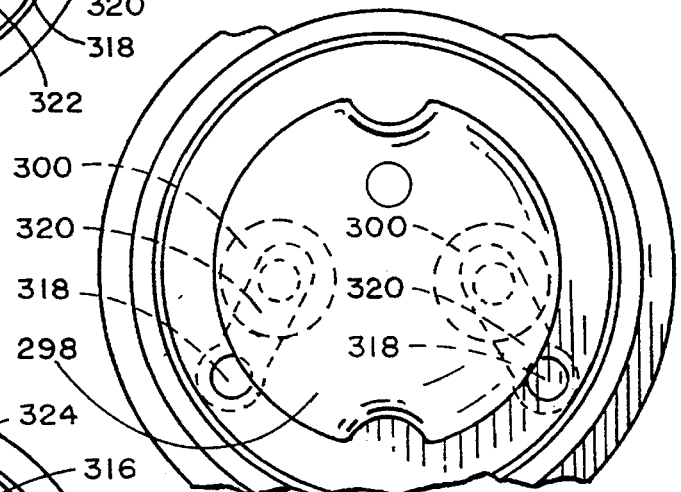
Figure 39:
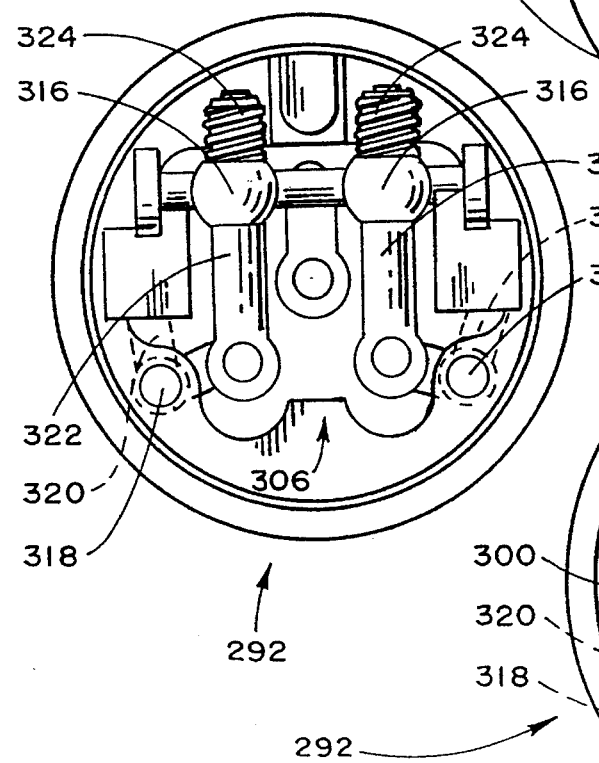
FIGS. 39 and 40 are top views of parts of the roller locating mechanism shown in FIGS. 35 and 36, with the rollers shown in their extended positions.
Figure 40:
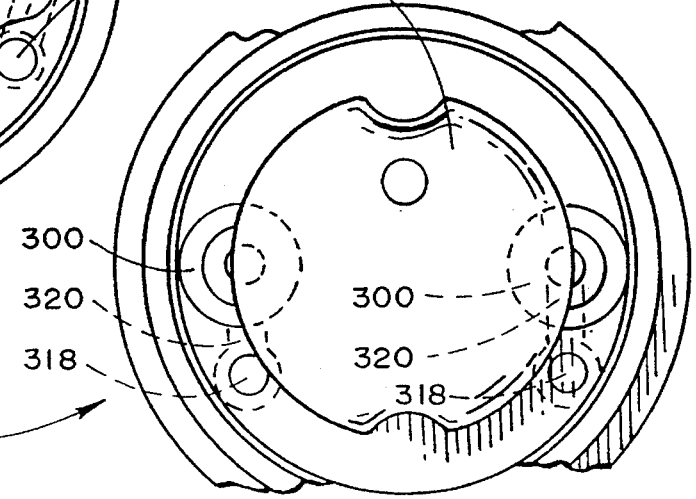

The locking mechanism 270 can vary in construction. In the illustrated embodiment (as FIGS. 28 to 30 show), the mechanism 270 includes a locking tab 272 that projects from the rear of each gripping element 256. The mechanism 270 further includes a locking screw 274 associated with each locking tab 272. An electric motor 278 rotates the screw 274 within a stationary ferrule 276, causing the screw 274 to move upward and downward.

Upward movement brings the screw 274 into contact against the locking tab 272 (See FIGS. 28 to 30). This contact prevents rearward movement of the gripping element 256, locking the element 256 in its forward, gripping position.

In this position, the screw 274 prevents removal of the cassette 22A from the grip of the element 256, providing the positive force F1 (see FIG. 8) that seats the cassette diaphragm 116 against the upstanding edges 120.

Operation of the motor 278 to move the screw 274 downward frees contact with the locking tab 272 (see FIG. 27). The gripping element 256 is now free to rock forward and rearward in response to cassette movement, in the manner already described.

In the illustrated and preferred embodiment (see FIGS. 31 to 34), the locking mechanism 270 can be manually disabled. The locking tab 272 is carried on a shaft 280 that terminates in a turn key 282 accessible on front cam surface 266 (best seen in FIG. 30). A conventional screw driver blade 284 mates with the turn key 282.

Rotation of the turn key 282 by the blade 284 rotates the locking tab 272 out of the uppermost reach of the locking screw 274 (see FIGS. 32 and 33). When the locking screw 274 is in its uppermost position, the rotation breaks contact between the locking tab 272 and screw 274. This frees the gripping element 256 to rock rearward to release the cassette 22A (see FIG. 34).

Therefore, should a power or mechanical failure prevent actuation of the motor 278, the cassette 22A can be manually released from the elements 256 without lowering the locking screw 274.

(B) The Cassette Valve Module

Referring back to FIG. 24, the valve module 252 on each control station 236A/B/C contains an array of valve assemblies 286 located between the gripping elements 256. The force F1 that the gripping elements 256 exert (see FIG. 8), hold the diaphragm 116 of the cassette 22A in intimate contact against the valve assemblies 286.

In the illustrated and preferred embodiment (as FIG. 24 shows), a thin elastomeric membrane 288 is stretched across the valve assembly 286, serving as a splash guard. The splash guard membrane 288 keeps liquids and dust out of the valve assembly 286. The splash guard membrane 288 can be periodically wiped clean when cassettes are exchanged.

The valve assembly 286 includes ten valve actuating pistons PA1 to PA10 and four pressure sensing transducers PS1 to PS4. The valve actuators PA1 to PA10 and the pressure sensing transducers PS1 to PS4 are mutually arranged to form a mirror image of the valve stations V1 to V10 and sensing stations S1 to S4 on the front side 112 of the cassette 22A.

When the cassette 22A is gripped by the elements 256, the valve actuators PA1 to PA10 align with the cassette valve stations V1 to V10. At the same time, the pressure sensing transducers PS1 to PS4 mutually align with the cassette sensing stations S1 to S4.

Each valve actuator PA1 to PA10 comprises an electrically actuated solenoid piston 290. Each piston 290 is independently movable between an extended position and a retracted position.

When in its extended position, the piston 290 presses against the region of the diaphragm 116 that overlies the associated valve station V1/V10 (exerting the force F2 shown in FIG. 8). In this position, the piston 290 flexes the diaphragm 116 into the associated valve station to seat the diaphragm 116 against the ring 124, and thereby seal the associated valve port 122A. This closes the valve station to liquid flow.

When in its retracted position, the piston 290 does not apply force against the diaphragm 116. As before described, the plastic memory of the diaphragm 116 unseats it from the valve ring 124 (as FIG. 8 shows), and thereby opens the valve station to liquid flow.

The pressure sensing transducers PS1 to PS4 sense liquid pressures in the sensing stations S1 to S4. The sensed pressures are transmitted to the controller 246 as part of its overall system monitoring function.

(C) The Cassette Pumping Module

As FIGS. 24 and 25 show, in the illustrated and preferred embodiment, each cassette pumping module 254 includes a pair of peristaltic rotor assemblies 292. The rotor assemblies 292 face each other at opposite ends of the valve assembly 286.

A rear wall 294 extends about half way around the back side of each rotor assembly 292 (see FIGS. 24 and 25). The space between the rear wall 294 and the rotor assembly 292 forms a pump race 296. When the cassette 22A is gripped by the elements 256, the tubing loops 134 and 136 extend into the pump race 296 (see FIG. 41).

Figure 44A:
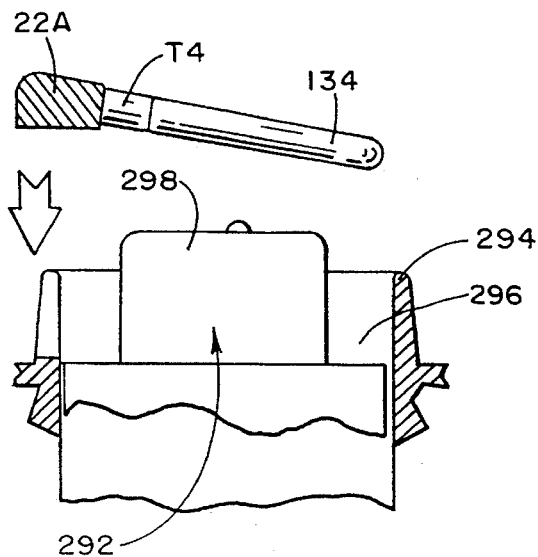
FIGS. 44A and 44B are diagrammatic side views of aspects of the self-loading feature that the pump module incorporates.

As before described, the tube connectors T4/T5 and T6/T7 from which the loops 134 and 136 extend slope in the direction the pump rotor assemblies 292 (see FIG. 44A). The angled connectors T1/T2 and T9/T10 orient the loops 134 and 136 relative to the race 296 while loading the cassette 22A onto the station 236A (see FIGS. 44A and 44B). This aspect will be described in greater detail later.

Referring back to FIGS. 24 and 25, each rotor assembly 292 includes a rotor 298 that carries a pair of diametrically spaced rollers 300. In use, as the pump rotor 298 rotates, the rollers 300 in succession compress the associated tubing loop 134/136 against the rear wall 294 of the pump race 296. This well known peristaltic pumping action urges fluid through the associated loop 134/136.

In the illustrated and preferred embodiment, each rotor assembly 292 includes a self-loading mechanism 302. The self-loading mechanism 302 assures that the tubing loops 134/136 are properly oriented and aligned within their respective pump races 296 so that the desired peristaltic pumping action occurs.

While the specific structure of the self-loading mechanism 302 can vary, in the illustrated embodiment, it includes a pair of guide prongs 304 (see FIGS. 24 and 25). The guide prongs 304 extend from the top of each rotor 298 along opposite sides of one of the pump rollers 300.

In this arrangement, the loading mechanism 302 also includes a roller locating assembly 306 (see FIGS. 35 to 40). The locating assembly 306 moves the pump rollers 300 radially of the axis of rotation. The rollers 300 move between a retracted position within the associated pump rotor 298 (see FIGS. 37 and 38) and an extended position outside the associated pump rotor 298 (see FIGS. 39 and 40).

When retracted (see FIGS. 37 and 38), the rollers 300 make no contact with the loops 134/136 within the races 296 as the rotors 298 rotate. When extended (see FIGS. 39 and 49), the rollers 300 contact the loops 134/136 within the races 296 to pump fluid in the manner just described.

The roller locating assembly 306 also may be variously constructed. In the illustrated and preferred embodiment (see FIGS. 35 and 36), the assembly 306 includes an actuating rod 308 that extends along the axis of rotation of the associated roller 298. One end of the actuating rod 308 is coupled to a linear actuator 310 (see FIG. 26). The actuator 310 advances the rod 308 toward the pump rotor 298 and away from the pump rotor 298 in response to controller commands (as the arrows A in FIG. 36 show).

The other end of the rod 308 is attached to a first trunnion 312 within the rotor 298 (see FIGS. 35 and 36). Movement of the rod 308 toward and away from the rotor 298 slides the first trunnion 312 generally along axis about which the rotor 298 rotates (i.e., along arrows A in FIG. 36).

A first link 314 couples the first trunnion 312 to a pair of second trunnions 316, one associated with each roller 300. In FIG. 36, only one of the second trunnions 316 is shown for the sake of illustration. The first link 314 displaces the second trunnions 316 in tandem in a direction generally transverse the path along which the first trunnion 312 moves (as shown by arrows B in FIG. 36). The second trunnions 316 thereby move in a path that is perpendicular to the axis of rotor rotation (that is, arrows B are generally orthogonal to arrows A in FIG. 36).

Each pump roller 300 is carried by an axle 318 on a rocker arm 320. The rocker arms 320 are each, in turn, coupled by a second link 322 to the associated second trunnion 316.

Displacement of the second trunnions 316 toward the rocker arms 320 pivots the rocker arms 320 to move the rollers 300 in tandem toward their retracted positions (as shown by arrows C in FIG. 36).

Displacement of the second trunnions 316 away from the rocker arms 320 pivots the rocker arms 320 to move the rollers 300 in tandem toward their extended positions.

Springs 324 normally urge the second trunnions 316 toward the rocker arms 320. The springs 324 normally bias the rollers 300 toward their retracted positions.

In this arrangement, movement of the actuator rod 308 away from the rotor 298 displaces the second trunnions 316 against the action of the springs 324, pivoting the rocker arms 320 to move the rollers 300 into their extended positions. Movement of the actuator rod 308 toward the rotor 298 augments the spring-assisted return of the rollers 300 to their retracted positions.

The independent action of each spring 324 against its associated second trunnions 316 and links 314 places tension upon each individual pump roller 300 when in its extended position. Each roller 300 thereby independently accommodates, within the compression limits of its associated spring 324, for variations in the geometry and dimensions of the particular tubing loop 134/136 it engages. The independent tensioning of each roller 300 also accommodates other mechanical variances that may exist within the pump module 254, again within the compression limits of its associated spring 324.

As FIG. 26 shows, a small brushless direct current motor 326 drives each peristaltic pump rotor 298. A gear assembly 328 couples the motor 326 to the associated rotor 298.

In the illustrated and preferred embodiment (see FIG. 26), the actuator rod 308 rotates with its associated rotor 298 within the first trunnion 312. The other end of the rotating actuator rod 308 passes through a thrust bearing 330. The thrust bearing 330 has an outer race 352 attached to a shaft 334 that is an integral part of the linear actuator 310.

In the illustrated embodiment, the linear actuator 310 is pneumatically operated, although the actuator 310 can be actuated in other ways. In this arrangement, the actuator shaft 334 is carried by a diaphragm 336. The shaft 334 moves toward the rotor 298 in response to the application of positive pneumatic pressure by the controller 246, thereby retracting the rollers 300. The shaft 334 moves away from the rotor 298 in response to negative pneumatic pressure by the controller 246, thereby extending the rollers 300.

In the illustrated and preferred embodiment (see FIG. 26), the actuator shaft 334 carries a small magnet 338. The actuator 310 carries a hall effect transducer 340. The transducer 340 senses the proximity of the magnet 338 to determine whether the shaft 334 is positioned to retract or extend the rollers 300. The transducer 340 provides an output to the controller 246 as part of its overall monitoring function.

Figure 41:
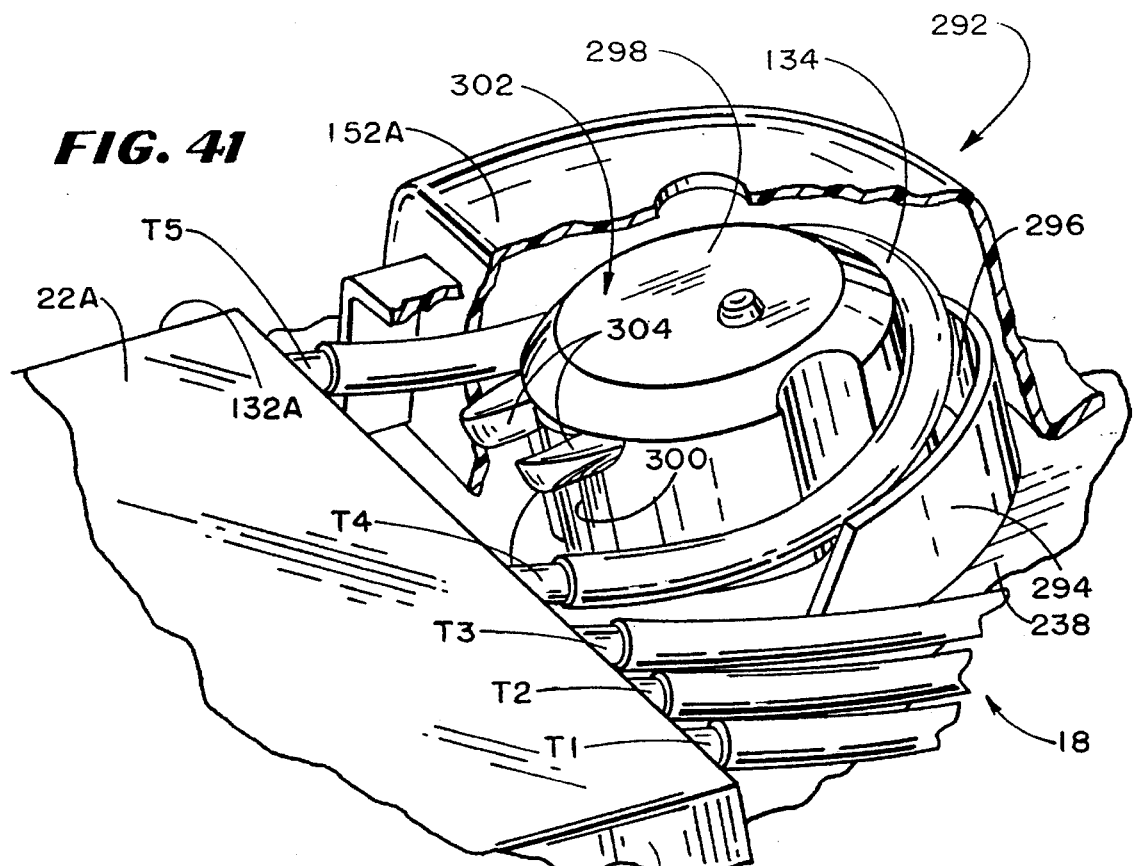
FIGS. 41 to 43 are enlarged perspective views of the self-loading mechanism of the pump module.

Referring now to FIG. 41, in use, the controller 246 actuates the actuator 310 to retract the rollers 300 before the cassette 22A is loaded onto the station 236A. The controller 246 also positions each rotor 298 to orient the guide prongs 304 to face the valve module 252, i.e., to face away from the associated pump race 296.

The cassette 22A is loaded into the gripping elements 256, as already described. The sloped connectors T1/T2 and T9/T10 initially guides the loops 134/136 directly into the pump races 296 (see FIGS. 41 and 44A). The guide prongs 304, being positioned away from the pump race 296, do not obstruct the loading procedure.

Figure 42:
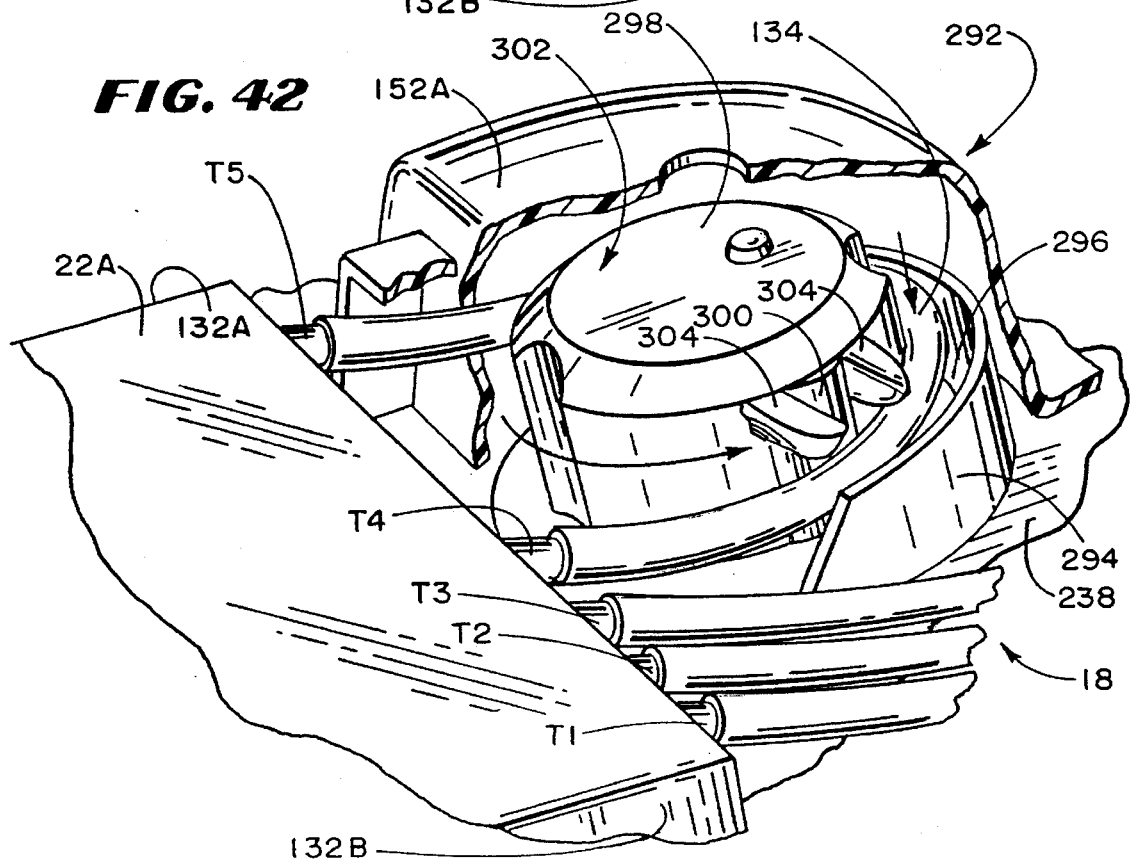
Figure 43:
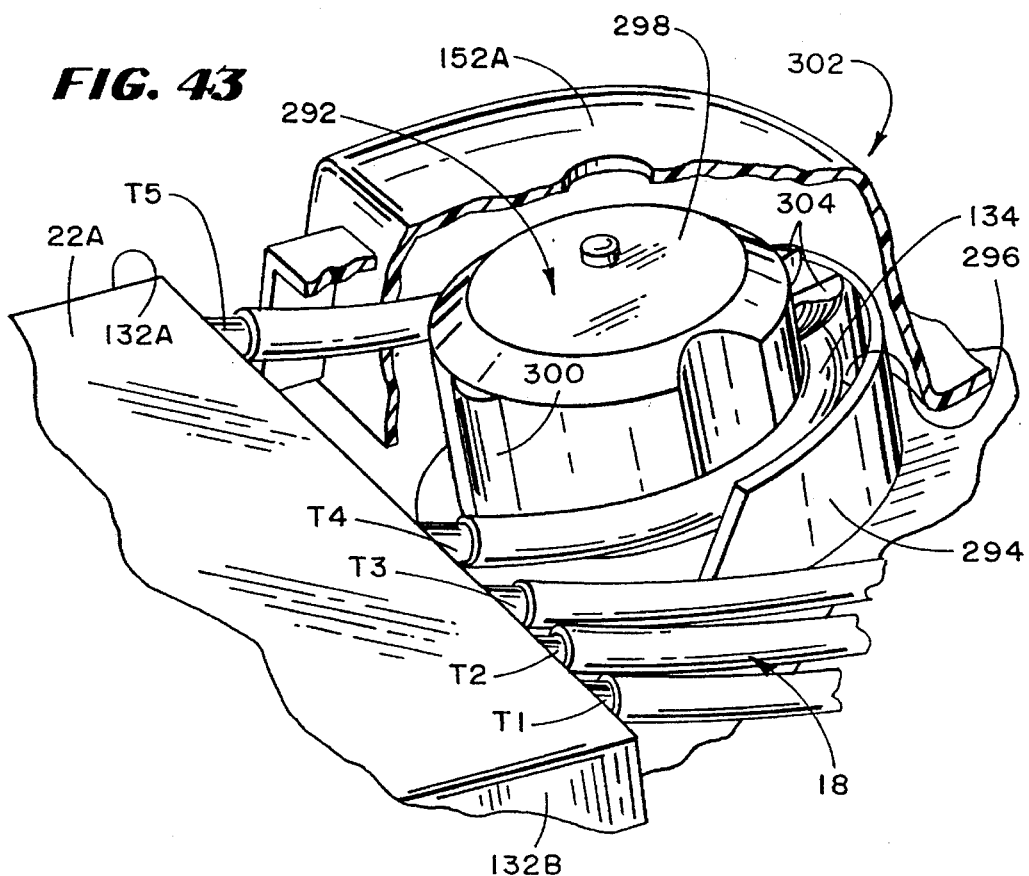
Figure 44B:
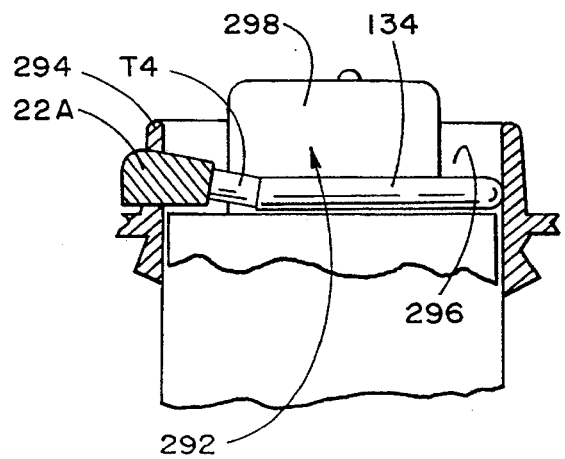

Subsequent rotation of the rotor 298 (see FIGS. 42 and 43) moves the guide prongs 304 into contact with the top surface of the tubing loops 134/136. This contact compresses the tubing loops 134/136 into the pump race 296. This orients the plane of the tubing loops 134/136 perpendicular to the rotational axis of the rotor 298 (as FIG. 44B shows). Several revolutions of the rotor 298 will satisfactorily fit the tuning loop 134/136 into this desired orientation within the race 296. As already pointed out, the retracted rollers 300 serve no pumping function during this portion of the self-loading sequence.

As FIG. 44B shows, the cassette port connectors T4/T5 constrain the spacing between the tubing loops 134/136. The angled orientation of the connectors T4/T5 assure that the tubing loops 134/136 are slightly compressed within the races 296, when oriented perpendicular to the rotors 298 for use.

This arrangement substantially eliminates variances in orientation or alignment of the tubing loops 134/136 within the races 296. The desired uniform linearity between pump rate and pump rotor speed is thus directly related to the mechanics of the pump rotor assembly 292 itself. It is not subject to random variation because of tubing loop misorientation or misalignment within the race 296 during the loading process.

Figure 46:
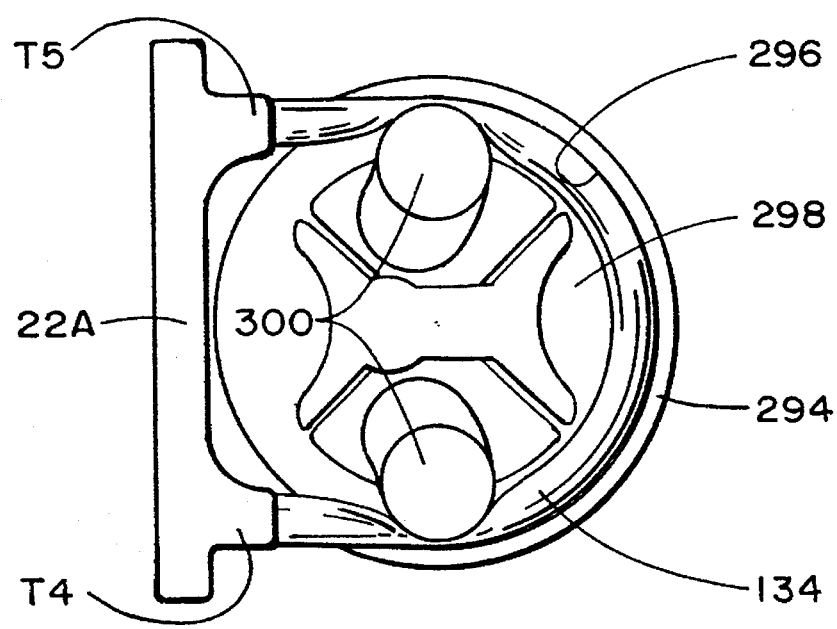

Once the tubing loop 134/136 is fitted within the pump race 296, the controller 246 actuates the roller positioning mechanism 306 to extend the rollers 300 (see FIG. 46). Subsequent rotation of the rotor 298 will squeeze the tubing loop 134/136 within the race 296 to pump liquids in the manner already described.

When it is time to remove the cassette 22A, the controller 246 again retracts the rollers 300 and positions the rotor 298 to orient the guide prongs 304 to face away from the pump race 296. This opens the pump race 296 to easy removal of the tubing loop 134/136.

Figure 45:
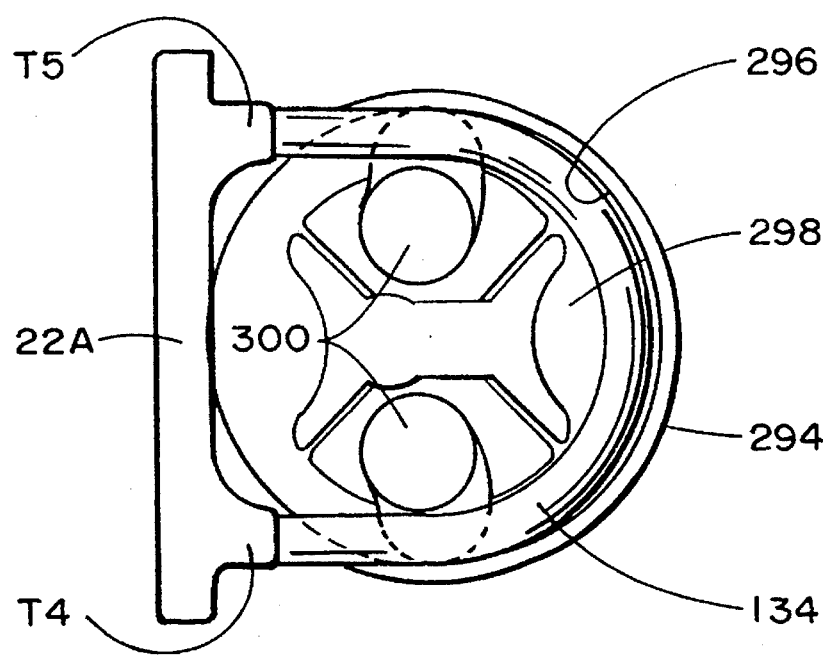
FIGS. 45 and 46 are top view of the pump module showing the retraction and extension of the rollers to perform a valving function.

The roller positioning mechanism 306 can also be actuated by the controller 246 to serve a valving function. The rotor 298 can be stopped with one or more rollers 300 occupying the race 296. The rollers 300, when extended (see FIG. 46) occlude the associated tubing loop 134/136. Retracting the rollers 300 (see FIG. 45) opens the associated tubing loop 134/136.

Selectively retracting and extending the stationary roller 300 serves a valving function to open and close the liquid path through the tubing loop 134/136.

In a preferred embodiment, each pump rotor assembly 292 just described measures about 2.7 inches in diameter and about 6.5 inches in overall length, including the motor 326 and the linear actuator 310. The pump rotor assembly 292 is capable of providing pumping rates in the range between a few milliliters per minute to 250 milliliters per minute.

As shown in FIG. 25, the cassettes 22A/B/C are lowered in tandem with the tray 26 onto the control stations 236A/B/C. The tray chambers 152 A/B/C fit over the pump rotors 298, while the hollow ridges 156 fit over the gripping element covers 258.

These preformed parts of the tray 26 thereby serve as protective covers for operating components of the centrifuge assembly 12, shielding them against ingress of liquids and operator contact during use.

(ii) The Centrifuge

Figure 21A:
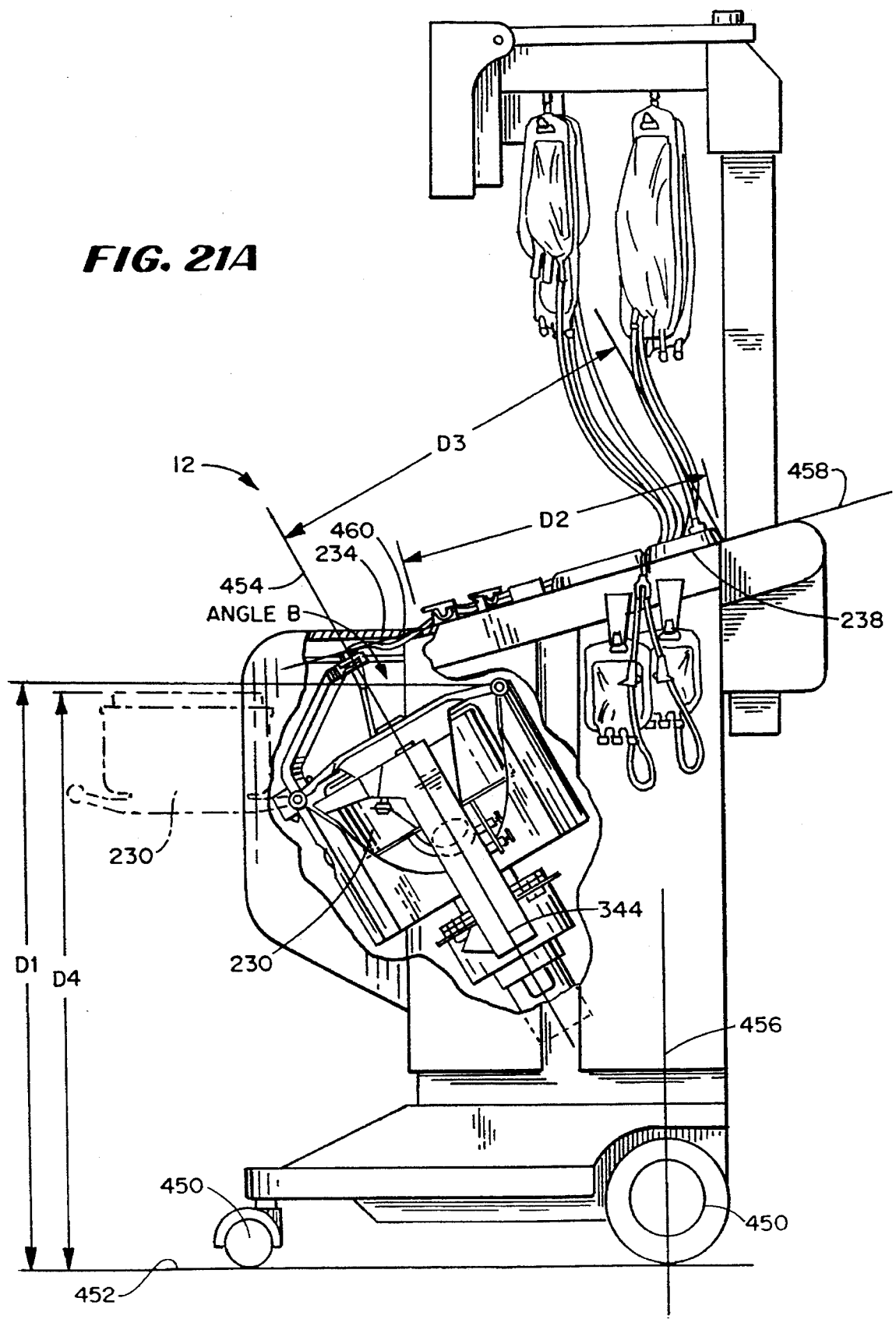
FIG. 21 is a side elevation view of the centrifuge assembly shown in FIG. 1, with the fluid processing assembly mounted for use, and with portions broken away to show the compartment that houses the associated centrifuge.
Figure 22:
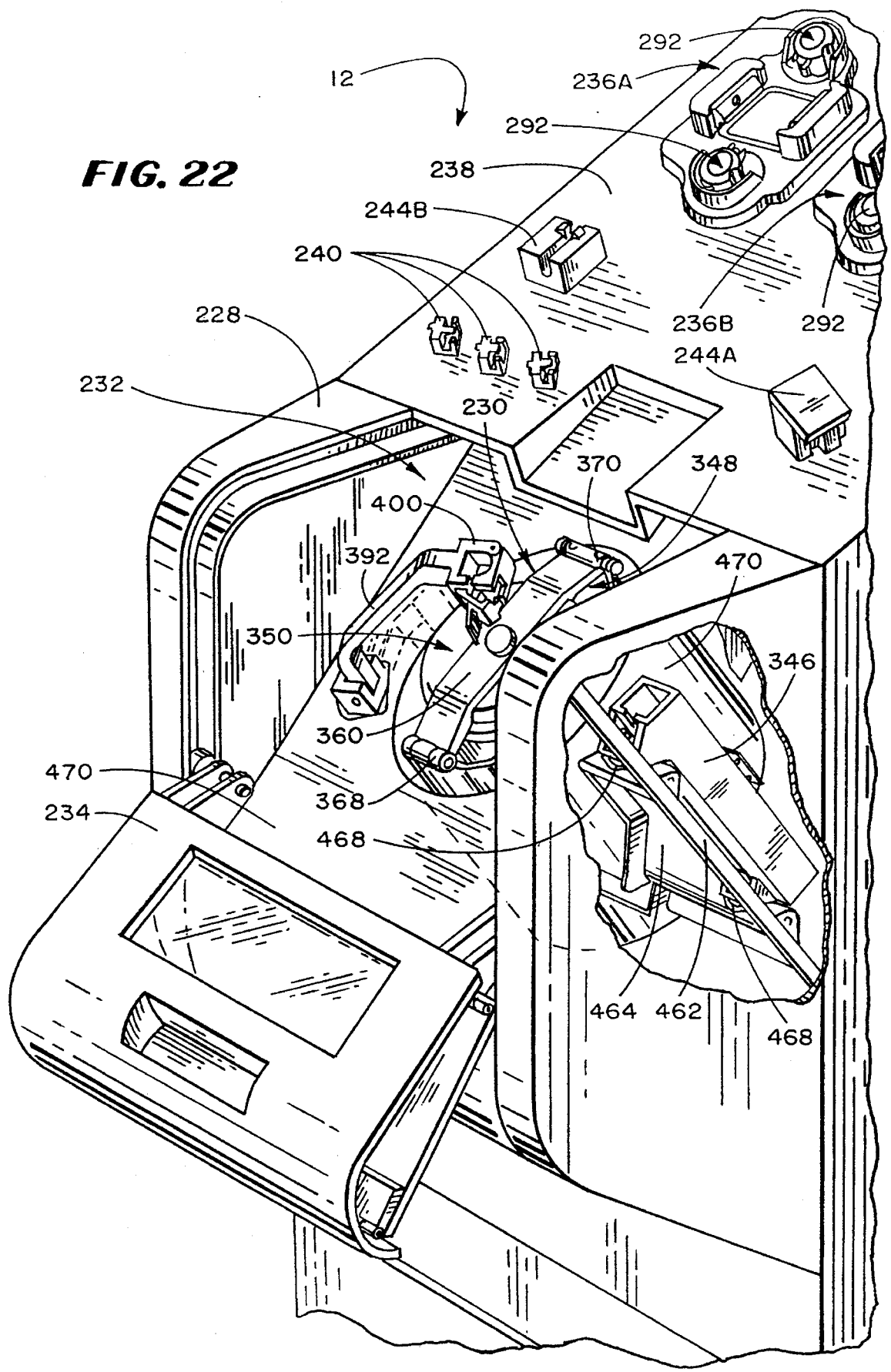
FIG. 22 is a perspective view of the compartment with the door opened to gain access to the centrifuge.

As FIGS. 21 and 21A show, weight bearing wheels 450 support the centrifuge cabinet 228 on the surface 452. The support surface 452 lies generally in the horizontal plane.

The centrifuge 230 rotates about an axis 344 within the compartment 232. As FIG. 21A shows, unlike conventional centrifuges, the rotational axis 344 of the centrifuge 230 is not oriented perpendicular to the horizontal support surface 452. Instead, the rotational axis slopes in a plane 454 outside the vertical plane 456 toward the horizontal support surface 452 (see FIG. 21A).

The centrifuge 230 is supported within the compartment 232 outside the vertical plane 456 such that its rotating components lie near the access door 234 (see FIG. 21). In this way, opening the door 234 provides direct access to the rotating components of the centrifuge 230.

The sloped orientation of rotational axis 344 allows the centrifuge 230 to be mounted in a way that conserves vertical height.

The exterior panel 238, where the principal operating components associated with the centrifuge 230 are supported, lies in a plane 458 (see FIG. 21A) that is not parallel to the horizontal support plane 452. Instead, the panel 238 slopes outside the horizontal plane toward the vertical plane 450. The sloped panel plane 238 intersects the plane 454 in which the rotational axis 344 of the centrifuge 230 lies, forming the intersection angle β (see FIG. 21A).

In this orientation (as FIGS. 21 and 21A show), the bottom edge 460 of the sloped panel 238 lies near the access door 234. In this arrangement, a majority of the centrifuge 230 extends beneath the exterior panel 238.

The sloped orientation of panel 230 conserves horizontal depth.

The angled relationships established between the rotational axis 344 of the centrifuge 230 and the plane 458 of the panel 238 make it possible to place the rotating centrifuge components for access in a zone that lies between the knees and chest of the average person using the machine. These relationships also make it possible to place the stationary functional components like pumps, sensors, detectors, and the like for access on the panel 238 by the user within the same zone. Most preferably, the zone lies around the waist of the average person.

Statistics providing quantitative information about the location of this preferred access zone for a range of people (e.g., Large Man, Average Man/Large Woman, Average Adult, Small Man/Average Woman, etc.) are found in the Humanscale™ Series Manuals (Authors: Niels Diffrient et al., a Project of Henry Dreyfuss Associates), published by the MIT Press, Massachusetts Institute of Technology, Cambridge, Mass.

As will be shown later, these angled relationships established among the rotating and stationary components of the centrifuge assembly 12 provide significant ergonomic benefits that facilitate access to and operation of the assembly 12.

Within these constraints, and depending upon the particular structure of the centrifuge assembly 12, the rotational axis 344 can extend parallel to the horizontal plane 452, or (as FIGS. 21 and 21A show) at an angle somewhere between the horizontal support plane 452 and the vertical plane 456.

Within these constraints, the panel intersection angle β can extend in a range fixed on the lower end by the need to avoid interference between the centrifuge components within the compartment 232 and the pump and sensor components mounted below the panel 238. The range for the angle β is fixed on the upper end by the need to avoid interference with hanging solution containers 20 and other components mounted above the panel.

In the illustrated and preferred embodiment (see FIG. 21A), the plane 454 in which the rotational axis 344 of the centrifuge 230 lies extends at about a 45° angle with respect to the horizontal support plane 452.

In the illustrated and preferred embodiment, the vertical height between the support surface 452 and the top of the centrifuge 230 (identified as D1 in FIG. 21A) is about 30". This places the centrifuge 230 within the desired access zone of a statistically "typical" small woman, when standing, as defined by the above identified Humanscale™ Series Manuals.

In the illustrated and preferred embodiment (see FIG. 21A), the panel 230 has an overall length of about 18 inches (designated D2 in FIG. 21A). The intersection angle β is about 70°. In this orientation, the horizontal depth of the centrifuge assembly 12 (identified by D3 in FIG. 21A), measured between the plane 454 of the rotational axis 344 and the back edge of the panel 230, is about 24 inches.

This places all the components mounted on and above the panel 230 within the comfortable horizontal reach of the statistically "typical" small woman (as defined above), when standing, without need to overreach or over-extend.

These relationships can be structurally achieved in various ways. In the illustrated and preferred embodiment (see FIGS. 47 and 48), the underlying structural support for the cabinet 228 includes angled side braces 462 in the perimeter of the compartment 232. A transverse support bracket 464 is fastened between the side braces 462.

A stationary platform 346 carries the rotating mass of the centrifuge 230. The platform 346, and therefore the entire rotating mass of the centrifuge 230, are mounted on the transverse support bracket 464 by a series of spaced apart flexible mounts 468. The flexible mounts 468 support the rotating mass of the centrifuge 230 at the described inclined, nonperpendicular relationship.

Figure 47:
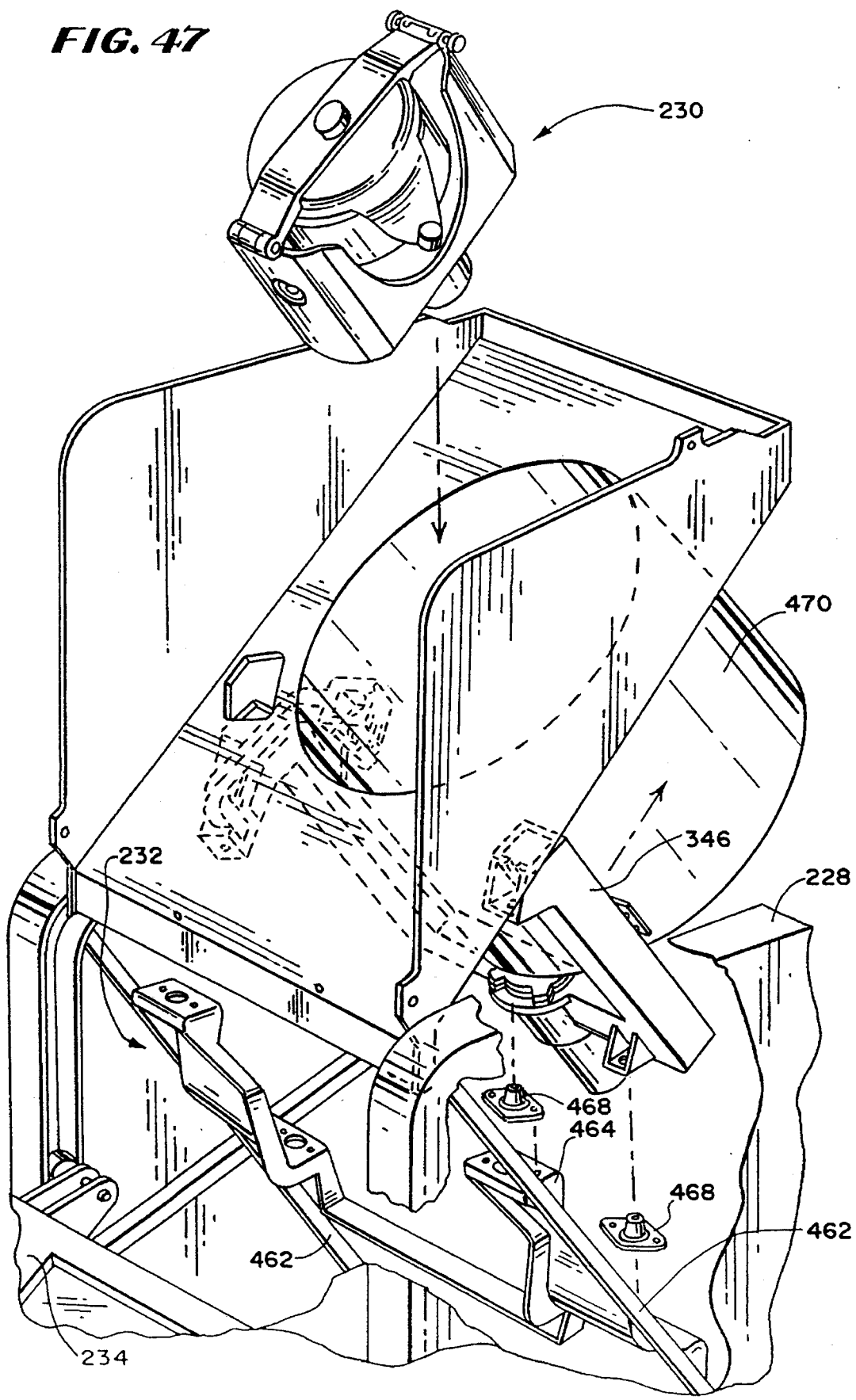
FIG. 47 is an exploded perspective view of the centrifuge shown in FIGS. 21 and 22 showing the structure that supports the rotating mass of the centrifuge.
Figure 48:
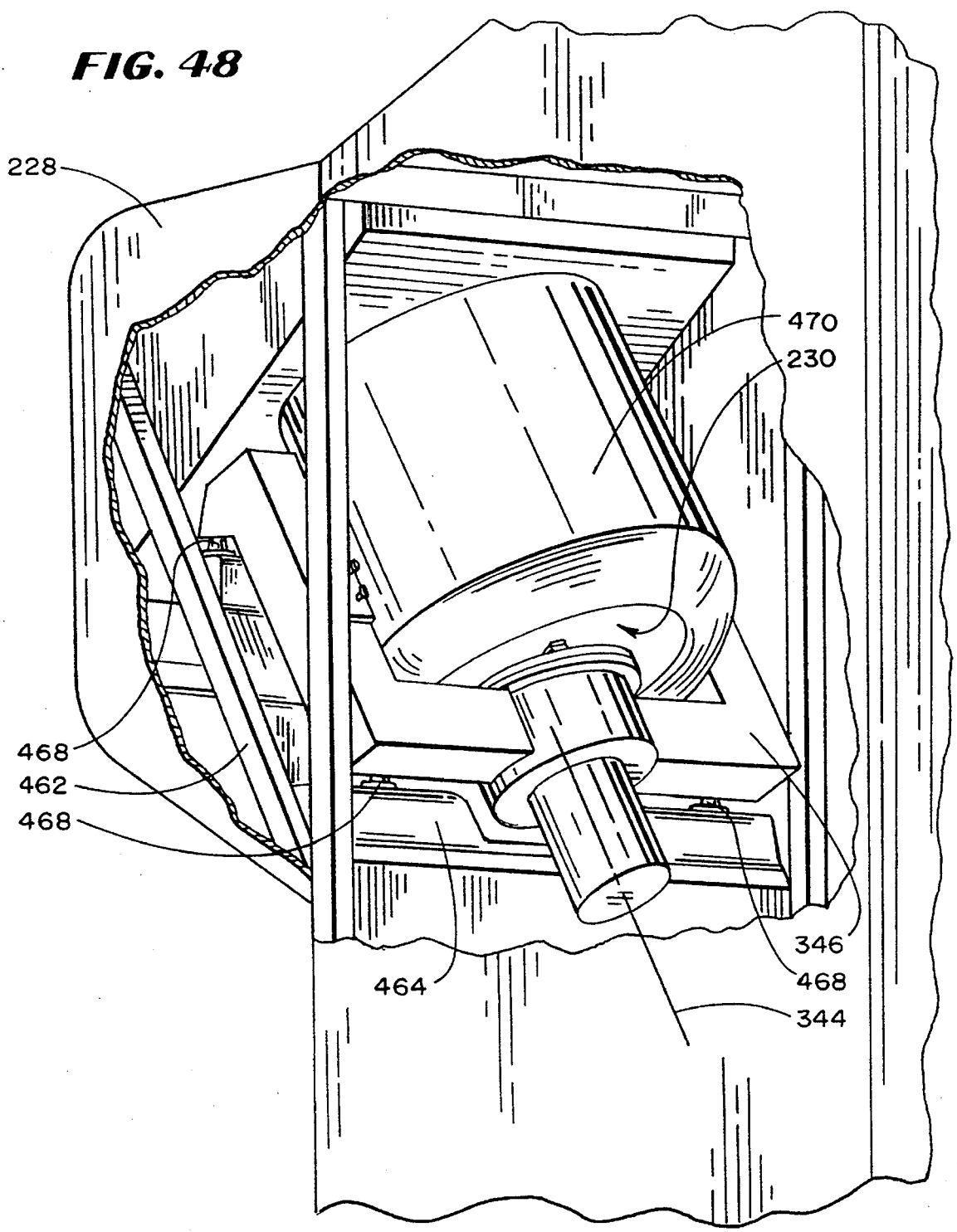
FIG. 48 is an assembled perspective view of the centrifuge shown in FIG. 47 from within the centrifuge.

Preferably (as FIGS. 47 and 48 show), a spill shield 470 is attached to the stationary platform 346. The shield 470 enclose all but the top portion of the rotating components of the centrifuge 230 (as FIG. 22 also shows).

Figure 49:
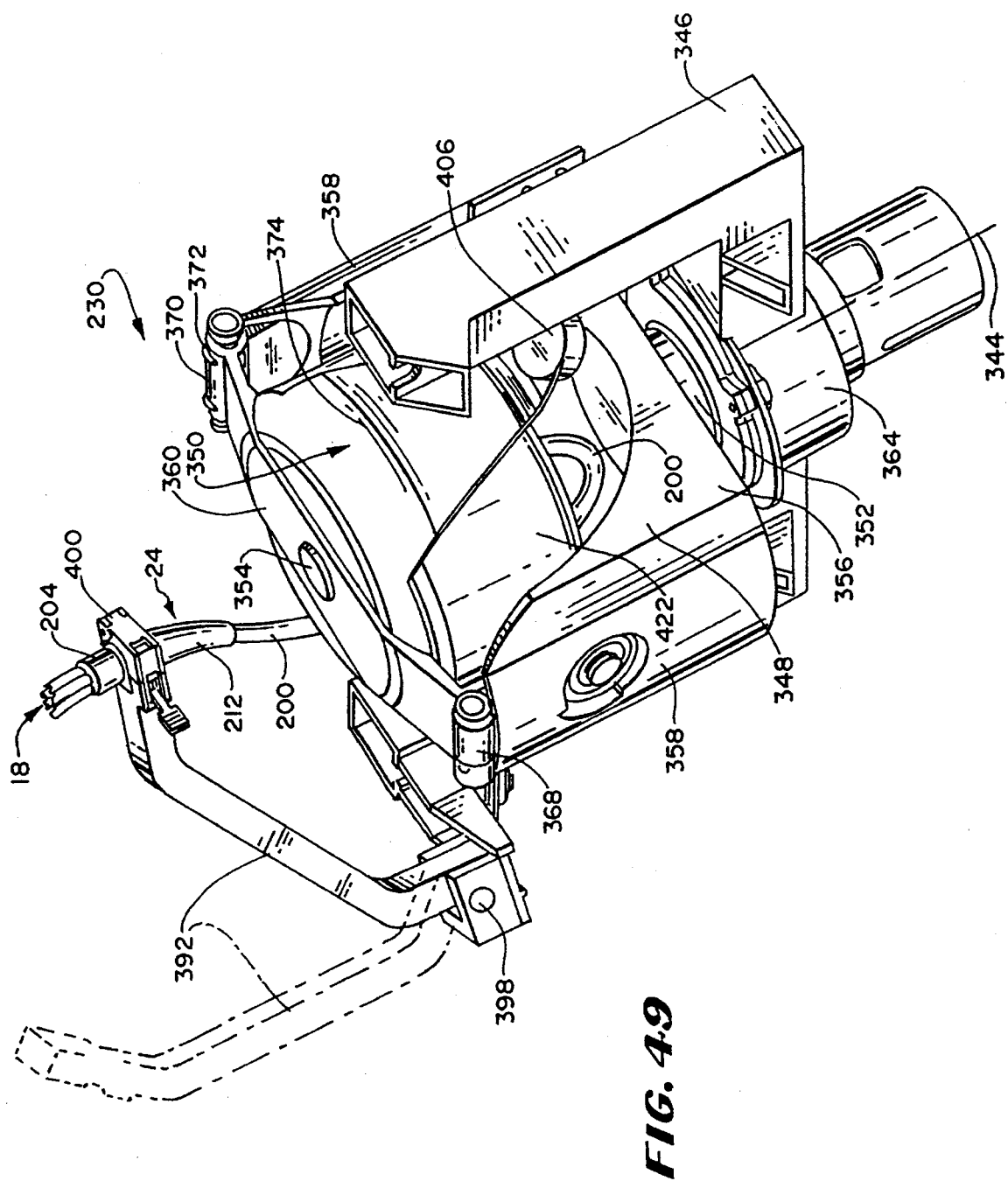
FIG. 49 is an enlarged perspective view of the centrifuge shown in FIGS. 21 and 22, with the associated chamber assembly being shown in its operating position.

As shown in FIG. 49, the rotating components of the centrifuge 230 include a centrifuge yoke assembly 348 and a centrifuge chamber assembly 350. The yoke assembly 348 rotates on a first axle 352. The chamber assembly 350 rotates on the yoke assembly 348 on a second axle 354. The first and second axles 352 and 354 are commonly aligned along the rotational axis 344.

The yoke assembly 348 includes a yoke base 356, a pair of upstanding yoke arms 358, and a yoke cross member 360 mounted between the arms 358. The base 356 is attached to the first axle 352, which spins on a bearing element 362 about the stationary platform 346 (see FIG. 58, also).

An electric drive 364 rotates the yoke assembly 348 on the first axle 352. In the illustrated and preferred embodiment, the electric drive 364 comprises a permanent magnet, brushless DC motor.

Figure 58:
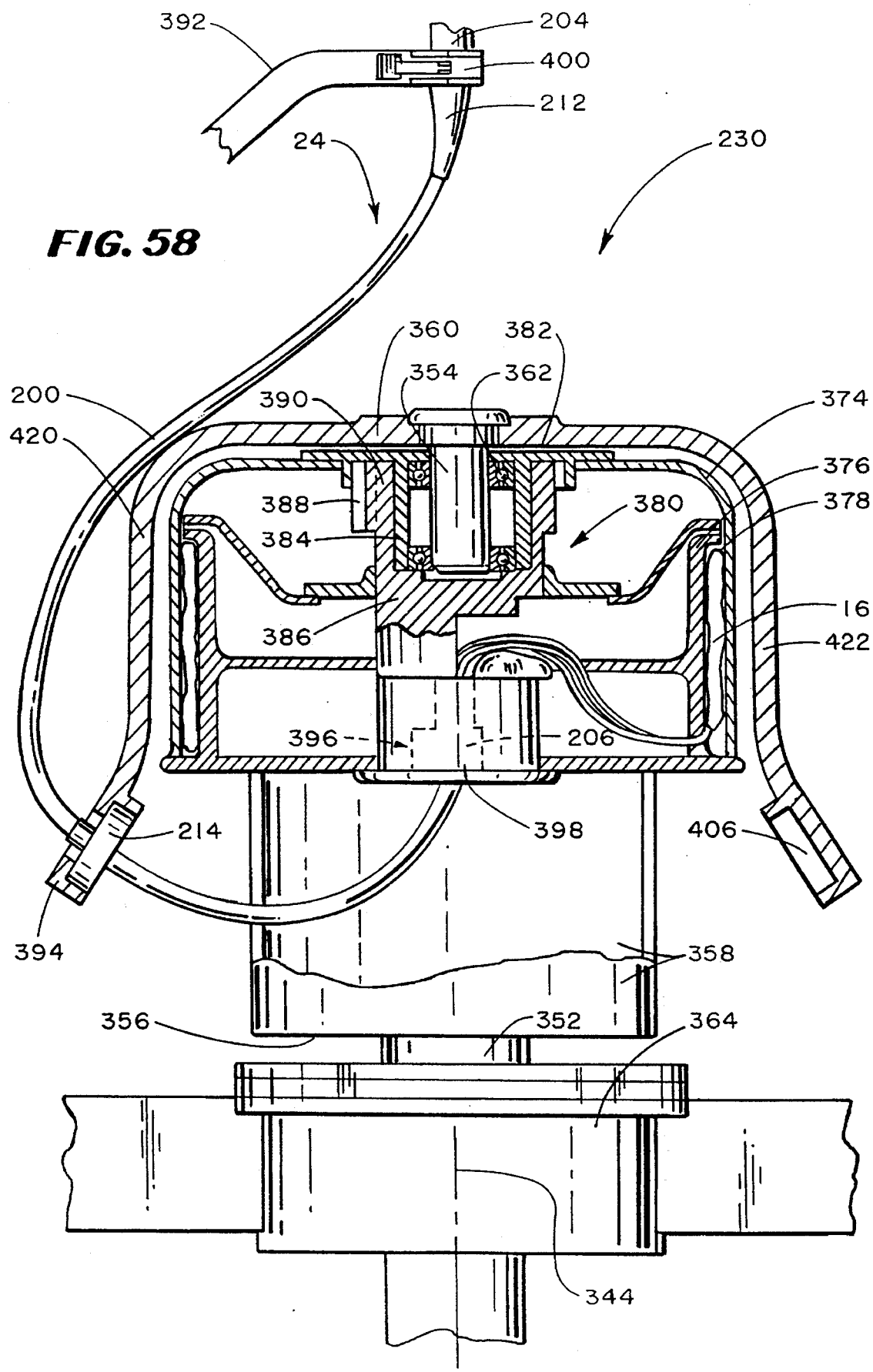
FIGS. 58 and 59 are side views of the centrifuge shown in FIG. 49, with the chamber assembly in its operating position, and the umbilicus of the fluid processing assembly held by upper, lower, and middle mounts for rotation.

The chamber assembly 350 is attached to the second axle 354, which spins on a bearing element 366 in the yoke cross member 360 (see FIG. 58, also).

As FIG. 49 shows, one end of the yoke cross member 360 is mounted by a pivot hinge 368 to a yoke arm 358. The yoke cross member 360 and the chamber assembly 350 attached to it pivot as a unit about the hinge 368 between an operating position (shown in FIG. 49) and a loading position (shown in FIGS. 50 and 51).

Figure 53:
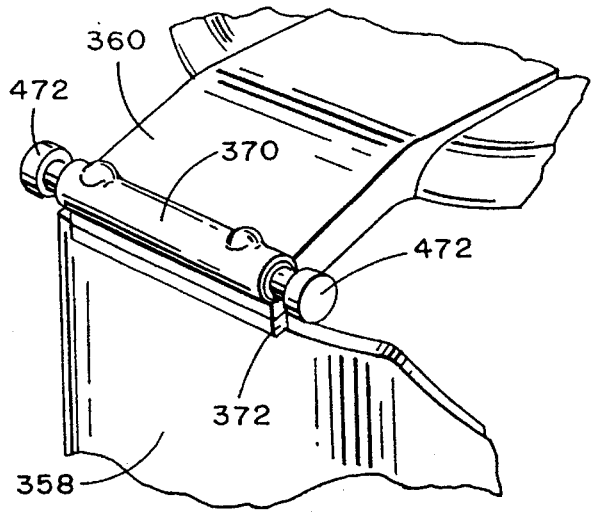
FIGS. 53 and 54 are enlarged perspective views of the latch and receiver elements associated with chamber assembly, with the elements shown latched together in FIG. 53 and unlatch apart in FIG. 54.
Figure 54:
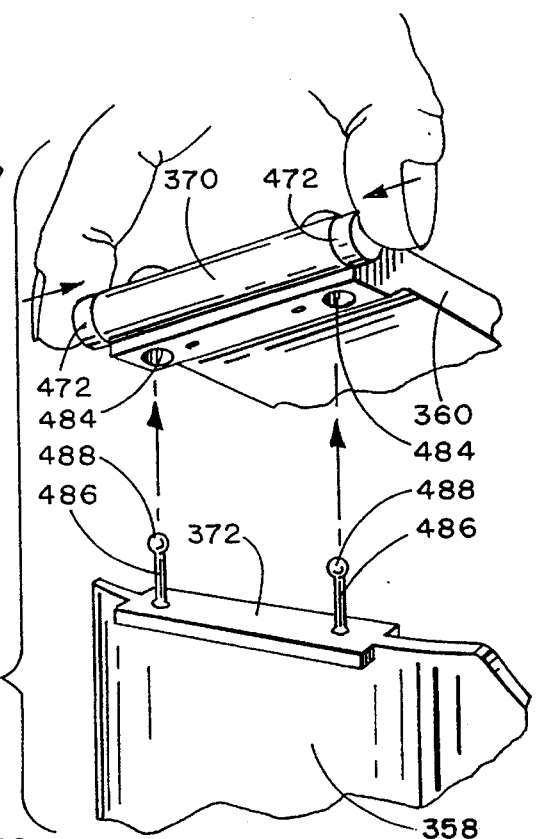

When in the operating position (see FIG. 49), the chamber assembly 350 assumes a downward facing, suspended orientation on the yoke cross member 360. The other end of the yoke cross member 360 includes a latch 370 that mates with a latch receiver 372 on the other yoke arm 358 (see FIGS. 53 and 54, also). The latch 370 and receiver 372 releasably lock the yoke cross member 360 in the operating position (as FIG. 53 shows).

Freeing the latch 370 from the receiver 372 (see FIG. 54) allows the user to pivot the yoke cross member 360 into the loading position. In this position (see FIGS. 50 and 51), the chamber assembly 350 assumes an upward facing orientation.

The latch 370 and receiver 372 can be constructed in various ways. In the illustrated and preferred embodiment (see FIGS. 55 to 57), the latch 370 comprises an opposed pair of push knobs 472 held by pins 474 within slide bushings 476 within the latch 370. The knobs 472 are movable within the bushings 476 between an outward position (shown in FIG. 56) and a inward position (shown in FIG. 57). A compression spring 478 biases the knobs 472 toward their outward position. Manually squeezing the knobs 472 toward each other (see FIG. 54) moves the knobs 472 into their inward position.

Figure 55:
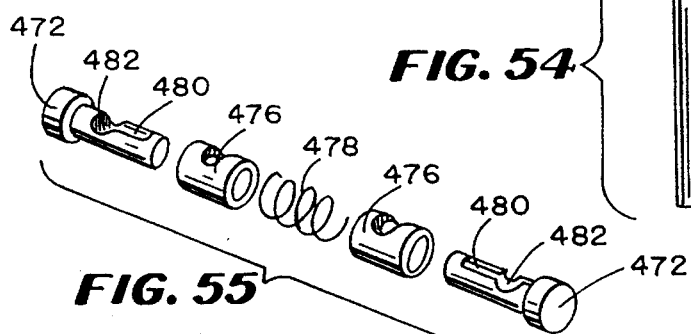
FIG. 55 is an exploded perspective view of the latch element shown in FIGS. 53 and 54.

The knobs 472 each include an axial surface groove 480 with a recessed detente 482 (see FIG. 55). When the knobs 472 are squeezed into their inward position (see FIG. 57), the each detente 482 registers with a latch hole 484. When aligned, the detente 482 and hole 484 accommodates passage of the latch tip 488 of a latch pin 486 on the receiver 372.

Figure 56:
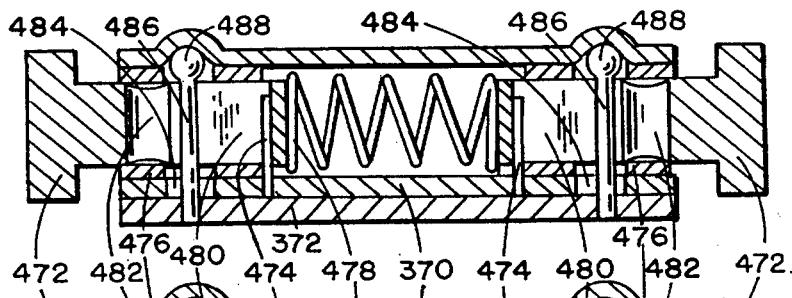
FIGS. 56 and 57 are enlarged side section views of the latch and receiver elements shown in FIGS. 53 and 54, with the elements shown latched together in FIG. 56 and unlatched and apart in FIG. 57.
Figure 57:
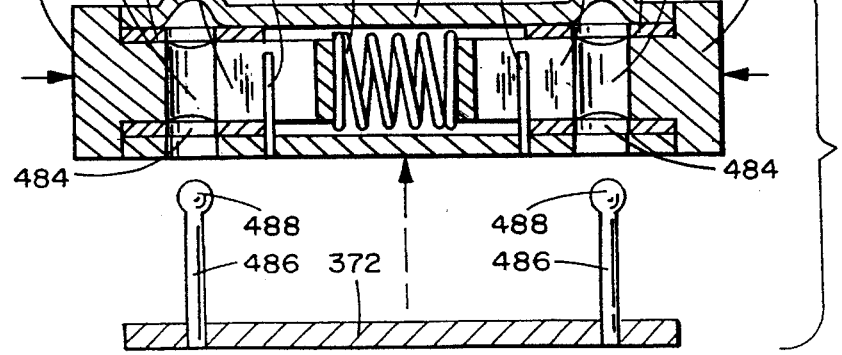

When released, the spring 478 returns the knobs 472 to their outward position (see FIG. 56). Each groove 482 registers with the hole 484 preventing passage of the latch tip 488. This locks the latch 370 and receiver 372 together, until the knobs 472 are again manually squeezed into their inward position to free the latch tip 488.

Figure 74:
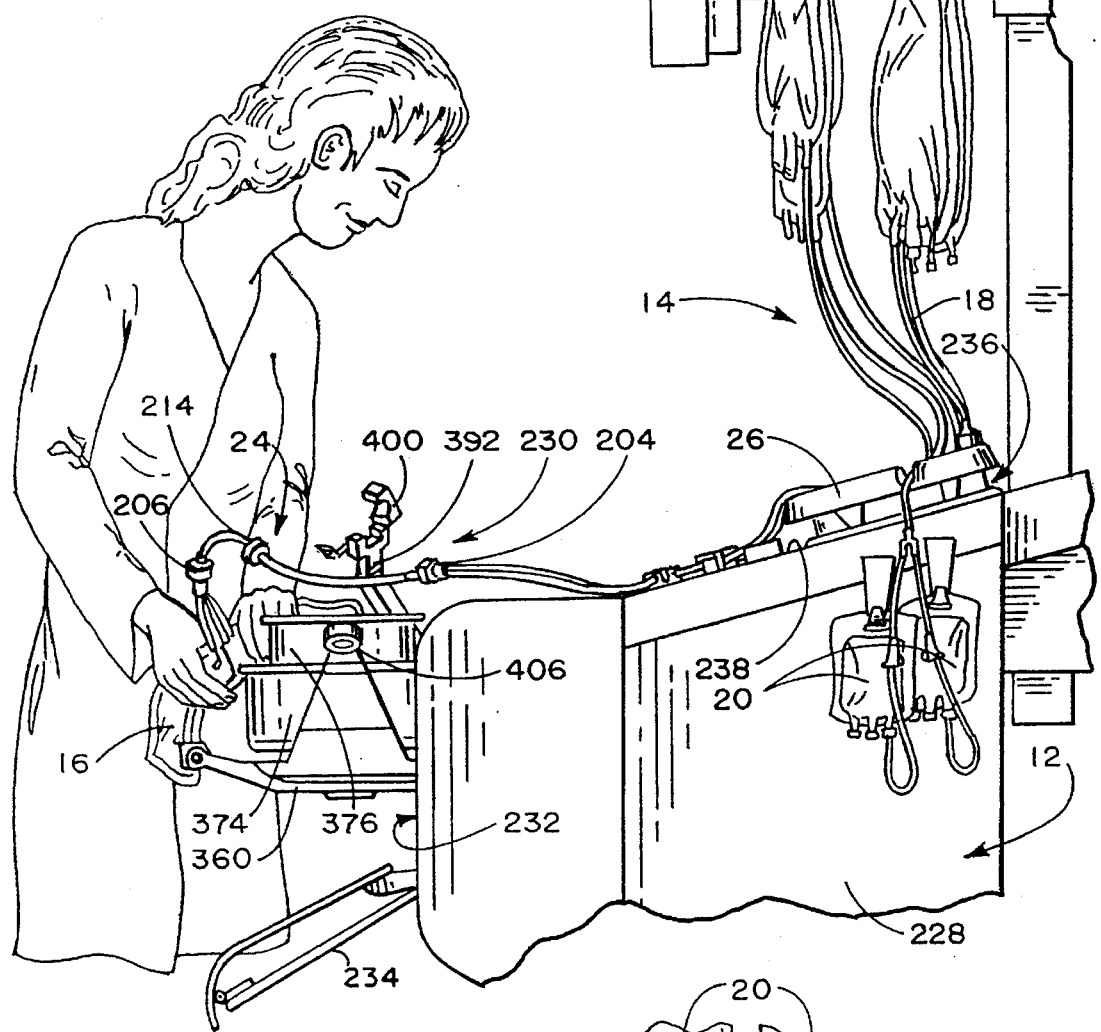

Because of the angled orientation of the centrifuge, opening the door 234 presents the yoke cross member 360 to the typical user at his/her waist level (as FIG. 74 shows). The user can open the door 234 and, without bending or stooping, squeeze the knobs 472 to release and then pivot the yoke cross member 360 and attached chamber assembly 350 out of the compartment 232. This places the chamber assembly 350 into its upward facing orientation, which is also at the typical user's waist level.

As FIGS. 51 and 52 show, with the chamber assembly 350 in its upward facing orientation, the user can open the entire processing chamber assembly 350 to load and unload of the disposable processing chamber 16. In the illustrated embodiment, the distance (D4 in FIG. 21A) between the horizontal support plane 452 and the top of the processing chamber assembly 350, when opened for loading, is about 29 inches.

For this purpose (see FIG. 52), the chamber assembly 350 includes a rotating outer bowl 374. The bowl 374 carries an inner spool 376. An arcuate channel 378 (see FIGS. 52 and 58) extends between the exterior of the inner spool 376 and the interior of the outer bowl 374. When wrapped about the spool 376, the processing chamber 16 occupies this channel 378.

The chamber assembly 350 includes a mechanism 380 for moving the inner spool 376 telescopically out of the bowl 374. This allows the user to wrap the processing chamber 16 about the spool 376 before use and to unwrap and remove the processing chamber 16 from the spool 376 after use.

The mechanism 380 can be variously constructed. In the illustrated embodiment (as FIG. 58 best shows), the outer bowl 374 is coupled to the second axle 354 through a plate 382. The plate 382 includes a center hub 384 that surrounds the second axle 354 and that, like the plate 382, rotates on the second axle 354.

The inner spool 376 also has a center hub 386 that telescopically fits about the plate hub 384. A key 388 connects the inner spool hub 386 to the plate hub 384 for common rotation on the second axle 354. The key 388 fits in elongated keyway 390 in the plate hub 384, so that the entire inner spool 376 can be moved along the axis of the plate hub 384 into and out of the bowl 374.

In this arrangement, the inner spool 376 is movable along the second axle 354 between a lowered operating position within the outer bowl 374 (as FIGS. 49 and 58 show) and an uplifted loading position out of the outer bowl 374 (as FIG. 52 shows).

Further details of the chamber assembly are found in copending U.S. patent application Ser. No. 07/814,403, filed Dec. 23, 1991, and entitled "Centrifuge with Separable Bowl and Spool Elements Providing Access to the Separation Chamber," which is incorporated herein by reference.

(iii) The Centrifuge-Umbilicus Interface

Figure 59:
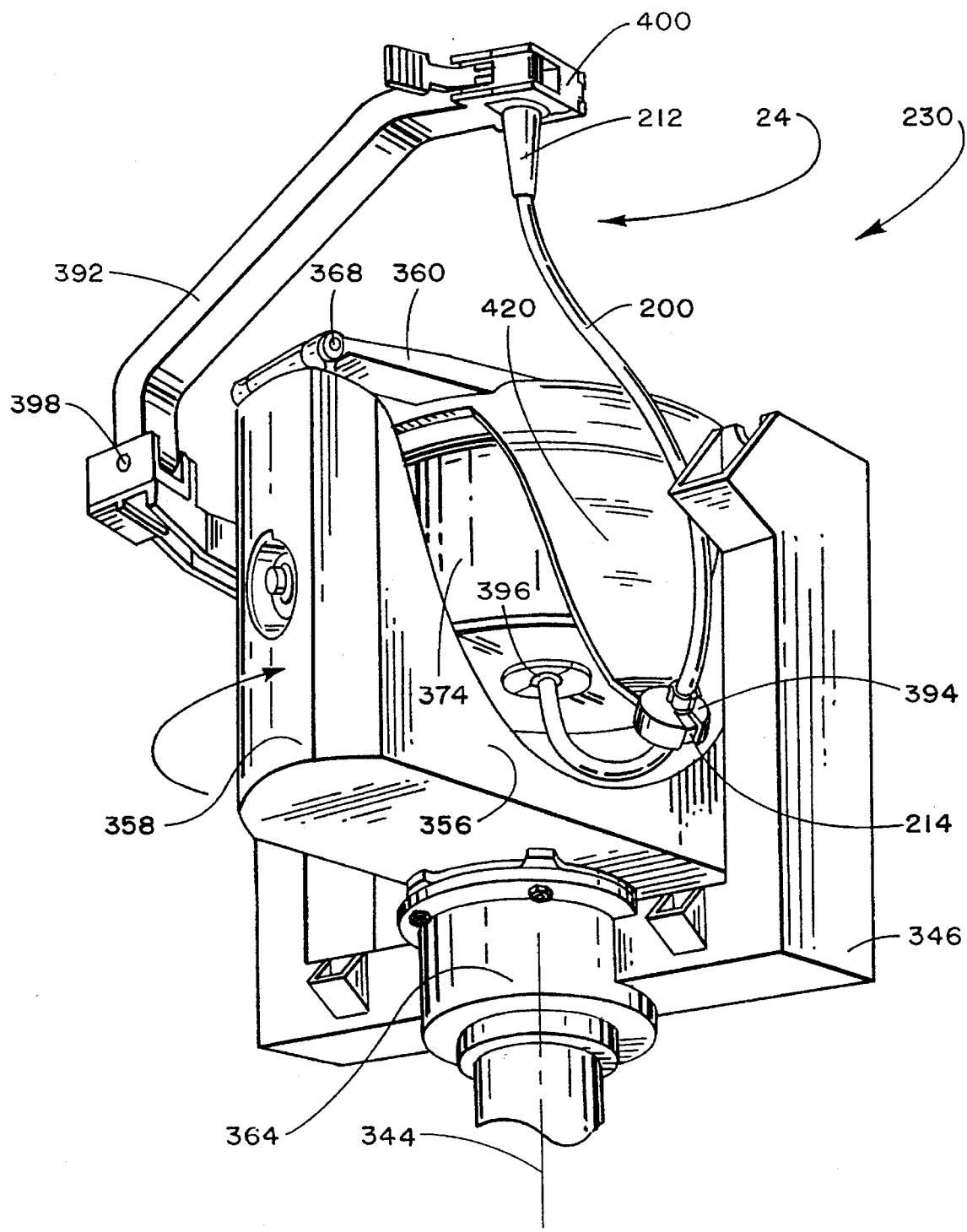

As FIGS. 58 and 59 best show, the centrifuge 16 includes three umbilicus mounts 392, 394, and 396 positioned at spaced apart positions on the centrifuge 16. The mounts 392 and 396 receive the umbilicus supports 204 and 206. The mount 394 receives the umbilicus thrust bearing member 214.

As FIGS. 58 and 59 show, the mounts 392, 394, and 396 hold the umbilicus 24 in a predetermined orientation during use, which resembles an inverted question mark.

The uppermost umbilicus mount 392 is located at a nonrotating position above the chamber assembly 350 (see FIG. 21, too). A pin 398 (see FIG. 59) attaches the proximal end of the upper umbilicus mount 392 to the stationary platform 346. The upper mount 392 pivots on this pin 398 between an operating position (shown in solid lines in FIG. 49 and 59) and a loading position (shown in phantom lines in FIG. 49).

Figure 50:
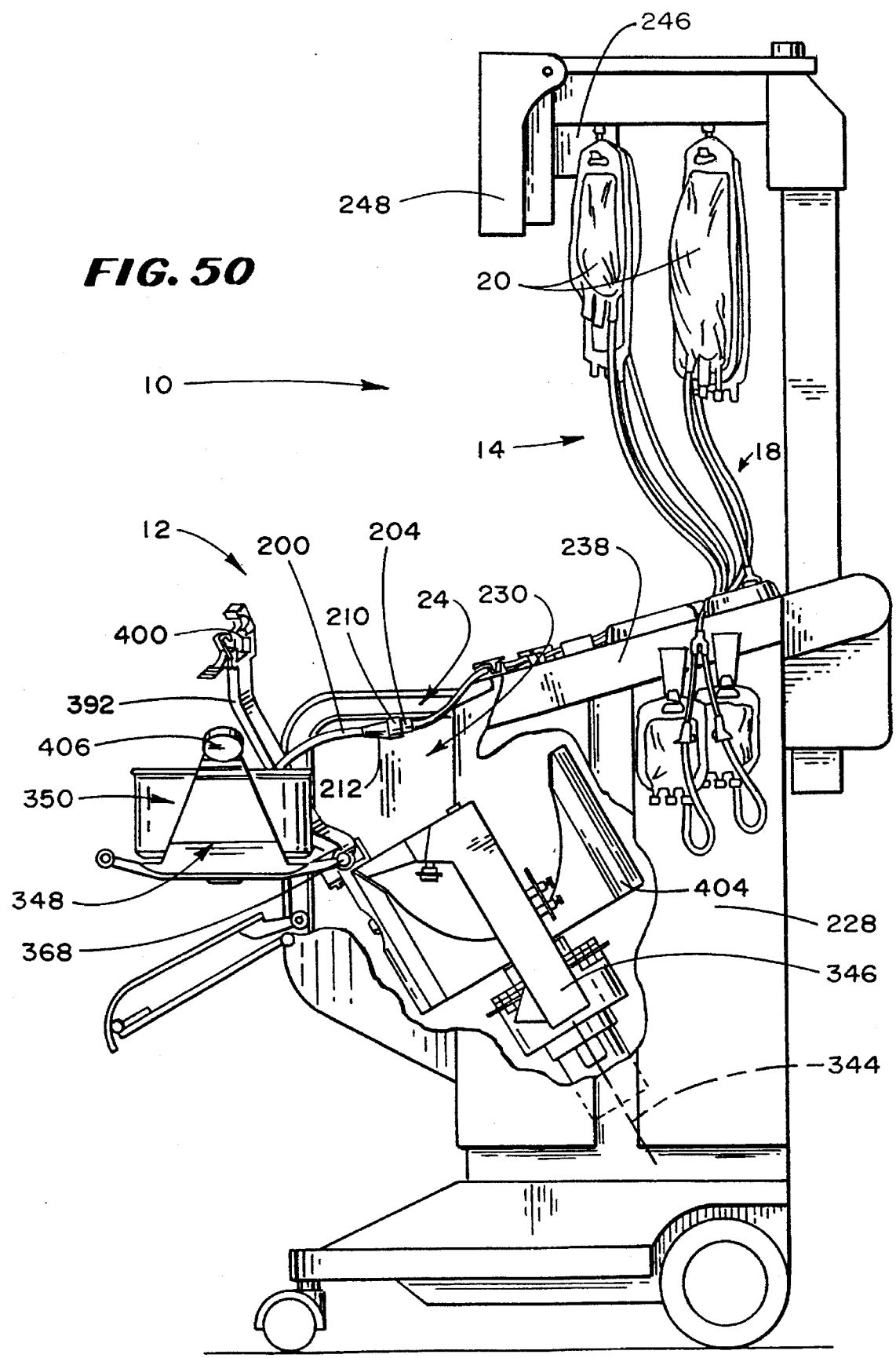
FIG. 50 is a side elevation view of the centrifuge assembly shown in FIG. 1, with portions being broken away to show the interior compartment housing the centrifuge (also shown in FIG. 49), with the associated chamber assembly being shown in its loading position.

In the operating position (see FIG. 59), the distal end of the upper mount 392 is aligned with the rotational axis of the chamber assembly 350. In the loading position (as shown in FIGS. 50 and 51), the distal end is pivoted out of the way, to facilitate loading and unloading the umbilicus 24. The upper mount 392 can be manually locked for use in the operating position using a conventional over-center toggle mechanism (not shown) or the like.

The upper mount includes an over-center clamp 400 on its distal end. As FIGS. 60 to 62 best show, the clamp 400 includes cooperating first and second clamp members 412 and 414 pivotally attached to a clamp base 416. The clamp members 412 and 414 swing open to receive the upper umbilicus support member 204 (see FIG. 60) and swing close to capture the flange 210 on the support member 204. The interior surfaces of the clamp members 412 and 414 and base 416 are configured in a D-shape that, when closed, mates with the D-shape of the flange 210. The clamp member 414 carries an over-center latch 418 that locks the members 412 and 414 closed. When closed, the upper mount 392 holds the upper portion of the umbilicus 24 against rotation in a position aligned with the rotational axis of the chamber assembly 350.

Figure 64:
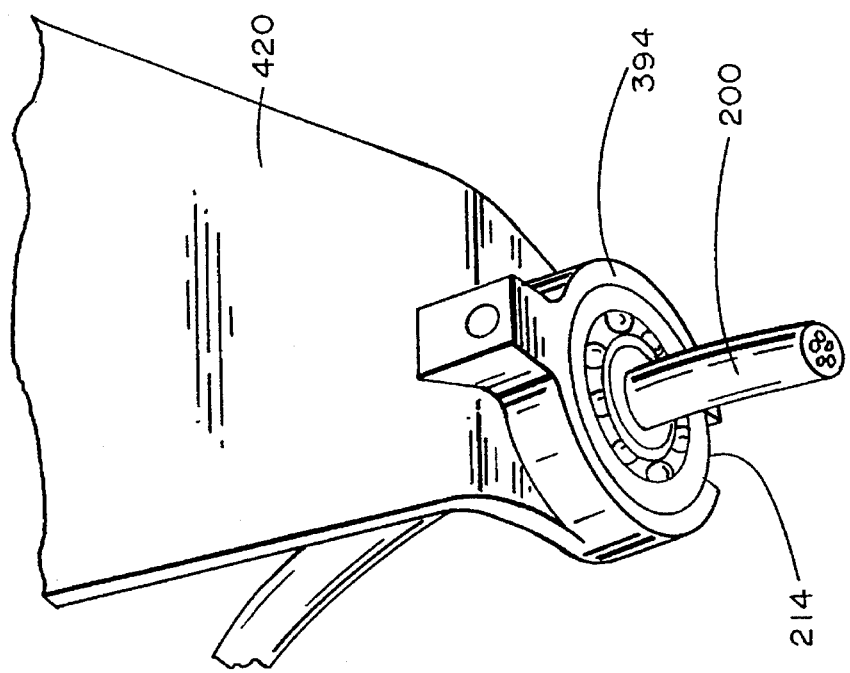
FIGS. 63 and 64 show the middle umbilicus mount in association with the umbilicus thrust bearing member.
Figure 63:
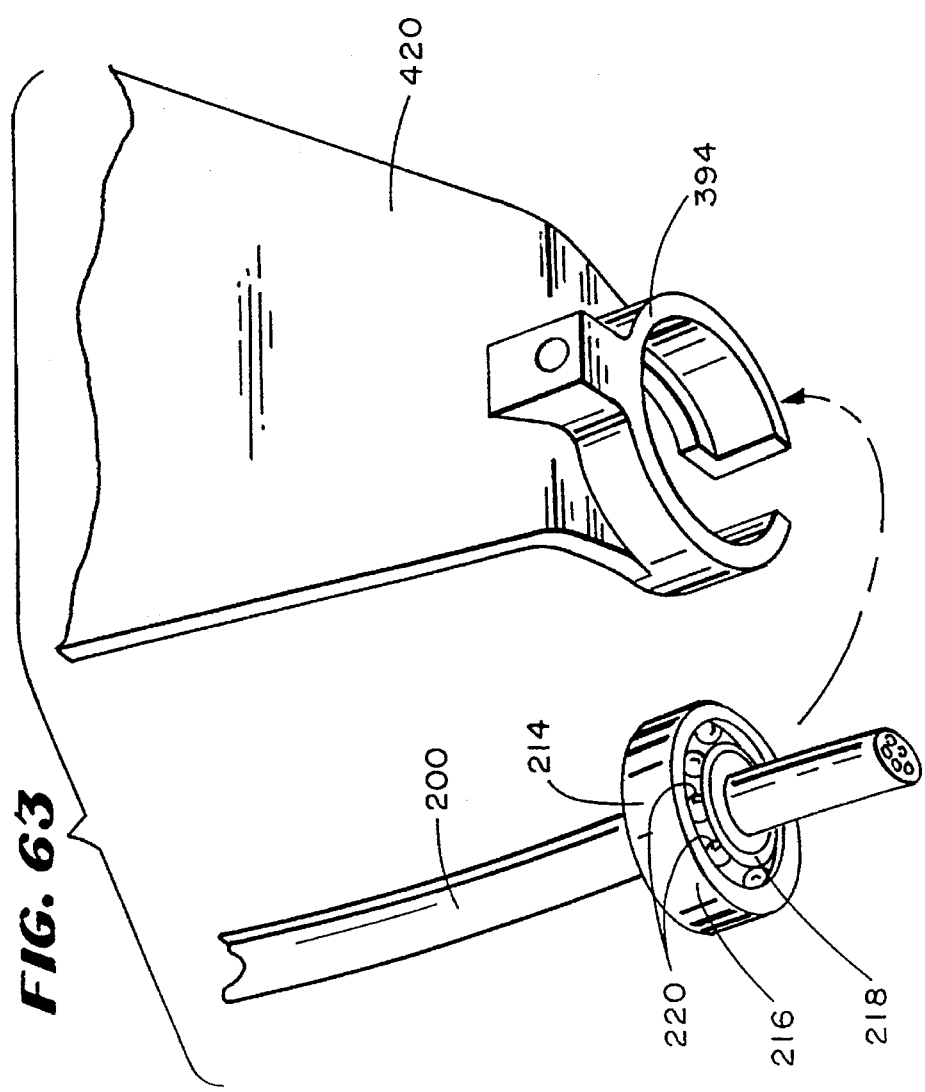

A yoke assembly 348 includes a wing plate 420 that carries the middle umbilicus mount 394 (see FIG. 59). As FIGS. 63 and 64 further show, the mount 394 takes the form of an aperture that receives the thrust bearing member 214 carried by the umbilicus 24. The thrust bearing member 214 attaches in a secure snap fit within the aperture mount 394. This connection allows the umbilicus 24 to rotate, or roll, about the thrust bearing member 214 as the yoke rotates about the first axle 352, but otherwise secures the umbilicus 24 to the yoke assembly 348.

The yoke assembly 348 includes another wing plate 422 diametrically spaced from the wing plate 420. The wing plate 422 carries a counterweight 406, to counter balance the umbilicus mount 394.

The lowermost umbilicus mount 396 holds the lowermost support member 206 carried by the umbilicus 24. As FIGS. 65 to 67 best show, the lower mount 396 includes a clamp 402 that is fastened to the spool hub 386 for common rotation about the second axle 354. The clamp 402 also rides with the spool 376 along the plate hub 384 as the spool is raised and lowered between its lowered operating position and its uplifted loading position.

As FIGS. 51 and 52 show, the lower umbilicus mount 396 is presented to the user when the chamber assembly 350 occupies upward facing orientation and the spool 376 is lifted into its loading position.

Figure 65:
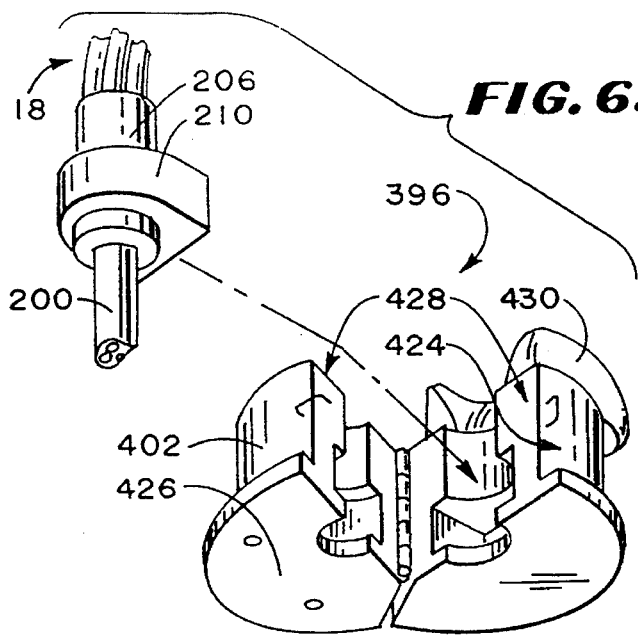
FIGS. 65 to 68 show the lower umbilicus mount in association with the lower umbilicus support member.
Figure 66:
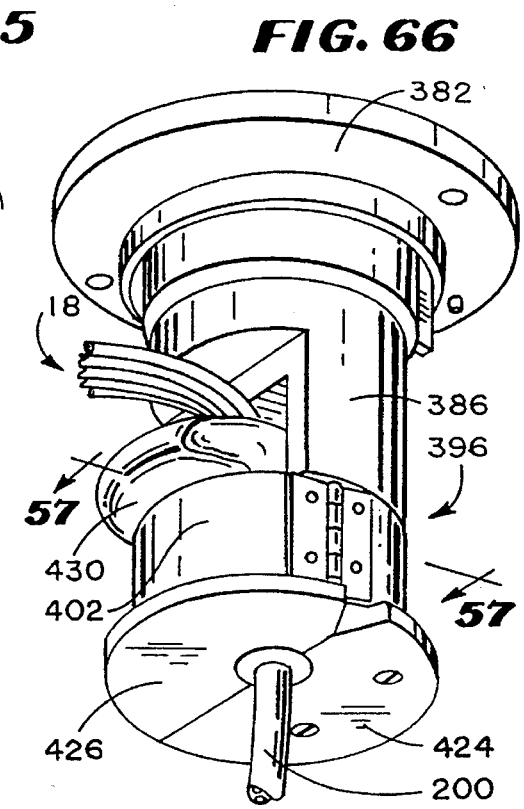
Figure 67:
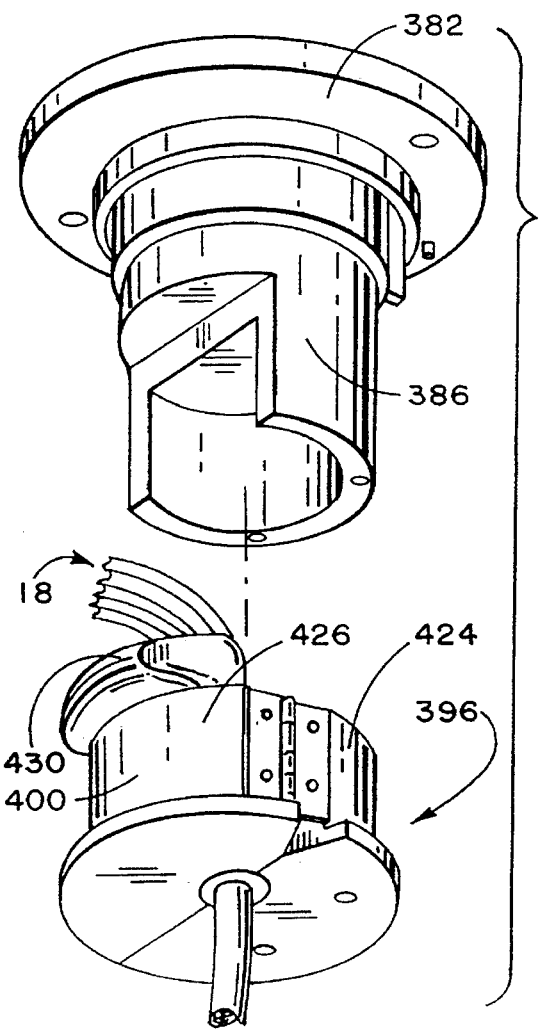
Figure 68:
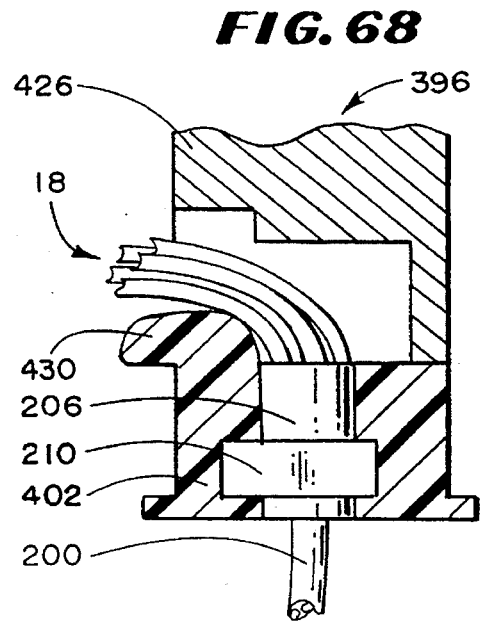

The clamp 402 includes hinged clamp members 424 and 426 (see FIGS. 65 to 67). The members 424 and 426 open to receive the lower umbilicus support 206 (as FIG. 65 shows) and close to capture the mount 206 (as FIGS. 66 and 67 show.

The interior of the clamp members 424 and 426 are configured in a D-shape to mate with the D-shape of the flange 210 carried by the lower umbilicus support 206. A latch assembly 428 (see FIG. 65) locks the members 424 and 426 during use.

The lower mount 396 holds the lower portion of the umbilicus 24 in a position aligned with the rotational axis of the second axle 354 (see FIG. 59). The mount 396 grips the lower umbilicus support 206 to rotate with the lower portion of the umbilicus 24.

In the illustrated and preferred embodiment, the lower mount 396 includes beveled support plate 430. As FIG. 64 best shows, the plate 430 supports the tubing 18 as it extends from the lower umbilicus support 206 and bends toward the processing chamber 16. The support plate 430 prevents crimping of the tubing 18 as it makes this transition.

The upper mount 392 holds the upper portion of the umbilicus 24 in a non-rotating position above the rotating yoke assembly 348. Rotation of the yoke assembly 348 imparts rotation to the umbilicus about the thrust bearing member 214 held by the middle mount 394. Rotation of the umbilicus 24, in turns, imparts rotation through the lower mount to the chamber assembly 350.

For every 180° of rotation of the first axle 352 about its axis (thereby rotating the yoke assembly 348 180°) the umbilicus 24 will roll or twirl 180° in one direction about its axis, due to the fixed upper mount 392. This rolling component, when added to the 180° rotating component, will result in the chamber assembly 350 rotating 360° about its axis.

The relative rotation of the yoke assembly 348 at a one omega rotational speed and the chamber assembly 350 at a two omega rotational speed, keeps the umbilicus 24 untwisted, avoiding the need for rotating seals.

Further details of this arrangement are disclosed in Brown et al U.S. Pat. No. 4,120,449, which is incorporated herein by reference.

(iv) Umbilicus Orientation

The centrifuge 230 made and operated according to the invention provides a small, compact operating environment. The compact operating environment leads to rates of rotation greater than those typically encountered in conventional blood centrifuges.

For example, a conventional CS-3000® Blood Cell Separator manufactured and sold by Baxter Healthcare Corporation (Fenwal Division) operates at centrifuge speed of between zero and about 1600 RPM. On the other hand, the centrifuge 230 made and operated according to the invention can be operated at speeds of upwards to 4000 RPM.

In this high speed operating environment, the umbilicus 24 is subjected to significant cyclical flexure and stretching while spinning at high speeds.

As before described, as the umbilicus 24 and the yoke assembly 348 spin 360°, the main body 200 of the umbilicus 24 rolls or twirls one rotation about its axis. At the same time, centrifugal force pulls outward on the umbilicus 24 as it rotates with the yoke assembly 348.

These rolling and pulling forces generate localized stress on the upper support member 204, which is held stationary by the umbilicus mount 392. To moderate this localized stress, the umbilicus 24 includes the tapered strain relief sleeve 212. The tapered sleeve 212 helps to maintain a desired operating curvature in the upper region of the umbilicus 24, keeping the umbilicus 24 from buckling, twisting, and ripping apart.

The following Table 1 shows the effect of the tapered sleeve 212 in moderating stress, based upon a mathematical model using the commercially available ABAQUS™ finite element code.

TABLE 1

EFFECT OF TAPERED STRAIN RELIEF SLEEVE

| $L^1$ | Sleeve$^2$ | | Stress$^3$ |
|---|---|---|---|
| 14" | None | | Failure |
| 14" | No Taper | 1.5" | 1115 psi |
| 14" | No Taper | 2.0" | 1302 psi |
| 14" | No Taper | 3.0" | 1472 psi |
| 14" | No Taper | 3.5" | Failure |
| 14" | Tapered | 1.0" | 1154 psi |
| 14" | Tapered | 1.5" | 765 psi |
| 14" | Tapered | 2.0" | 833 psi |

Figure 69:
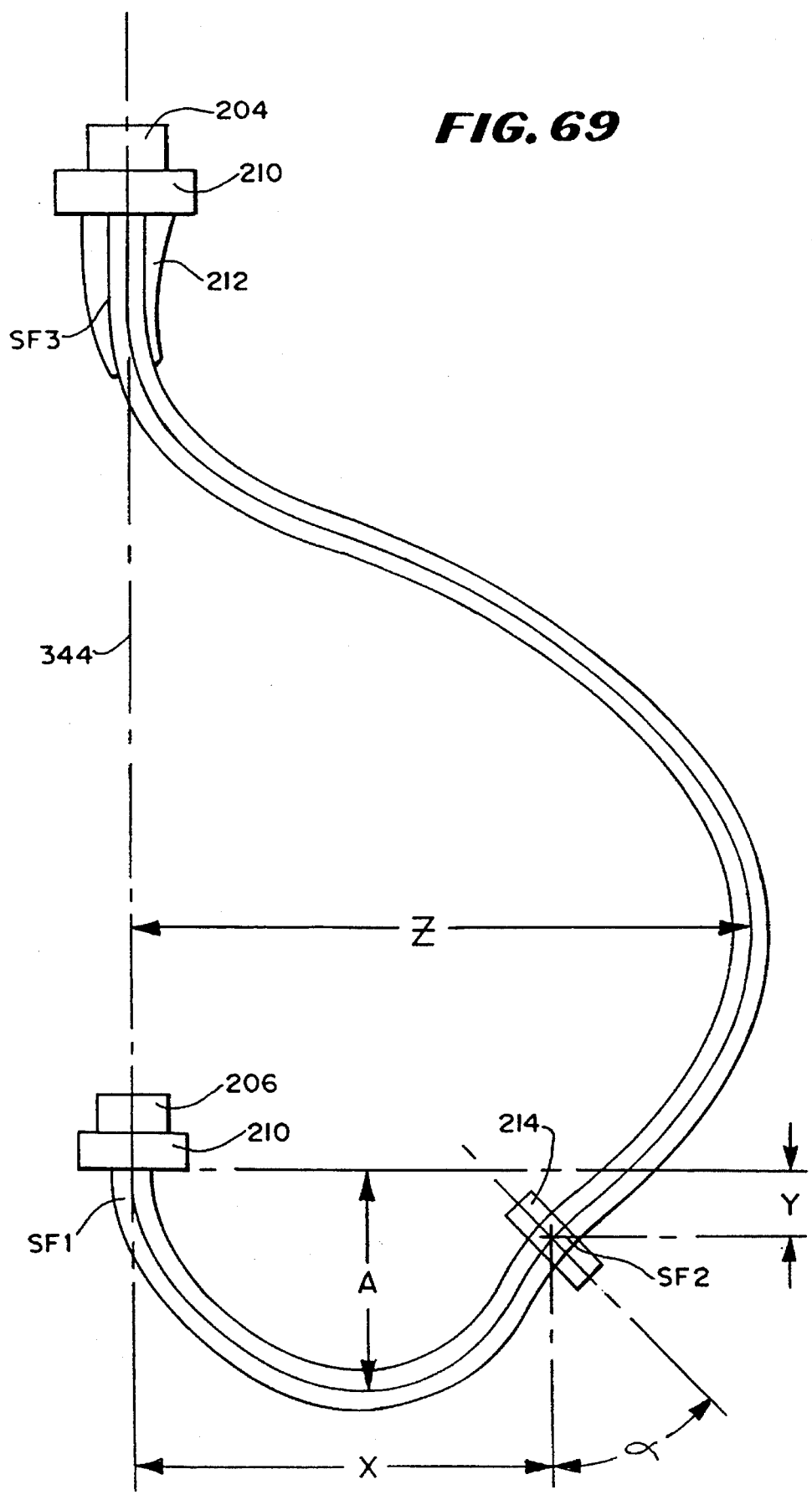
FIG. 69 is a diagrammatic view of the umbilicus when held by the centrifuge mounts in the desired orientation for use.

Notes:
The mathematical model assumed:
1. A coextruded multilumen umbilicus (5 lumens) was made of Hytrel ® 4056 Plastic Material. It was attached to a centrifuge generally as shown in FIG. 69, which was rotated at 2000 RPM. In Table 1, "L" designates the overall length of the umbilicus, in inches.
2. The umbilicus included an upper and lower support member 204 and 206, each made of Hytrel ® 8122 Plastic Material. The umbilicus did not carry a thrust bearing member 214. Each upper and lower support member included either (i) no strain relieve sleeve 214 (designated "None" in Table 1); (2) a strain relief sleeve 214 of constant wall thickness (designated "No Taper" in Table 1); or (3) a tapered strain relief sleeve 214 (designated "Tapered" in Table 1). The strain relief sleeve, when used, measured 0.625" in maximum outer diameter, with a maximum wall thickness of 0.030". The sleeves 214 ranged in length between 1.0" to 3.5", as indicated.
3. Stresses (in psi) indicated the maximum von Mises stresses measured along the umbilicus. In Table 1, "Failure" indicated that the umbilicus buckled at 2000 RPM.

Table 1 demonstrates that, in the absence of any strain relief sleeve (tapered or otherwise), the umbilicus buckled at 2000 RPM. The presence of a strain relief sleeve prevented this type of failure. Table 1 also demonstrates that a tapered strain relief sleeve significantly reduced the measured stress, compared to a nontapered sleeve.

The rolling and pulling forces on the umbilicus also develop localized stress on the lower support member 206, which rotates with the lower umbilicus mount 396. The umbilicus 24 includes the thrust bearing member 214 to moderate stress localized in this region. The thrust bearing member 214 allows the umbilicus 24 to roll or twirl with rotation, thereby providing long term, high speed performance. The thrust bearing member 214 maintains a desired operating curvature in the lower region of the umbilicus to equalizes the stress load, preventing the build up of high stress conditions in the region of the lower support member 206.

The following Table 2 shows the effect of the rotating thrust bearing member 214 on the moderating stress along the umbilicus, based upon the same mathematical model.

TABLE 2

EFFECT OF ROTATING THRUST BEARING

| Length Above/Below$^1$ | Upper Support/ Stain Relief$^2$ | Stress$^3$ |
|---|---|---|
| 11.5"/5" | Tapered 1" | 818 psi |
| 11.5/5" | Tapered 1.5" | 589 psi |
| 11"/5" | Tapered 1" | 781 psi |
| 11"/5" | Tapered 1.5" | 564 psi |

Notes:
The mathematical model assumed:
1. A coextruded multilumen umbilicus (5 lumens) was made of Hytrel ® 4056 Plastic Material. It was attached to the centrifuge as shown in FIG. 69 and rotated at 2000 RPM. In Table 2, "Above" designates the overall length of the umbilicus, in inches, measured from the upper support member 204 to the thrust bearing element 214. In Table 2, "Below" designates the overall length of the umbilicus, in inches, measured from the lower support member 206 to the thrust bearing element 214.
2. The umbilicus included an upper and lower support member 204 and 206, each made of Hytrel ® 8122 Plastic Material. The upper support member 204 included a tapered strain relief sleeve, like that used in Table 1, ranging in length between 1.0" to 1.5", as indicated.
3. Stresses (in psi) indicated the maximum von Mises stresses measured.

When compared to Table 1, Table 2 demonstrates that the presence of a rotating thrust bearing element 214 leads to significantly reductions in the stress measured.

Furthermore, the location of the thrust bearing member 214 relative to the lower support member is important to maintaining the desired curvature of the umbilicus for stress reduction and long term performance. The magnitude of the thrust angle α of the member 214 (shown in FIG. 69) is also important to the moderation of stresses.

As FIG. 69 shows, rotation of the umbilicus localizes stress forces at three locations, designated SF1, SF2, and SF3. SF1 is located just below the lower support member 206; SF2 is located at the thrust bearing 214; and SF3 is located at the strain relief sleeve 212 of the upper support member 204.

Among these, the magnitude of SF1 is the most important. Here is where that the rolling motion of the umbilicus 24 and the one omega rotation of the yoke assembly 348 are translated into two omega rotation of the chamber assembly 350.

As the radial distance (X) shown in FIG. 69 between the rotational axis 344 and the thrust bearing member 214 increases, SF1 increases, and vice versa. It is therefore desirably to locate the thrust bearing member 214 close to the rotational axis, thereby reducing distance (X). However, as the radial distance (X) decreases, SF2 increases, and vice versa. Therefore, in selecting (X), a tradeoff between decreasing SF1 and increasing SF2 must be made. The thrust angle α of the member 214 must also be taken into account in the distribution of stresses.

As the axial distance (Y) shown in FIG. 69 between the bottom of the lower support element 206 and the thrust bearing member 214 decreases, SF1 increases, and vice versa. It is therefore desirably to locate the thrust bearing element 214 axially away from the bottom of the lower support member 206, thereby increasing the distance (Y). However, as the axial distance (Y) increases, SF2 increases, and vice versa. Therefore, in selecting (Y), a tradeoff between decreasing SF1 and increasing SF2 must again be made.

As distances (X) and (Y) change, so too do the radial distance (Z) and the axial distance (A) shown in FIG. 69. Distance (Z) is the maximum radial spacing between the axis of rotation 344 and the umbilicus 24. Distance (A) is the maximum axial spacing between the bottom of the lower support member 206 and the umbilicus 24.

Distances (A) and (Z) govern the clearance between the umbilicus 24 and the chamber assembly 350. These distances (Z) and (A) dictate the overall geometry and size of the space surrounding the chamber assembly 350.

In selecting an optimal design, the following criteria are considered important:

(1) Given the modulus of the umbilicus 24 made according to the illustrated and preferred embodiment, and factoring in a safety margin, the SF1 force on the umbilicus (expressed in terms of a von Mises stress) should not exceed about 564 pounds per square inch (PSI). This factor can, of course, vary according to the particular construction and materials used in making the umbilicus 24.

(2) Given the construction and materials of the thrust bearing member 214 made according to the illustrated and preferred embodiment, and again factoring a safety margin, the total load on the thrust bearing member 214 (as measured along the axis of the bearing member 214) should not exceed 10 pounds. This factor can, of course, vary according to the particular construction and materials used in making the thrust bearing member 214.

(3) Given that desired physical layout and dimensions of the centrifuge 230 should meet the criteria of portability and compactness, the distance (Z) should be less than about 5.5 inches. The distance (A) should be greater than about 0.25 inch to provide enough clearance about the bottom and sides of the rotating centrifuge 230 during use.

Table 3 summarizes the variations in stresses observed with changes in position and thrust angle α of the thrust bearing element 214 based upon the same mathematical model.

TABLE 3

STRESS VARIATIONS
WITH CHANGES IN THRUST BEARING ELEMENT
POSITION/ORIENTATION

| $L^1$ (in) | $X^2$ (in) | $Y^3$ (in) | $\alpha^4$ (0) | Loads Axial/Radial$^5$ (lbf) | Stress (psi)$^6$ |
|---|---|---|---|---|---|
| Bottom | | | | | |
| 5 | 4 1/16 | 1 | 30 | 2.22/1.13 | 603 |
| 5.25 | 4 1/16 | 1 | 45 | 2.07/1.61 | 596 |
| 5.25 | 4 1/16 | 1 | 40 | 2.24/1.53 | 565 |
| 5.25 | 4 1/16 | .75 | 35 | 2.42/1.44 | 557 |
| 5.25 | 4 1/16 | .5 | 30 | 2.59/1.30 | 565 |
| 5.25 | 4 1/16 | .75 | 30 | 2.59/1.31 | 528 |
| 5.25 | 4 1/16 | 1 | 30 | 2.57/1.30 | 505 |
| 5.25 | 4 1/16 | 1 | 55 | | 659 |
| Top | | | | | |
| 11.25 | 4 1/16 | 1 | 30 | 7.20/2.39 | 593 |
| 11 | 4 1/16 | 0 | 30 | 6.81/0.92 | 611 |
| 11 | 4 1/16 | .5 | 30 | 6.83/1.79 | 595 |
| 11 | 4 1/16 | 1 | 30 | 6.84/2.91 | 581 |
| 11 | 4 1/16 | 1 | 55 | | 578 |
| 10.75 | 4 1/16 | 1 | 30 | 6.49/3.54 | 604 |

TABLE 3-continued

STRESS VARIATIONS
WITH CHANGES IN THRUST BEARING ELEMENT
POSITION/ORIENTATION

| $L^1$ (in) | $X^2$ (in) | $Y^3$ (in) | $\alpha^4$ (0) | Loads Axial/Radial$^5$ (lbf) | Stress (psi)$^6$ |
|---|---|---|---|---|---|

Notes:
The mathematical model assumed:
1. A coextruded multilumen umbilicus (5 lumens) was made of Hytrel ® 4056 Plastic Material. It was attached to the centrifuge as shown in FIG. 69 and rotated at 2000 RPM. The umbilicus included an upper and lower support member 204 and 206, each made of Hytrel ® 8122 Plastic Material. The upper support member 204 also includes a tapered strain relief sleeve 214 as described in Table 1. In Table 3, "Bottom" designates the overall length of the umbilicus, in inches, measured from the lower support member 206 to the thrust bearing member 214. In Table 2, "Top" designates the overall length of the umbilicus, in inches, measured from the upper support member 204 to the thrust bearing member 214.
2/3/4. X, Y and angle α are designated in FIG. 69.
5. The load calculations were performed for the top and bottom umbilicus regions separately. Therefore, the total load on the thrust bearing member 214 is the sum of the loads from the top and bottom umbilicus regions.
6. Stresses (in psi) indicated maximum von Mises stresses measured at the upper support member 204 (for the top umbilicus region) and at the lower support member 206 (for the bottom umbilicus region).

Table 3 shows that, for an umbilicus having a total overall length of 16.25", it should have an 11" top region and a 5.25" bottom region, and the thrust bearing member 214 should be oriented to provide a Distance (X) of 4 1/16; a Distance (Y) of 1.0"; and a thrust angle α of 30°. This configuration yielded the lowest maximum tubing stress of 581 psi. The total axial load of 9.41 lbf (6.84+2.57) was close to the design limit of 10 lbf.

Table 4 is another summary of the variations in stresses observed with changes in position and thrust angle α of the thrust bearing member 214 based upon the same mathematical model.

TABLE 4

STRESS VARIATIONS
WITH CHANGES IN THRUST BEARING ELEMENT
POSITION/ORIENTATION

| $L^1$ (in) | $X^2$ (in) | $Y^3$ (in) | $\alpha^4$ (0) | Loads Axial/Radial$^5$ (lbf) | Stress (psi)$^6$ |
|---|---|---|---|---|---|
| Top/Bottom | | | | | |
| 11/5.25 | 4 1/16 | .546 | 53.2 | 6.85/2.38 | 727 |
| 10.75/5.25 | 4 1/16 | .546 | 55.9 | 6.60/2.24 | 747 |
| 11/5 | 4 1/16 | .546 | 48.3 | 6.76/1.51 | 830 |
| 11.25/5 | 4 1/16 | .546 | 46.0 | 7.03/1.65 | 812 |
| 11.25/5.25 | 4 1/16 | .546 | 50.7 | 7.13/2.49 | 709 |
| 10.75/5 | 4 1/16 | .546 | 51.0 | 6.51/1.36 | 850 |
| 11.5/5.25 | 4 1/16 | .546 | 48.5 | 7.43/2.58 | 693 |
| 11/5.25 | 4 | .546 | 53.8 | 6.81/2.54 | 690 |
| 10.75/5.25 | 4 | .546 | 56.4 | 6.57/0.55 | 710 |
| 11.25/5 | 4 | .546 | 46.7 | 7.04/0.69 | 766 |
| 11.25/5.25 | 4 | .546 | 51.3 | 7.10/0.63 | 672 |
| 11/5.25 | 4 1/16 | .5 | 53.1 | 6.82/2.45 | 733 |
| 11/5.25 | 4 | .5 | 53.6 | 6.79/2.58 | 696 |

Notes:
The mathematical model assumed:

TABLE 4-continued

STRESS VARIATIONS
WITH CHANGES IN THRUST BEARING ELEMENT
POSITION/ORIENTATION

| L[1] (in) | X[2] (in) | Y[3] (in) | α[4] (0) | Loads Axial/ Radial[5] (lbf) | Stress (psi)[6] |
|---|---|---|---|---|---|

1. A coextruded multilumen umbilicus (5 lumens) was made of Hytrel ® 4056 Plastic Material. It was attached to the centrifuge as shown in FIG. 69 and rotated at 1800 RPM. The umbilicus included an upper and lower support member 204 and 206, each made of Hytrel ® 8122 Plastic Material. The upper support member 204 included a tapered strain relief sleeve 214. In Table 4, "Bottom" designates the overall length of the umbilicus, in inches, measured from the support member to the thrust bearing element. In Table 4, "Top" designates the overall length of the umbilicus, in inches, measured from the upper support member to the thrust bearing member 214.
2/3/4. X, Y and angle α are designated in FIG. 69.
5. The load calculations were performed by analyzing the entire umbilicus together, instead for the top and bottom umbilicus regions separately. Unlike the configuration described in Table 3, in Table 4, the thrust bearing member 214 was left free assume its own thrust angle α during rotation.
6. Stresses (in psi) indicated the maximum von Mises stresses measured at the lower support member.

In Table 4, all loads on the thrust bearing member 214 were below the design limit of 10 lbf. The trust bearing member 214 location where Distance (Y)=0,546"; Distance (X)=4"; and thrust angle α =51.3°; and where the top umbilicus region was 11.25" and the bottom umbilicus region was 5.25", gave the lowest maximum von Mises stress of 672 psi. However, for this umbilicus configuration, the radial distance (Z) was 5.665", which exceeded the design limit of 5.5". For this reason, the orientation with the next lowest stress giving a radial Distance (Z) less that 5.5" was chosen, as italicized in Table 4.

Comparing Tables 3 and 4, it can be seen that fixing the thrust angle α instead of allowing the thrust bearing member 214 to assume a thrust angle α during rotation can reduce the maximum stress, although fixing the thrust angle α may increase the axial load of the bearing member 214.

In a preferred structural embodiment, the main body 200 of the umbilicus 24 measures 16.75 inches end to end. The overall length of the umbilicus 24, measured between the top and bottom block members 204 and 206 is 17.75 inches. The distance between the bottom block 206 and the thrust bearing member 214 is 5 3/32 inches. In use, the Dimension (X) is 4.0 inch; the Distance (Y) is 0.546 inch; the Distance (Z) about 5.033 inches. The length of the tapered sleeve 212 is 1.8 inch. In the preferred arrangement, the thrust bearing member 214 is fixed at a thrust angle α during rotation of 53.8°.

III. SET-UP AND DISPOSAL OF SYSTEM

FIGS. 70 to 75 show the details of loading a representative processing assembly 14 on the centrifuge 16.

Figures 70, 71:
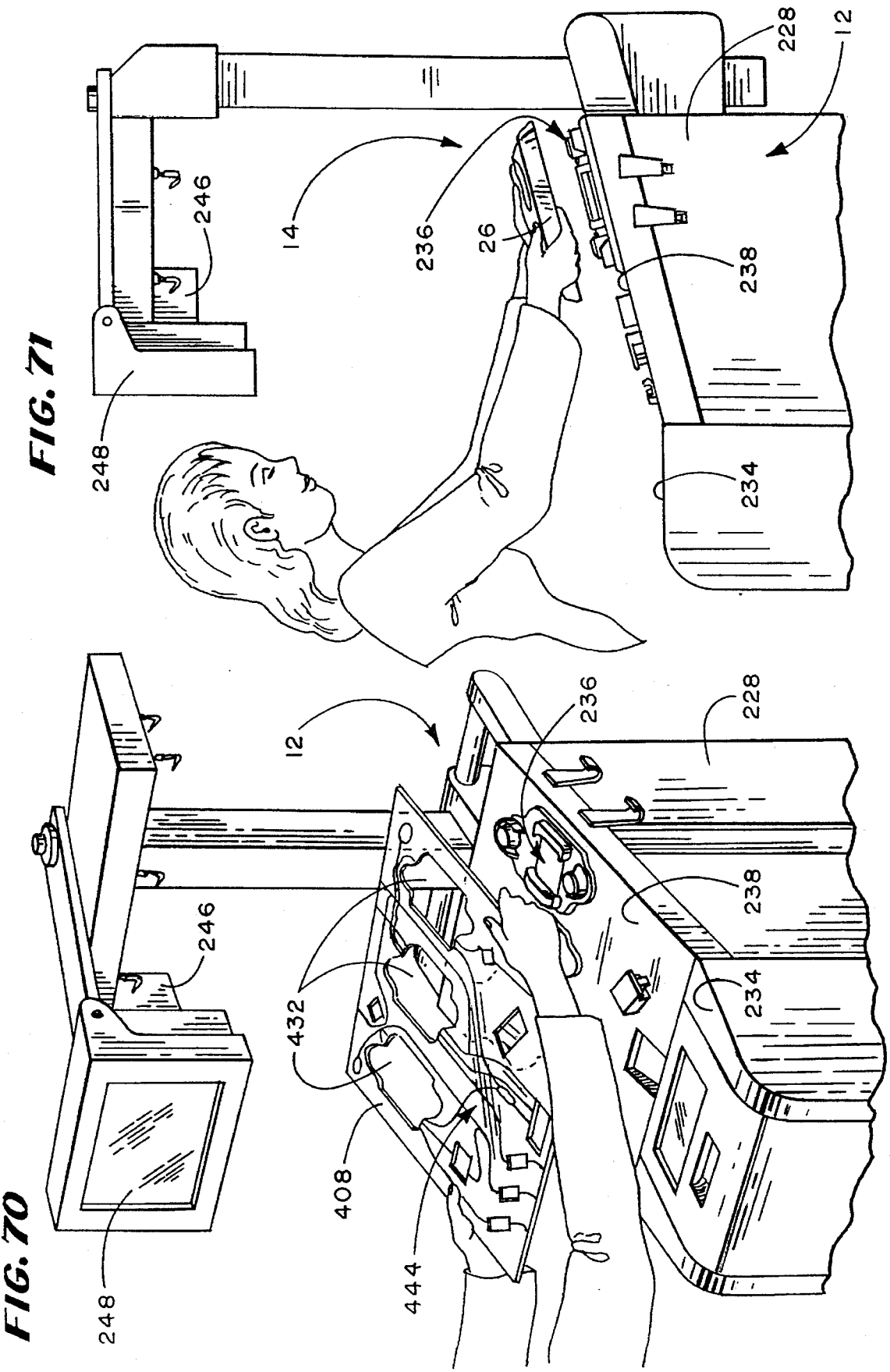
FIGS. 70 to 75 show the steps by which the user sets up the tray-mounted fluid processing assembly on the centrifuge assembly.

The user preferably begins the set-up process by placing a template 408 over the sloped front panel of the centrifuge assembly (see FIG. 70). The template 408 includes cut-out portions 432 that nest over the cassette holding stations 236A/B/C and other operating components on the sloped front panel 238 of the centrifuge cabinet 228.

A layout 444 for the fluid circuit 18 is also printed on the template 408. The layout 444 shows the paths that the tubing branches attached to the cassettes 22A/B/C should take when the fluid circuit assembly 14 is properly set-up for use.

Next (see FIG. 71), the user selects the tray 26 holding the fluid circuit assembly 14 for the desired procedure. After removing the overwrap 162, the user places the selected tray 26 on the template 408 on the front panel 238.

Figure 73:
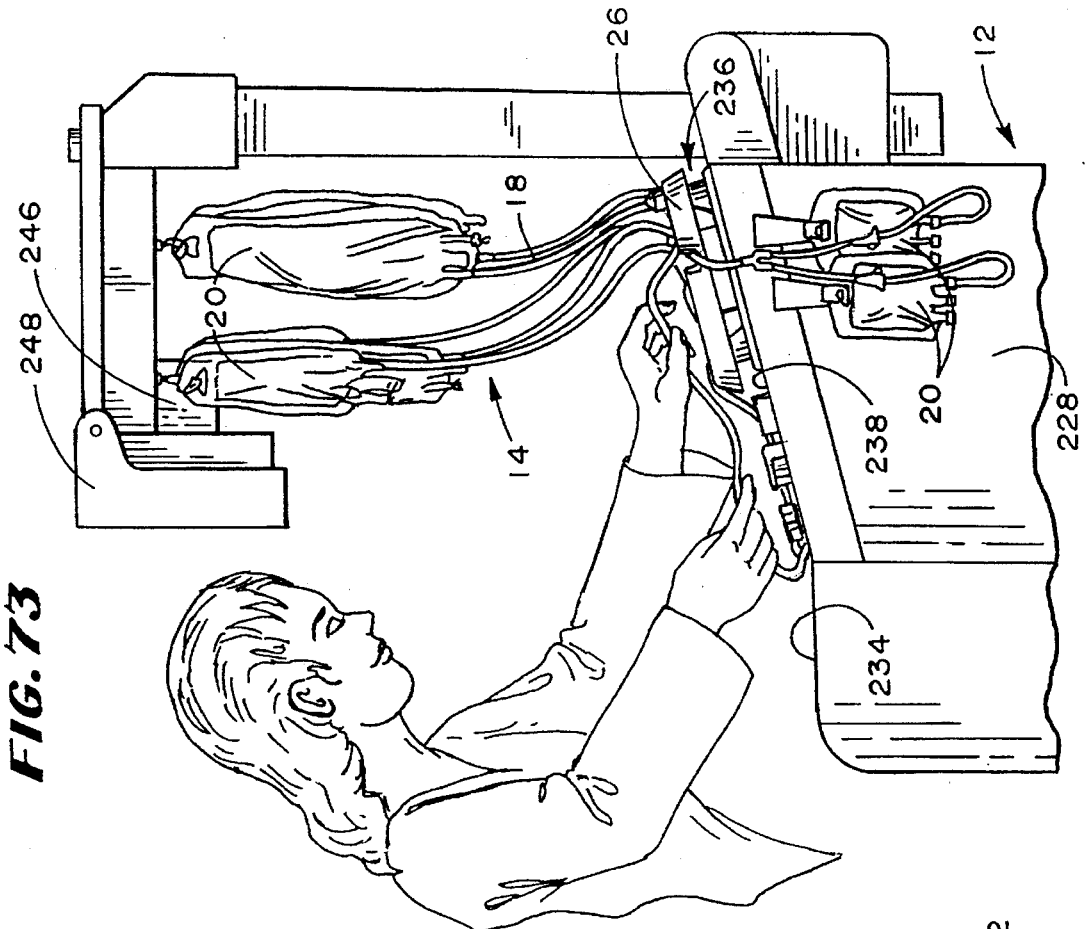

The complementing orientation of the sloped front panel 230 and the tilted rotational axis 344 of the centrifuge 230 conserve both vertical height and horizontal depth, as previously described. Thus, as FIGS. 71 to 73 show, a typical user can reach all the operating components on the front panel 230 to nest the tray 26 upon the cassette holding stations 236 without overreaching or extending his or her body.

As FIG. 71 shows, at this point in the loading process, the user does not press the cassettes 22A/B/C into operative engagement on the holding stations 236, but merely rests them atop the stations 236.

Figure 72:
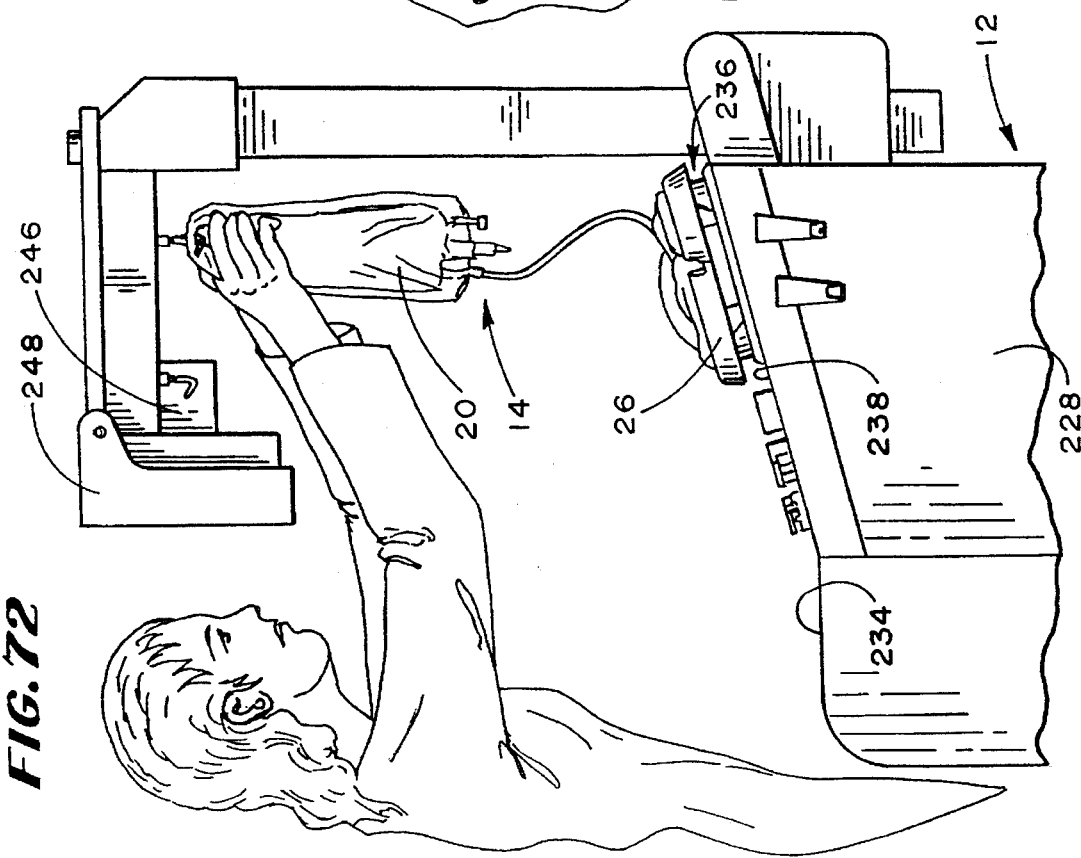

With the tray 26 resting upon, but yet engaged by, the holding stations 236, the user removes the containers 20 from the topmost layer 168 of the tray 26 (see FIG. 72). The user hangs the containers 20 on the designated hangers on the centrifuge assembly 12. As before noted, the typical user can reach these areas of the centrifuge assembly 12 with over-extension or reaching.

The removal of the containers 20 presents the middle layer 166 of the tray 26 to the user. The processing chamber 16, umbilicus 24, and attached tubing branches of the fluid circuit 18 occupy this layer.

As FIG. 73 shows, the user unpacks the fluid circuit 18. Following the template layout 444, the user lays the fluid circuit 18 out upon the front panel 238, making connections as required with the clamps 240 and sensors 244.

As FIG. 74 shows, the user next folds open the door 234 to gain for access to the compartment 232 and the centrifuge 230 it holds. As previously described, the mutual orientation between the sloped front panel 238 and the tilted rotational axis 344 of the centrifuge 230 allow the typical user access to the chamber assembly 350 without bending or stooping.

The user pivots the first umbilicus mount 392 into its loading position and opens the clamp 400 (as FIG. 74 shows). The user then pivots the yoke cross arm 360 to place the chamber assembly 350 into its upward facing orientation. The user next moves the spool 376 into its uplifted position for receiving the processing chamber 16.

The user wraps the processing chamber 16 about the upraised and open spool 376. The user clamps the umbilicus supports 204 and 206 and thrust bearing member 214 into their designated mounts, respectively 392, 396, and 394. Then, the user moves the spool 376 into its closed operating position. The user pivots and latches the yoke cross member 360 into its downward facing operating position. The user closes the door 234 to the centrifuge compartment 232.

The removal of the processing chamber 16, umbilicus 24, and tubing 18 from the tray 26 in the proceeding steps presents the bottommost layer 164 of the tray 26 to the user. The cassettes 22A/B/C occupy this layer 164.

Figure 75:
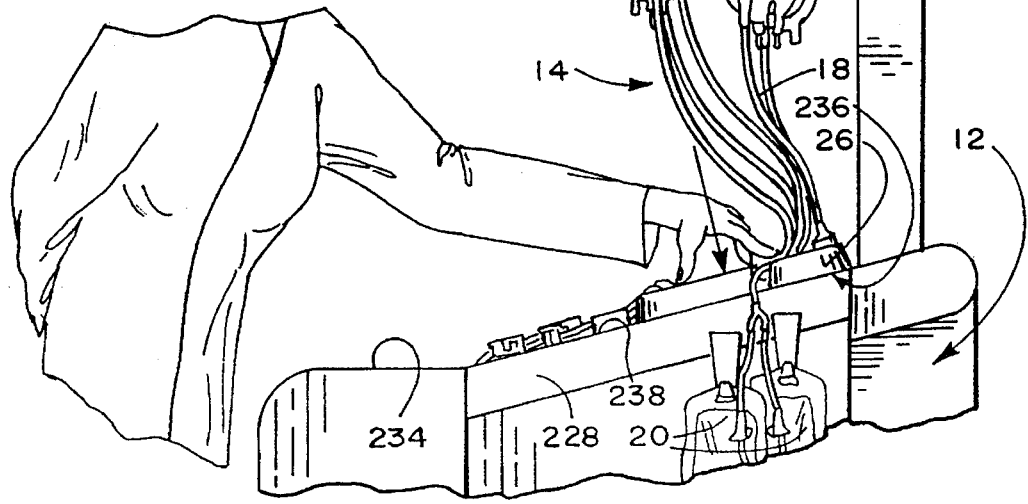

As FIG. 75 shows, the user presses down upon the cassettes 22A/B/C, placing them into operative engagement with the stations 236. The user completes the set up by operating the pump modules 254 to load the tubing loops 134 and 136 of each cassette 22A/B/C onto the pump rotors 298, as previously described.

The set up is now complete. The controller 246 proceeds to govern the operation of the centrifuge assembly 12 to carry out the desired procedure.

FIGS. 76 to 79 show the steps the user follows in disposing of the processing assembly 14 when the procedure is completed.

Figure 76:
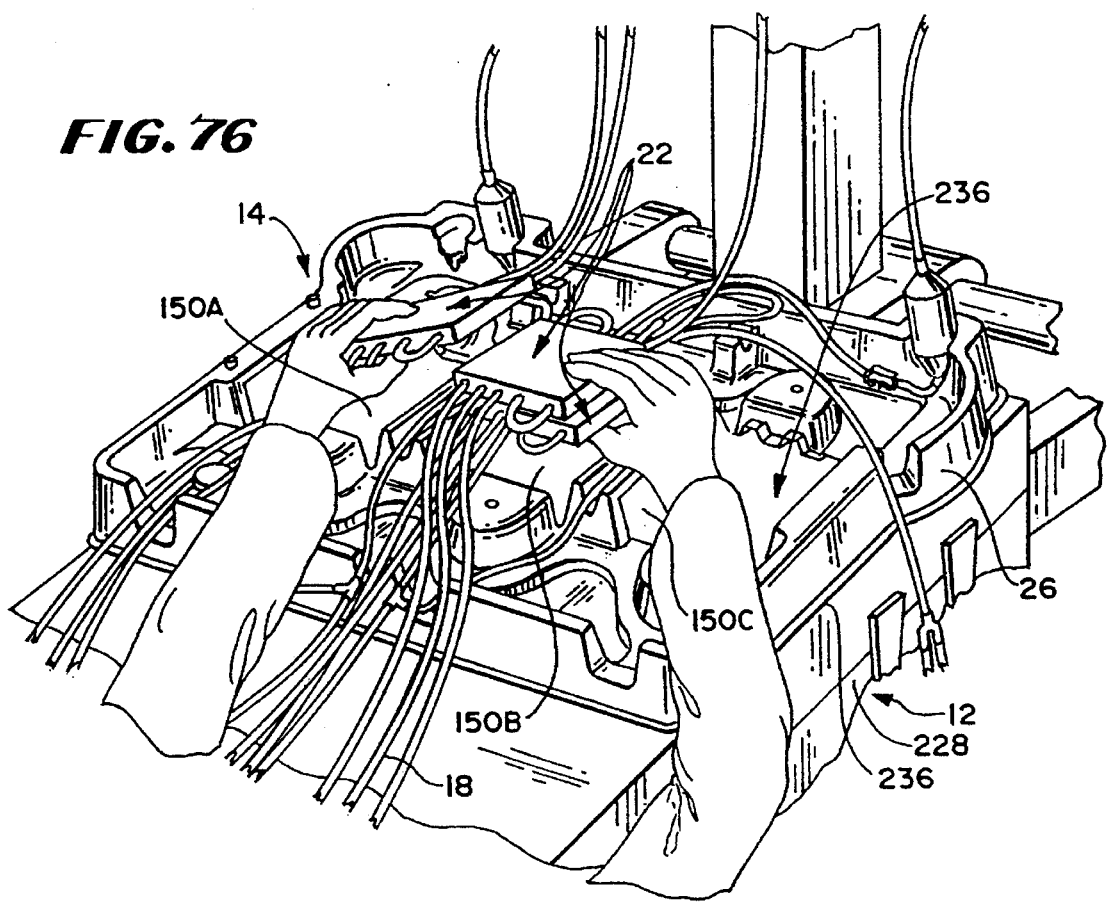
FIGS. 76 to 79 show the steps by which the user removes and disposes of the fluid processing assembly after a given processing procedure.

As FIG. 76 shows, with the tray 26 supported on the front panel 236 of the centrifuge cabinet 228, the user collects the components of the fluid circuit assembly 14 in the tray 26 for disposal. The user can remove the cassettes 22A/B/C from the holding stations 236, freeing them from the cut-outs 150A/B/C in the tray. Once freed, the cassettes 22A/B/C can be stacked one atop the other in the tray 26 (as FIG. 76 shows). Alternatively, the user can keep the cassettes 22A/B/C in place within the tray 26.

Figure 77:
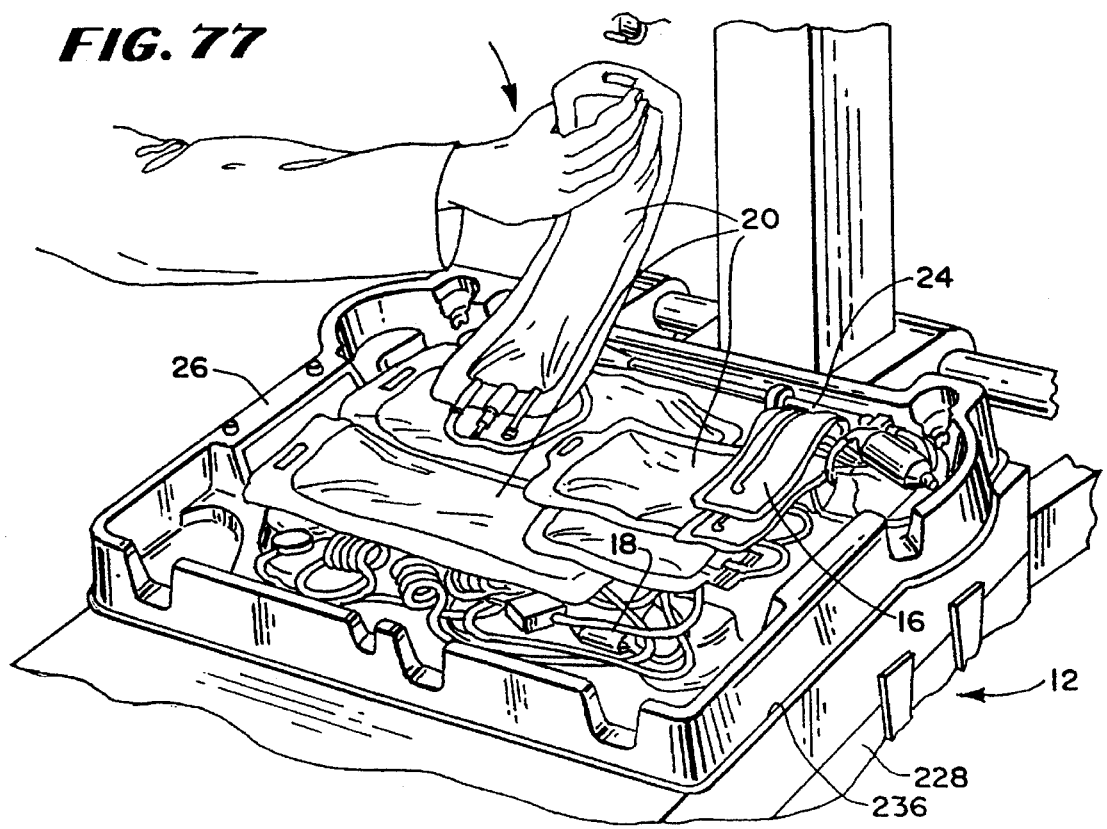

The user then unloads the centrifuge 230, freeing the processing chamber 26 and umbilicus 24 and placing them in the tray 26 (as FIG. 77 shows). The remaining tubing 18 and containers 20 are collected and placed in the tray 26.

Figure 78:
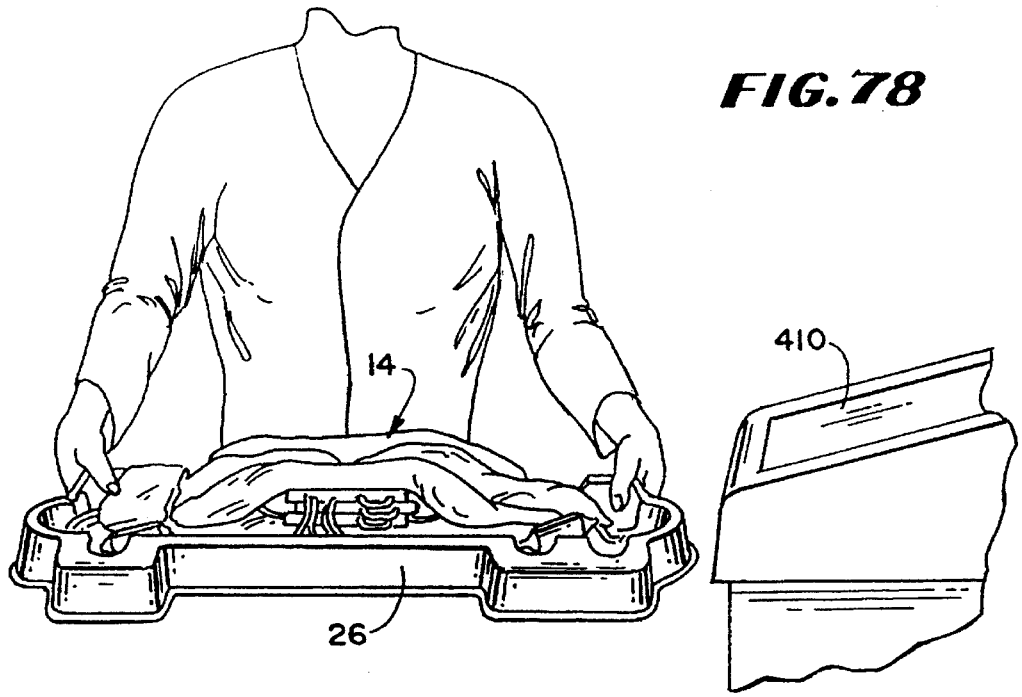

As FIG. 78 shows, the user lifts the tray 26 and the fluid circuit assembly 14 carried within it from the centrifuge assembly 12. The user carries the tray 26 to a receptacle 410 and up-ends the tray 26 to dump the components 14 from it.

Figure 79:
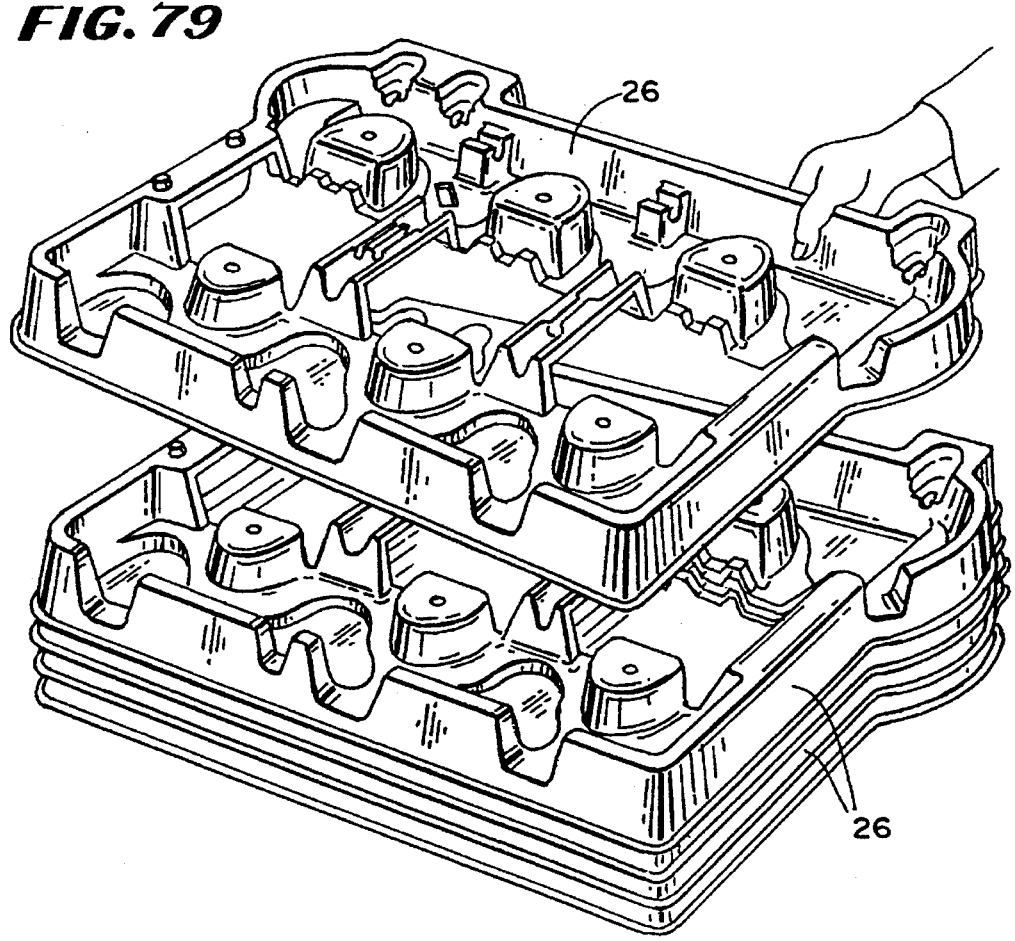

As FIG. 79 shows, once unloaded, the trays 26 can nested together and stored for return to the manufacturer for repacking, sterilization, and reuse. The trays 26 can also be sent to a recycling facility.

Alternatively, the user can dispose of both the tray 26 and components 14 at the same time.

Various features of the invention are set forth in the following claims.

We claim:

1. A peristaltic pumping apparatus comprising
   a peristaltic pumping element including a pump rotor rotatable about a rotational axis and a pump race circumferentially spaced about the axis,
   a pump tube cassette including a body having a side edge and means on the side edge for supporting a flexible tubing loop in an erect, outwardly bowed position generally perpendicular to the side edge for placement within the pump race and for removal from the pump race by moving the body and the tubing loop, respectively, toward and away from the pumping element in a direction generally parallel to the rotational axis of the pump rotor, and
   a surface spaced from the peristaltic pumping element in a plane that extends generally perpendicular to the rotational axis, including a gripping jaw assembly on the surface that opens to receive the pump tube cassette body as the body and the tubing loop are moved in the generally parallel direction toward the pumping element to place the tubing loop within the pump race and that closes against the pump tube cassette body to secure the pump tube cassette body on the surface in an orientation in which the tubing loop lies within the pump race for engagement with the peristaltic pump rotor.

2. An apparatus according to claim 1
   wherein the gripping jaw assembly opens to release the pump tube cassette body as the body and the tubing loop are moved in the generally parallel direction away from the pumping element to remove the tubing loop from the pump race.

3. An apparatus according to claim 1
   and further including means for releasably locking the gripping jaw assembly when closed.

4. A peristaltic pumping apparatus comprising
   a peristaltic pumping element including first and second pump rotors, each including a pump race, the first and second pump rotors rotating about, respectively, first and second generally parallel rotational axes, the pump race for each pump rotor being circumferentially spaced about the respective one of the first and second rotational axes, the first and second pump rotors being spaced apart by a surface that extends generally perpendicular to the rotational axes,
   a pump tube cassette including a body having first and second oppositely spaced side edges and means on the first and second side edges for supporting, respectively, first and second flexible tubing loops in an erect, outwardly bowed position generally perpendicular to the respective side edge for placement, respectively, within the pump races of the first and second pump rotors and for removal from the respective pump races by moving the body and the first and second tubing loops, respectively, toward and away from the pumping element in a direction generally parallel to the first and second rotational axis, and
   the surface between the first and second pump rotors including a gripping jaw assembly that opens to receive the pump tube cassette body as the body and the first and second tubing loops are moved in the generally parallel direction toward the pumping element to place the first and second tubing loops within their respective pump races and that closes against the pump tube cassette body to secure the pump tube cassette body on the surface in an orientation in which the first and second tubing loops lie within their respective pump races for engagement with the respective peristaltic pump rotors.

5. An apparatus according to claim 4
   wherein the gripping jaw assembly opens to release the pump tube cassette body as the body and the first and second tubing loops are moved in the generally parallel direction away from the pumping element to remove the first and second tubing loops from their respective pump races.

6. An apparatus according to claim 4
   and further including means for releasably locking the gripping jaw assembly when closed.

7. A peristaltic pumping apparatus comprising
   a peristaltic pumping element including a pump rotor and pump race,
   a pump tube cassette including a body and means on the body for supporting a flexible tubing loop in an erect, outwardly bowed position for placement within the pump race and for removal from the pump race by moving the body, respectively, toward and away from the pumping element,
   a surface juxtaposed the peristaltic pumping element including first and second gripping elements, each movable between a mutually open position to receive between them the pump tube cassette body and a mutually closed position gripping the pump tube cassette body to secure it on the surface, and the gripping elements being movable toward the mutually open position in response to movement of the body toward the surface to place the tubing loop within the pump race and movable toward the mutually closed position when the body rests on the surface in an orientation in which the tubing loop lies within the pump race for engagement with the peristaltic pump rotor, and
   a locking mechanism that releasable holds the gripping elements in the mutually closed position including an electrically actuated solenoid selectively moveable into contact with at least one of the gripping elements to hold the gripping element in the mutually closed position.

8. An assembly according to claim 7 wherein the locking mechanism includes a manually actuated release.

9. A peristaltic pumping apparatus comprising a peristaltic pumping element including a pump rotor and pump race, a pump tube cassette including a body and means on the body for supporting a flexible tubing loop in an erect, outwardly bowed position for placement within the pump race and for removal from the pump race by moving the body, respectively, toward and away from the pumping element, a surface juxtaposed the peristaltic pumping element including first and second gripping elements, each movable between a mutually open position to receive between them the pump tube cassette body and a mutually closed position gripping the pump tube cassette body to secure it on the surface, and a gripping mechanism for moving the gripping elements toward the mutually open position in response to movement of the body toward the surface to place the tubing loop within the pump race and for moving the gripping element toward the mutually closed position when the body rests on the surface in an orientation in which the tubing loop lies within the pump race for engagement with the peristaltic pump rotor, and a locking mechanism that releasable holds the gripping elements in the mutually closed position including an electrically actuated solenoid selectively moveable into contact with at least one of the gripping elements to hold the gripping element in the mutually closed position.

10. An assembly according to claim 9 wherein the locking mechanism includes a manually actuated release.

11. An assembly according to claim 9 wherein the gripping mechanism includes a spring element for biasing the gripping elements toward the mutually closed position.

12. An assembly according to claim 9 wherein the gripping mechanism moves the gripping element toward the mutually open position in response to contact with the pump tube cassette body during movement toward the surface.

13. An assembly according to claim 12 wherein the gripping mechanism includes a detent surface that relieves the contact when the pump tube cassette body is adjacent the surface.

14. An assembly according to claim 13 wherein the gripping mechanism includes a spring element to move the gripping elements toward the mutually closed position in the absence of the contact.

15. An assembly according to claim 9 wherein the gripping mechanism moves the gripping elements toward the mutually open position in response to movement of the pump tube cassette body away from the surface to remove the tubing loop from the pump race.

16. An assembly according to claim 15 wherein the gripping mechanism moves the gripping element toward the mutually open position in response to contact with the pump tube cassette body during movement away from the surface.

17. An assembly according to claim 16 wherein the gripping mechanism includes a detent surface that relieves the contact when the pump tube cassette body is spaced a predetermined distance from the surface.

18. An assembly according to claim 17 wherein the gripping mechanism includes a spring element that moves the gripping elements toward the mutually closed position in the absence of the contact.

* * * * *